US012616363B2

(12) United States Patent
Small et al.

(10) Patent No.: US 12,616,363 B2
(45) Date of Patent: May 5, 2026

(54) SYSTEMS, METHODS, AND APPARATUS FOR TELE-OTOSCOPY

(71) Applicant: Kenvue Brands LLC, Summit, NJ (US)

(72) Inventors: Eleanor F. Small, Philadelphia, PA (US); Raymond T. Hebert, Dunes City, OR (US); Sean James Coyle, Pennington, NJ (US); Stephen Anton, Union, NJ (US)

(73) Assignee: Kenvue Brands LLC, Summit, NJ (US)

( * ) Notice: Subject to any disclaimer, the term of this patent is extended or adjusted under 35 U.S.C. 154(b) by 499 days.

(21) Appl. No.: 18/157,872

(22) Filed: Jan. 23, 2023

(65) Prior Publication Data

US 2023/0240523 A1 Aug. 3, 2023

Related U.S. Application Data

(60) Provisional application No. 63/267,233, filed on Jan. 28, 2022.

(51) Int. Cl.
*A61B 1/227* (2006.01)
*A61B 1/05* (2006.01)
(Continued)

(52) U.S. Cl.
CPC .............. *A61B 1/227* (2013.01); *A61B 1/053* (2013.01); *A61B 1/0684* (2013.01); *A61B 5/7465* (2013.01)

(58) Field of Classification Search
CPC ....... A61B 1/277; A61B 1/2775; A61B 1/227; A61B 1/2275; A61B 3/12
See application file for complete search history.

(56) References Cited

U.S. PATENT DOCUMENTS

| | | | | |
|---|---|---|---|---|
| 5,499,066 A | * | 3/1996 | Farmer | ................ A61B 3/1208 |
| | | | | 351/205 |
| 8,743,194 B2 | | 6/2014 | Fletcher et al. | |
| 8,786,695 B2 | | 7/2014 | Fletcher et al. | |

(Continued)

FOREIGN PATENT DOCUMENTS

| | | |
|---|---|---|
| JP | 2005064858 A | 3/2005 |
| WO | WO 2006/095898 A | 9/2006 |

(Continued)

OTHER PUBLICATIONS

International application PCT/US2023/061244 search report and written opinion mailed May 10, 2023.

*Primary Examiner* — Eduardo C Robert
*Assistant Examiner* — Anna V. Little

(57) ABSTRACT

An otoscope apparatus having an objective lens configured to focus light from an object, a field lens positioned parallel to the objective lens along an optical axis, a first aperture and a second aperture positioned, respectively, at a distal end and a proximal end of the objective lens, and a third aperture positioned at a distal end of the field lens. The otoscope apparatus is adapted to be releasably attached to a camera of a smart device. The otoscope apparatus may capture a picture or video of the outer ear, the middle ear, and/or the ear canal of a patient utilizing the camera of the smart device. Such a picture or video of the outer ear, the middle ear, and/or the ear canal may be sent to a remote healthcare professional for diagnosis of an ear infection.

23 Claims, 29 Drawing Sheets

(51) Int. Cl.
   *A61B 1/06*      (2006.01)
   *A61B 5/00*      (2006.01)

(56)               References Cited

U.S. PATENT DOCUMENTS

| | | | |
|---|---|---|---|
| 9,154,594 B2 | 10/2015 | Fletcher et al. | |
| 9,325,884 B2 | 4/2016 | Fletcher et al. | |
| 9,445,713 B2 | 9/2016 | Douglas et al. | |
| 9,523,845 B2 | 12/2016 | Fletcher et al. | |
| 10,126,539 B2 | 11/2018 | Fletcher et al. | |
| 10,616,457 B2 | 4/2020 | Fletcher et al. | |
| 10,989,907 B2 | 4/2021 | Fletcher et al. | |
| 11,172,825 B1 * | 11/2021 | Ayanruoh | A61B 3/12 |
| 2013/0107109 A1 * | 5/2013 | Yang | H04N 23/51 |
| | | | 359/827 |
| 2013/0128223 A1 * | 5/2013 | Wood | A61B 3/1208 |
| | | | 351/246 |
| 2015/0065803 A1 * | 3/2015 | Douglas | G06T 7/143 |
| | | | 600/200 |
| 2015/0250381 A1 * | 9/2015 | Bedard | G02B 23/2469 |
| | | | 600/200 |
| 2016/0073875 A1 * | 3/2016 | Goldfain | A61B 1/227 |
| | | | 351/205 |
| 2016/0106369 A1 * | 4/2016 | Yetik | A61B 1/227 |
| | | | 600/476 |
| 2016/0338590 A1 * | 11/2016 | Sagalovich | A61B 1/00066 |
| 2017/0119237 A1 * | 5/2017 | Bedard | G02B 7/021 |
| 2017/0119250 A1 * | 5/2017 | Kolachalama | A61B 3/14 |
| 2017/0303857 A1 * | 10/2017 | Perkins | H04N 7/185 |
| 2020/0237272 A1 | 7/2020 | Lin et al. | |
| 2020/0336630 A1 * | 10/2020 | Fletcher | H04N 17/002 |
| 2021/0019884 A1 | 1/2021 | Kawai et al. | |
| 2022/0007927 A1 * | 1/2022 | Lia | A61B 1/00195 |

FOREIGN PATENT DOCUMENTS

| | | | | |
|---|---|---|---|---|
| WO | WO-2018010849 A1 * | 1/2018 | | A61B 1/227 |
| WO | WO 2019/143668 A | 7/2019 | | |

* cited by examiner

Align the otoscope tool along the dotted line and tighten knob to secure

FIG. 10C

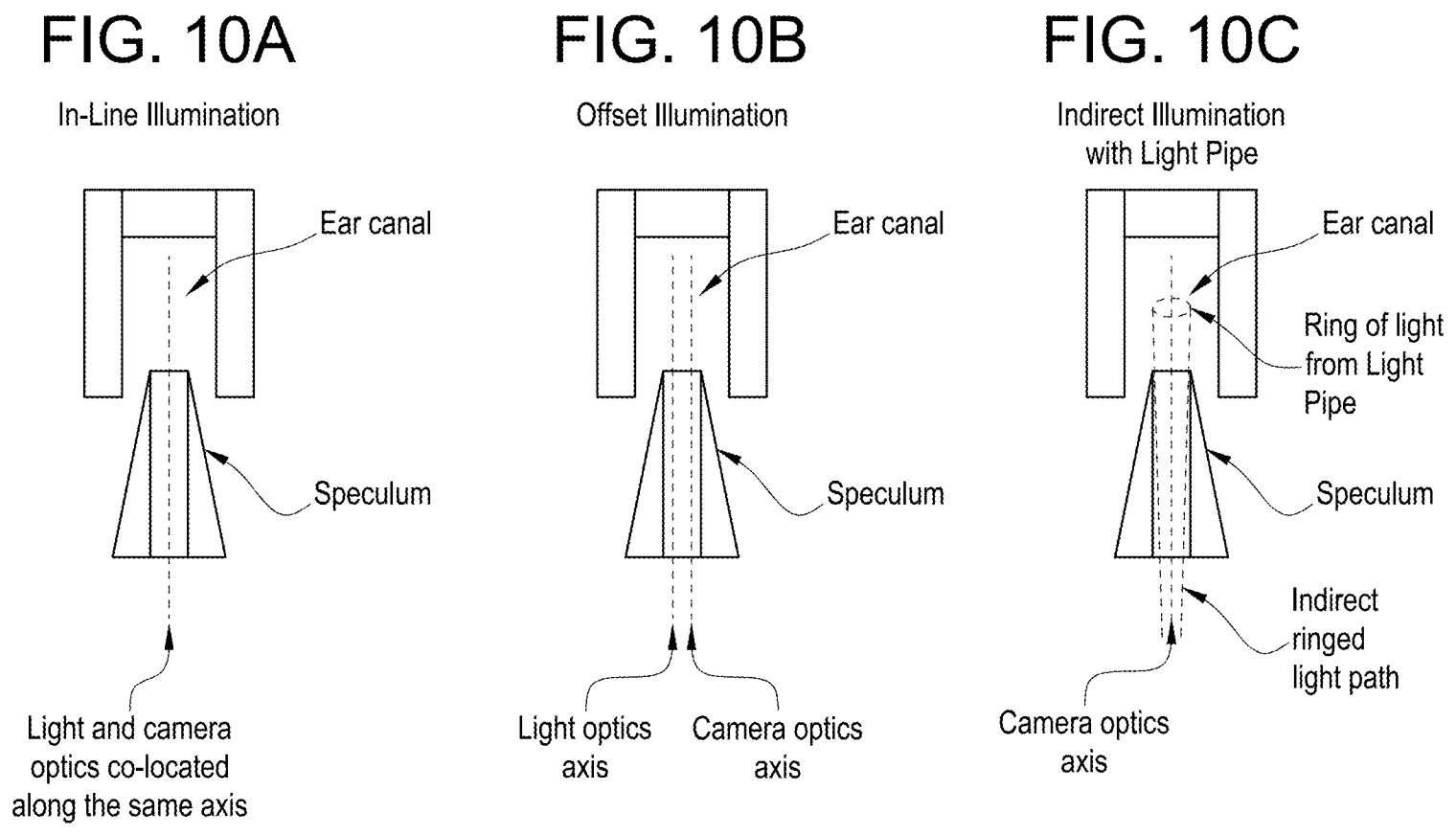

Indirect Illumination
with Light Pipe

Ear canal

Ring of light
from Light
Pipe

Speculum

Indirect
ringed
light path

Camera optics
axis

FIG. 10B

Offset Illumination

Ear canal

Speculum

Camera optics
axis

Light optics
axis

FIG. 10A

In-Line Illumination

Ear canal

Speculum

Light and camera
optics co-located
along the same axis

Detector Image: Incoherent Irradiance
lightpipe_0617-2_short+window_glare_nocap
12/30/2021
Detector 21, NSCG Surface 1: camera chip
Size 4.580 W X 3.440 H Millimeters, Pixels 1000 W X 1000 H, Total Hits - 335532
Peak Irradiance : 4.6676E-002 Watts/cm^2
Total Power     : 5.4408E-004 Watts 1000B (Inner Otoscope)

OPTICS
SUBASSEMBLY

SECTION

Detector Image: Incoherent Irradiance 0.0100
0.0090
0.0080
0.0070
0.0060
0.0050
0.0040
0.0030
0.0020
0.0010
0.0000 lightpipe_0617-2_short+window_glare
12/30/2021
Detector 23, NSCG Surface 1: camera chip
Size 4.580 W X 3.440 H Millimeters, Pixels 1000 W X 1000 H, Total Hits - 38998
Peak Irradiance : 1.1910E-002 Watts/cm^2
Total Power : 4.2564E-005 Watts

SYSTEMS, METHODS, AND APPARATUS FOR TELE-OTOSCOPY

CROSS-REFERENCE TO RELATED APPLICATIONS

This application claims the benefit of U.S. Provisional Application No. 63/267,233, filed on Jan. 28, 2022, the contents of which are incorporated by reference in their entirety herein.

BACKGROUND

An otoscope may be used for diagnosing and/or identifying problems of the outer ear, the middle ear, and/or the ear canal, such as issues with a tympanic membrane or an ear infection (e.g., acute otitis media). When joined with a camera, the otoscope may be used for remote diagnosis when images or videos may be recorded by the user. For example, the otoscope may be used for tele-otoscopy and may enable a user to record an image of an ear canal of a patient (e.g., an image of the tympanic membrane). The image may be sent to a remote physician for diagnosis. But it is imperative that a clear picture or video be taken.

SUMMARY

Disclosed herein are systems, methods, and apparatus, for using a removable optical element, such as an otoscope, in combination with a smart device, such as a smartphone in such a way that a picture or video (e.g., a clear picture or a clear video) may be taken.

According to an embodiment, an otoscope apparatus may include an objective lens configured to focus light from an object, a field lens positioned parallel to the objective lens along an optical axis, a first aperture and a second aperture positioned, respectively, at a distal end and a proximal end of the objective lens, and a third aperture positioned at a distal end of the field lens. The otoscope apparatus may be adapted to be releasably attached to a camera of a smart device.

According to an embodiment, the first aperture, second aperture and third aperture may be adapted to reduce veiling glare.

According to an embodiment, the first aperture, second aperture and third aperture may have a diameter between 0.5 mm and 4.5 mm. According to a further embodiment, the first aperture may have a diameter of about 0.7 mm, the second aperture may have a diameter of about 1.2 mm, and the third aperture may have a diameter of about 4.25 mm.

According to various embodiments, a ratio of a diameter of the first aperture to a diameter of the second aperture may be about 1:2, and/or a ratio of a diameter of the second aperture to a diameter of the third aperture may be about 1:4.

According to various embodiments, the first aperture may be located about 2.6 mm from the second aperture along the optical axis, and/or the second aperture may be located about 18 mm from the third aperture along the optical axis.

According to an embodiment, a f-number of the first aperture may be adapted to disable an autofocus feature of the camera of the smart device. According to one example, the f-number may be f/45.

According to one embodiment, a working distance between the first aperture and the object may be about 31.5 mm.

According to an embodiment, the otoscope apparatus may further include an eyepiece lens positioned parallel to the field lens along the optical axis.

According to an embodiment, the otoscope apparatus may further include a lens tube and a glare cap adjacent to one another along the optical axis. According to an embodiment, the objective lens and the first aperture may be positioned within the glare cap and the field lens, the second aperture and third aperture may be positioned within the lens tube.

According to an embodiment, the otoscope apparatus may further include a light source and a light pipe attachable to the light source at a proximal end, where the light pipe may terminate at a distal ring portion to illuminate the object. According to an embodiment, the light source may be a light emitting diode (LED). According to an embodiment, the light source may be a flash of the camera of the smart device. According to an embodiment, the light pipe may terminate at or prior to a distal end of the glare cap.

According to an embodiment, the first aperture may have a diameter adapted to prevent a reflection of the light back into the glare cap and/or lens tube.

According to an embodiment, the object may be the outer ear, the middle ear, and/or the ear canal of a patient. According to one example, the object may be the eardrum of a patient.

According to an embodiment, there may be a method for using the otoscope apparatus, where a picture or a video of an outer ear, the middle ear, and/or the ear canal of a patient may be captured by the camera of the smart device. According to a further embodiment, the picture or video of the outer ear, the middle ear, and/or the ear canal may be transmissible to a remote healthcare professional for diagnosis of an ear infection.

BRIEF DESCRIPTION OF THE DRAWINGS

FIGS. 10A-10C depict diagrams of exemplary in-line, offset and indirect illumination embodiments.

DETAILED DESCRIPTION

Figure 1A:
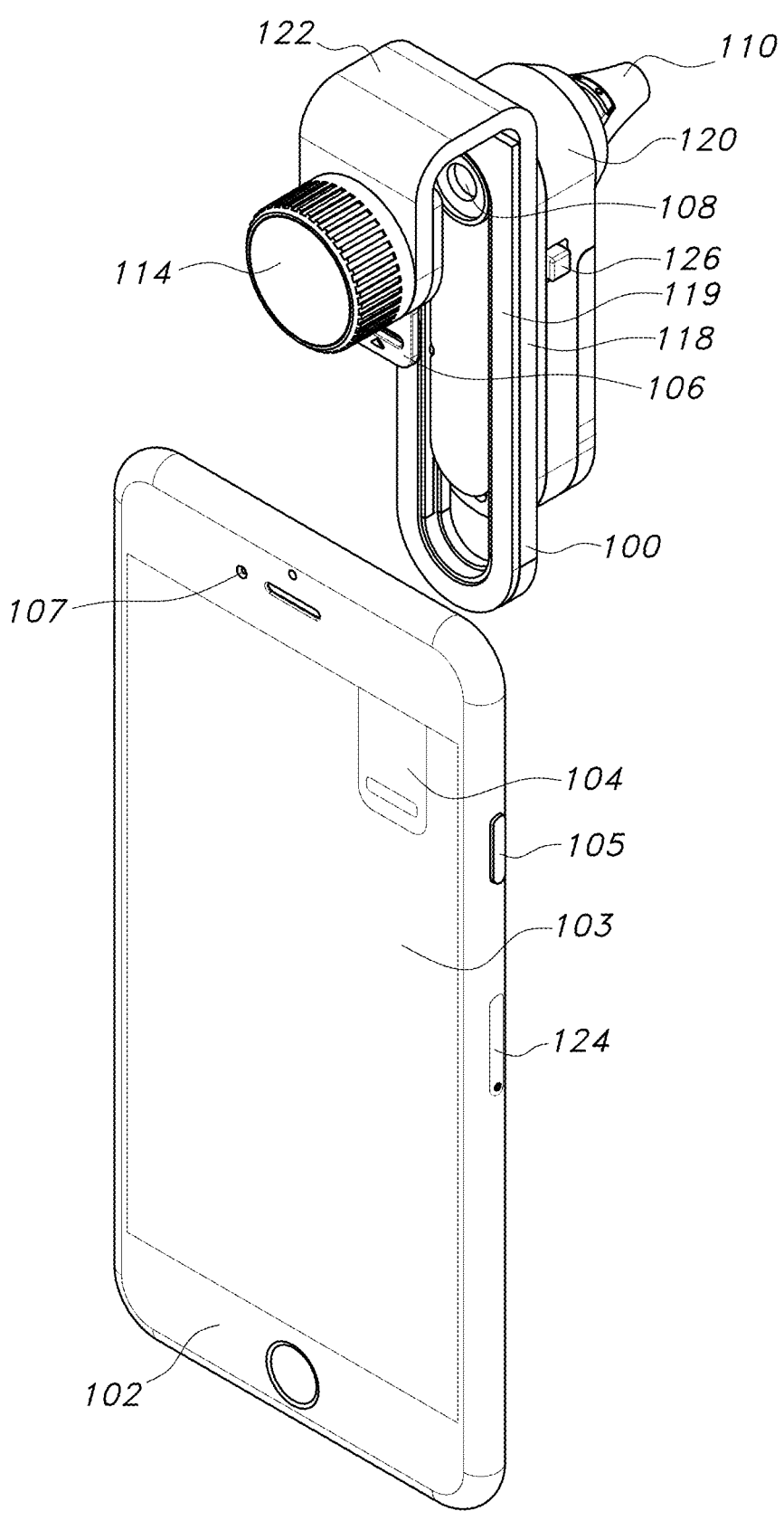
FIGS. 1A-1B depict perspective views of an otoscope clip device that is detached from a smart device, such as a smartphone.

As remote medicine (e.g., tele-medicine) becomes more common, devices may allow individuals to perform tasks to assist doctors, nurses, or other medical practitioners. For example, a user may take a picture or a video within the ear canal of a patient (e.g., an image of the tympanic membrane), so that a remote doctor may diagnose an issue with the outer ear, the middle ear, and/or the ear canal of the patient. To assist in taking a picture or a video of the outer ear, the middle ear, and/or the ear canal, a user may use an otoscope. For example, a user may connect an otoscope to a camera.

Disclosed herein are systems, methods, and apparatus, for attaching an otoscope to a smart device, such as a smartphone. A user may be provided with an ability to align a camera of the smart device with the otoscope in such a way that a picture or a video (e.g., a clear picture or a clear video) may be taken.

A user may attach the otoscope clip to the smart device, may align a portion of the otoscope with the camera of the smart device using the alignment tab, and may secure the otoscope clip to the smart device using the screw clamp assembly to close the clamp. The user may then record an image of an outer ear, a middle ear, and/or an inner ear of a patient and may provide that image to a physician for diagnosis. The recorded image may be analyzed by software on the smart device that may work in conjunction with the otoscope clip to provide image analysis, medical analysis, diagnosis, image taking guidance, and/or the like.

The otoscope may comprise a removable speculum. The otoscope may comprise a light. The light may an incandescent light, a light emitting diode (LED), and/or the like. The light may be powered by a battery, such as a lithium-ion battery, an alkaline battery, and/or the like.

A smart device may be used to provide a camera for an otoscope. The smart device may be a smartphone, a smart tablet (e.g., an iPad), a computer, and/or the like. The smart device may include a camera, which the otoscope may use to take an image. The camera on the smartphone may provide a cost-effective method of providing the otoscope with the camera. For example, smartphones may now be widely available, and users may already have access to one. By providing a user with a device, such as an otoscope clip device, to attach an otoscope to the smartphone, the user may be given the ability to use the otoscope to take images which may then he sent to a medical professional.

When attaching an otoscope to a smartphone with the otoscope clip, the user may wish to align the otoscope with the camera on the smartphone. Aligning the otoscope with the smartphone camera may provide an image that may not be impeded by a component of the otoscope. Aligning the otoscope with the smartphone camera may help keep stray light out of the image (e.g., seal light out of the otoscope) to improve an image quality. To align the otoscope with the camera on the smartphone, a user may have to flip the phone back and forth as the smartphone camera may be on the opposite side of the display.

Figure 1B:
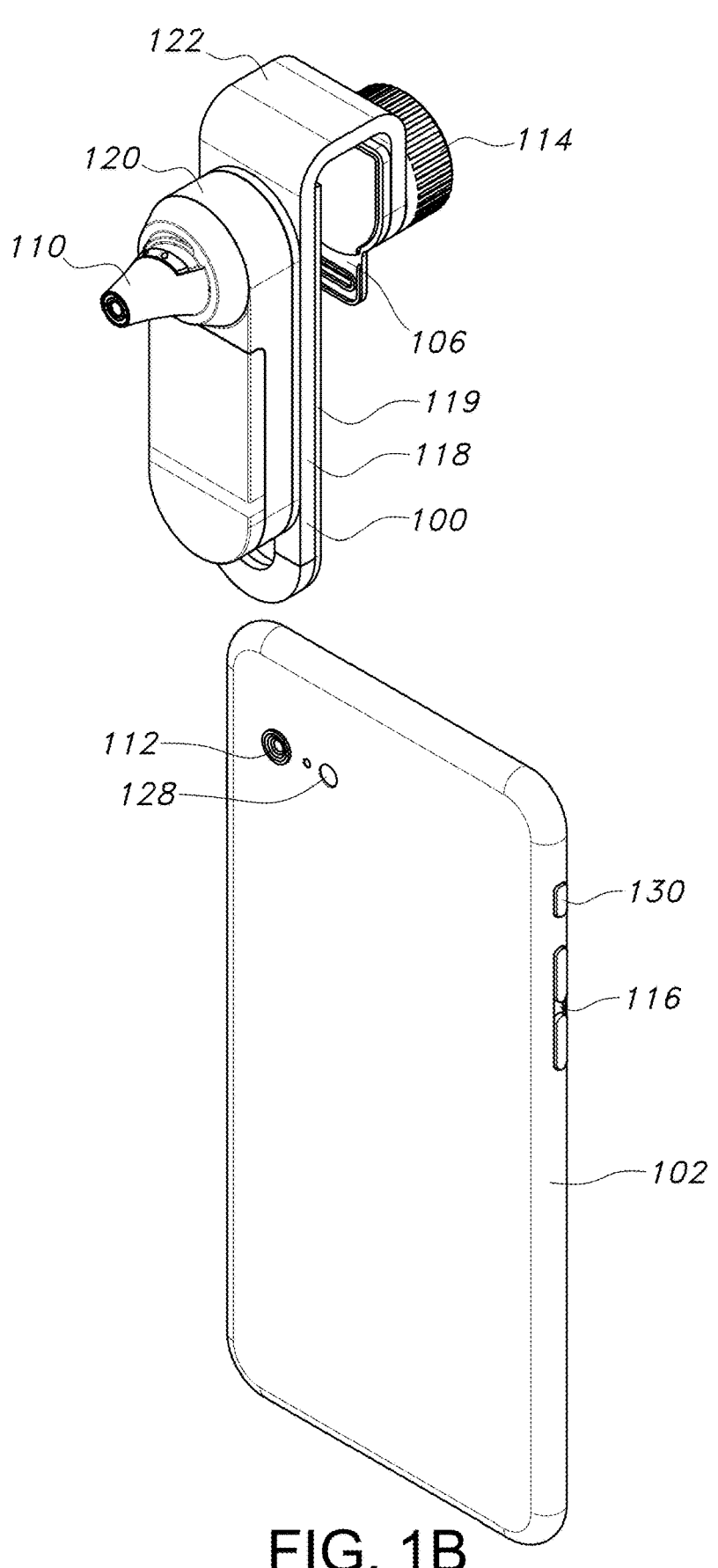

FIGS. 1A-B depict perspective views of an otoscope clip device that is detached from a smart device, such as a smartphone. As shown in FIG. 1A, the otoscope clip device 100 may be detached from smart device 102. FIG. 1A may depict the front side of the smart device 102, and a back side of the otoscope clip device 100. The back side of the otoscope clip device 100 may comprise a knob, such as the knob 114, and an alignment tab, such as the alignment tab 106. The front side of the smart device may comprise a camera, such as the camera 107, which may be directed towards a user, and a display screen, such as the display 103. The front side 102 of the smart device may comprise a button, such as a home button, and a speaker, which a user may use to listen to a phone call. The button 105 may be located on the side of the smart device 102.

The smart device 102 may be a smartphone, a smart tablet (e.g., an iPad), a computer, and/or the like. The smart device 102 may comprise a display, such as the display 103. The display 103 may be a liquid crystal display (LCD) located on the front-facing portion of the smart device. The display 103 may show an alignment image 104. The alignment image 104 may assist the user in aligning a viewing portion of an otoscope with a camera of the smart device, such as the camera at 112 shown with respect to FIG. 1B.

Referring again to FIG. 1A, the alignment image 104 may be complementary to an alignment feature, such as the alignment tab 106, on the otoscope clip device 100 such that a user may align the alignment image 104 with the alignment tab 106. When the alignment image 104 is aligned with the alignment tab 106, the viewing portion 108 of the otoscope may be aligned with the smart device camera 112. Aligning the alignment image 104 with the alignment tab 106 may allow the user to align the viewing portion 108 of the otoscope with the smart device camera 112 while minimizing turning the phone back and forth during the alignment.

The otoscope clip device 100 may comprise a number of components. For example, the otoscope clip device 100 may comprise the clip assembly 122 and/or the otoscope assembly 120.

The otoscope clip device 100 may comprise alignment tab 106. The alignment tab may be a part of the clip assembly 122. The alignment tab 106 may include one or more features to assist in aligning the viewing portion 108 of the otoscope. The one or more features may include a protrusion, a hole, an aperture, a color, a design, an icon, an etching (e.g., a laser etching), a symbol, and/or the like.

The alignment tab 106 may include one or more alignment protrusions. An alignment protrusion of the one or more alignment protrusions may be a protrusion on a surface of the alignment tab 106 that may be aligned with a portion of alignment image 104. For example, alignment tab 106 may include an arrow-shaped alignment protrusion that may be aligned with a line within a portion of the alignment image 104.

The alignment tab 106 may include an alignment design. The alignment design may be an etching on a surface of the alignment tab 106 to assist in the alignment of the viewing portion 108 of the otoscope. For example, the alignment design may be one or more intersecting lines, such as a crosshair, that, when aligned with an alignment image on a smart device, may align the viewing portion 108 of the otoscope with a camera of the smart device.

The alignment tab 106 may include an outer edge that may be aligned with an outer edge of the alignment image 104. The outer edge of the alignment tab 106 may be a shape that may be complementary to the outer edge of the alignment image 104. When the outer edge of the alignment tab 106 is aligned with the outer edge of the alignment image 104, the viewing portion 108 of the otoscope may be aligned with the camera of the smart device.

Alignment tab 106 may include an aperture that may be aligned with an object within alignment image 104. For example, the aperture of alignment tab 106 may align with a bullseye target on alignment image 104, an oval shape within alignment image 104, a line within alignment image 104, a combination thereof, and/or the like. The alignment aperture may assist in aligning the viewing portion 108 of the otoscope. For example, the alignment aperture may cause the viewing portion 108 of the otoscope to be aligned with a smart device camera when the alignment aperture is aligned with a corresponding shape within an image on a display of the smart device.

The alignment tab 106 may be made of a material of a color that may match a color of alignment image 104. The alignment tab 106 may be made of a material of a color that may be complementary to a color of alignment image 104. The alignment tab 106 may be made of a clear material such that a user may see through the clear material and align the alignment tab 106 with the alignment image 104. The alignment tab 106 may be made of a material, such as a resilient material, which may be able to apply a pressure to a surface of the smartphone. For example, alignment tab 106 may be made of plastic, metal, a polymer, and/or the like.

Alignment tab 106 may be placed in a parallel position to another surface of otoscope clip device 100, such as a surface of clip engagement member 118. Alignment tab 106 may be placed in a parallel position to another surface of the otoscope clip device 100 such that the otoscope clip device 100 may form a c-shape. The c-shape may be formed using the parallel position of alignment tab 106 with another surface of the otoscope clip device 100, such as a surface of clip engagement member 118, and may be used to provide a clamp, such as a c-clamp. The clamp may be driven by a knob, such as the knob 114.

The otoscope clip device 100 may comprise knob 114, which may be a knob that may drive a screw clamp assembly. Knob 114 may be a part of the clip assembly 122. Knob 114 may be a cylindrical shape with a flat top surface, a bottom surface with at least a hole, and an outer surface. The outer surface of knob 114 may include a number of splines, knurling, or other texture which may provide a gripping surface. When turned, knob 114 may engage a screw clamp assembly such that a piston that may include alignment tab 106 may be moved towards a surface that is parallel to alignment tab 106. For example, a user may turn knob 114 so that alignment tab 106 moves towards a parallel surface of otoscope clip device 100. Knob 114 may cause the alignment tab 106 to move towards clip engagement member 118 such that alignment tab 106 and the clip engagement member 118 may clamp onto the smart device 102.

The otoscope clip device 100 may comprise clip engagement member 118. The clip engagement member 118 may be part of the clip assembly 122. The clip engagement member 118 may have a first surface and a second surface. The first surface of the clip engagement member 118 may face the back side of smart device 102. The first surface of the clip engagement member 118 may include an anti-skid material and/or an anti-scratch material. For example, the first surface of the clip engagement member 118 may be made of rubber to prevent scratching and/or damage to smart device 102 and to prevent otoscope clip device 100 from moving when it is attached to the smart device 102. The clip engagement member 118 may include an elongated aperture. The elongated aperture may allow viewing portion 108 to protrude into or through the clip engagement member 118. This may allow viewing portion 108 to be moved into a number of positions such that viewing portion 108 may be aligned with smart device camera 112.

The clip engagement member 118 may include a number of features to allow the viewing portion 108 to be placed in one or more positions. For example, the clip engagement member 118 may include a protrusion in a side of clip engagement member 118 that may have a complimentary notch in the otoscope assembly 120, which may allow the otoscope assembly 120 and/or the viewing portion of the otoscope to be locked in a position.

The clip engagement member 118 may allow the otoscope assembly 120 to be attached and/or connected to clip assembly 122. The clip engagement member 118 may be a portion of a c-clamp that is part of clip assembly 112. The clip engagement member 118 may allow the otoscope assembly 120 to be movably attached to clip assembly 122. For example, clip engagement member 118 may allow otoscope assembly 120 to move into one or more positions within clip assembly 122. The clip engagement member 118 may allow the otoscope assembly 120 to be removably attachable to clip assembly 122. For example, clip engagement member 118 may allow otoscope assembly 120 to be attached to and/or removed from clip assembly 122.

The contact surface 119 may be in contact with the clip engagement member 118. The contact surface 119 may comprise an anti-skid material that may prevent slippage. The contact surface 119 may be or may comprise a gasket. The gasket may prevent slippage, may protect a phone surface, and/or may act as a light block to prevent light leakage from the device. For example, the gasket may prevent ambient light from entering the optics.

The otoscope clip device 100 may comprise a viewing portion of an otoscope, such as the viewing portion 108. The viewing portion of the otoscope may be a part of the otoscope assembly 120. Viewing portion 108 may be where an image may come into focus from usage of the otoscope such that the image may be viewed at viewing portion 108. The viewing portion 108 of the otoscope may be where a user or a camera may look into the otoscope. For example, the viewing portion 108 may be used to view into an ear of a patient, may be used to take a picture or a video of an outer ear, a middle ear, and/or an ear canal of the patient, and/or the like. As described herein, viewing portion of 108 may come in contact with a camera or may be aligned with a camera.

The otoscope clip device 100 may comprise an otoscope assembly 120. The otoscope assembly 120 may comprise an otoscope. The otoscope assembly 120 may comprise the outer tip housing 110. The otoscope assembly 120 may comprise the light switch 126. The light switch 126 may control a light that may be within or near outer tip housing 110. For example, the light switch may turn on or off a light, which may be battery powered, that may be seen through an opening in the distal end of the outer tip housing 110. This may be done, for example, to provide light within an outer ear, a middle ear, and/or an ear canal of a patient such that a photo may be taken.

The otoscope clip device 100 may comprise the outer tip housing 110. The outer tip housing 110 may have a distal end with an opening that may peer into an outer ear, a middle ear, and/or an ear canal of a patient when a speculum is attached to the outer clip 110. The outer tip housing 110 may have a proximal end that may be connected to the otoscope assembly 120. The outer tip housing 110 may include a radial slot that may allow a removable speculum to be attached to the outer tip housing 110. For example, the removable speculum may be attached to the outer tip housing 110 via the radial slot such that the otoscope assembly 120 may be used to take a picture or a video of an outer ear, a middle ear, and/or an ear canal of a patient. The otoscope portion of the otoscope clip device 100 may provide an optic magnification of the outer ear, middle ear, and/or ear canal of the patient.

As shown in FIG. 1B, otoscope clip device 100 may be detached from smart device 102. FIG. 1B shows the back side of the smart device 102, and the front side of the otoscope clip device 100. The back side of the smart device 102 may include the light 128, and a smartphone camera, such as the smart device camera 112. The smart device camera 112 may face away from a user when the user is viewing the display screen, such as the display 103, of the smart device 102.

As described here in the otoscope clip device 100 may include the outer tip housing 110. The outer tip housing 110 may include an opening. A removable speculum may attach to and/or cover the outer tip housing 110. When the alignment tab 106 is aligned with the alignment image 104, the outer tip housing 110 may be situated in such a way as to be aligned with smart device camera 112. For example, an opening of the outer tip housing 110 may be aligned with the smart device camera 112, and the viewing portion 108 of the otoscope may be aligned with the smart device camera 112.

Figure 1C:
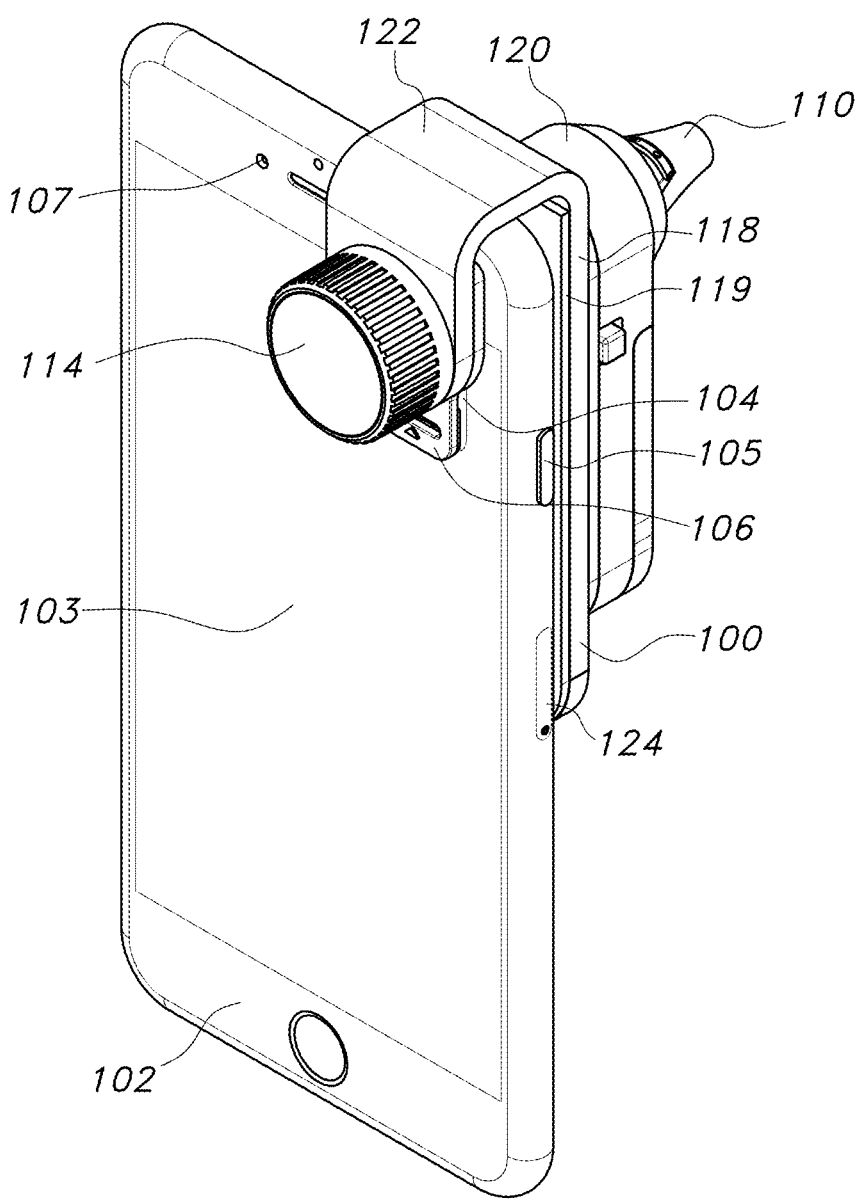
FIGS. 1C-1D depict perspective views of an otoscope clip device that is attached to a smart device, such as a smartphone.
Figure 1D:
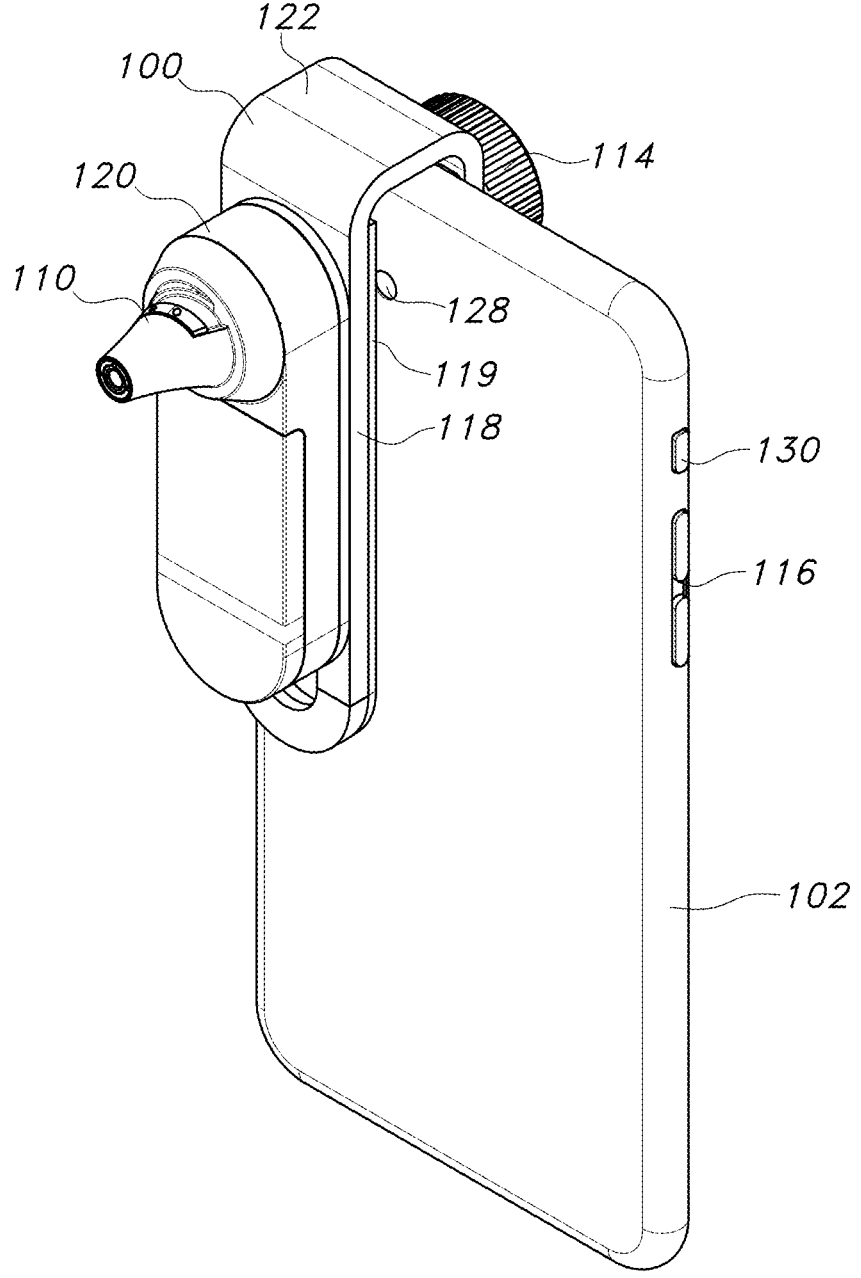

FIGS. 1C-D depict perspective views of an otoscope clip device that is attached to a smart device, such as a smartphone. As shown in FIG. 1C, otoscope clip device 100 may be attached to smart device 102. FIG. 1C may depict the front side of a smart device 102, and the back side of the otoscope clip device 100. The back side of otoscope clip device 100 may comprise a knob, such as 114, an alignment tab, such as alignment tab 106. The front side of the smart device may comprise a camera, such as the camera 107, which may be directed towards the user, and a display screen, such as display 103.

The otoscope clip device 100 may be attached to smart device 102 by clamping mechanism, such as a screw clamp assembly, that may be driven by knob 114. The knob 114 may cause the screw clamp assembly to close when turned. For example, the knob 114 may cause the screw clamp assembly to close when turned in a clockwise direction. The knob 114 may cause the screw clamp assembly to open when turned. For example, the knob 114 may cause the screw clamp assembly to open when turned in a counterclockwise direction. When the screw clamp assembly is closed, the otoscope clip device 100 may be attached to the smart device 102. When the screw clamp assembly is open, the otoscope clip device 100 may be detached from the smart device 102.

When turned, knob 114 may engage a screw clamp assembly such that the screw clamp assembly may close. The knob 114 may cause a piston that may include alignment tab 106 to move towards a surface that is parallel to alignment tab 106. For example, knob 114 may cause the alignment tab 106 to move towards clip engagement member 118 such that the alignment tab 106 may come in contact with a display of smart device 102, and clip engagement member 118 may come in contact with the back side of smart device 102. The alignment tab 106 and/or the engagement member may include a surface that may come in contact with the display 103. The surface of the alignment tab 106 may be made of a material that may be an anti-scratch and/or anti-skid.

Otoscope clip device 100 may be attached to smart device 102 in such a way as to avoid compressing and/or contacting one or more buttons of smart device 102. Otoscope clip device 100 may attach to smart device 102, such that otoscope clip device 100 may contact one or more of a front face, a back face, and a top portion of smart device 102. Otoscope clip device 100 may be attached in such a way as to avoid contacting the sim card cover 124, the button 105, the volume button 116, and the switch 130 (the volume button 116 and the switch 130 may be shown with respect to FIG. 1D) of the smart device 102.

As shown in FIG. 1C, alignment tab 106 may be aligned with alignment image 104. For example, alignment tab 106 may cover alignment image 104. Alignment tab 106 may cover alignment image 104 such that alignment tab 106 may remain within the edges of alignment image 104.

When alignment tab 106 may be within and/or aligned with alignment image 104, the otoscope assembly 120 of otoscope clip device 100 may be aligned with smart device camera 112.

As shown in FIG. 1D, the otoscope assembly 120, the viewing portion 108 of the otoscope, and/or the outer tip housing 110 may be aligned with the smart device camera 112. The otoscope assembly 120 may be aligned with the smart device camera 112 in such a way that a user may place the otoscope with speculum in an ear of a patient and may take a photo of the outer ear, middle ear, and/or ear canal of the patient. For example, the smart device camera 112 may be able to use the otoscope assembly 120 to view an outer ear, a middle ear, and/or an ear canal of a patient via a sight path that may be established through the viewing portion 108 of the otoscope and through an opening in the outer tip housing 110 and through the attached speculum.

Figure 2:
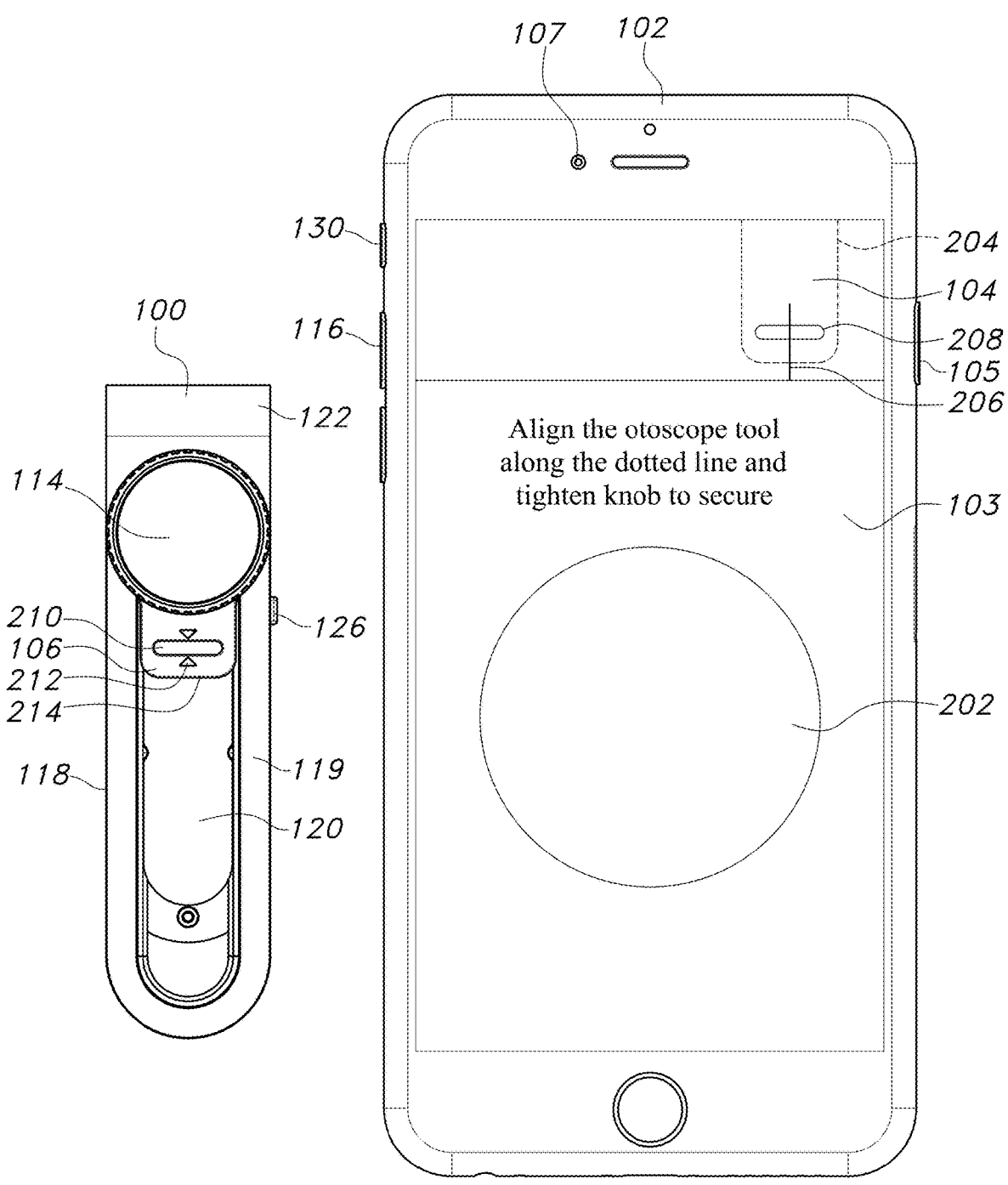
FIG. 2 depicts a perspective view of an otoscope clip device that comprises an alignment tab and a smart device that may comprise a screen that displays an alignment image.

FIG. 2 depicts a perspective view of an otoscope clip device that comprises an alignment tab and a smart device that may comprise a screen that displays and alignment image.

The smart device 102 may comprise a one or more buttons and/or switches. For example, the smart device 102 may comprise the switch 130, the volume buttons 116, and the button 105. The smart device may include a camera, such as the camera 107, which may face a user. The smart device may include a display, such as the display 103.

The display 103 may provide instructions to a user as to how to align the otoscope clip device 100. The display 103 may include image 202, which may be an image taken from the smart device camera. When the otoscope clip device 100 may be attached to the smart device 102 an image may be taken. For example, an image may be taken through an otoscope. For example, the otoscope clip device 100 may include the otoscope assembly 120. When otoscope clip device 100 is attached to smart device 102, the otoscope assembly 120 may be aligned with a smart device camera, and an image or video may be taken through the otoscope associated with the otoscope assembly 120.

The display 103 may display the alignment image 104. The alignment image 104 may be used to assist a user in aligning and otoscope with a smart device camera when the user is attaching the otoscope clip device 100 to smart device 102. The alignment image 104 may depict a shape that may be similar and/or complementary to alignment tab 106 of the otoscope clip device 100. When the alignment tab 106 may be placed within alignment image 104, an otoscope associated with the otoscope assembly 120 may be aligned and/or may be in contact with a smart device camera.

The alignment image 104 may include a number of features that may assist in aligning the alignment image 104 with the alignment tab 106 and/or the otoscope associated with the otoscope assembly 120. These features may include a shape of the alignment image 104, the color of the alignment image 104, a shape within the alignment image 104, an object within the alignment image 104, a color within the alignment image 104, a combination thereof, and/or the like. The alignment image 104 may include the alignment image outline 204, the horizontal alignment image feature 206, the vertical alignment image feature 208, a combination thereof, and/or the like.

The alignment image 104 may be used by a user to determine how to move the otoscope clip device 100 to achieve alignment. The alignment image 104 may be used by the user to determine how to move the otoscope clip device 100 in an axis associated with a plane created by the display 103. For example, the display 103 may have a horizontal axis that may cross a first side of the smart device 102 that may include the volume button 116 to a second side of smart device 102 that may include the button 105. The display 103 may have a vertical axis that may be orthogonal to the horizontal axis. The alignment image 104 may provide a user with visual feedback as to how to move the otoscope clip device 100 in the vertical axis and/or the horizontal axis of the display 103, which may align the otoscope with a smart device camera.

The alignment image outline 204 may allow user to align the alignment tab 106 of the otoscope clip device 100 such that the otoscope associated with the otoscope assembly 120 may be aligned with the smart device camera. The user may use the alignment image outline 204 to align the alignment tab 106 in the vertical axis and/or the horizontal axis of the display 103. For example, the user may place the alignment tab 106 on, near, or within the alignment image outline 204 to achieve alignment. If the otoscope is misaligned with the smart device camera, a portion of the alignment tab 106 may appear outside the alignment image outline 204. The user may adjust the otoscope clip device 100 to address the portion of the alignment tab 106 that may be outside the alignment image outline 204 and may align the otoscope with the device camera. By correcting the misalignment of the alignment tab 106 with the alignment image outline 204, the user may correct the alignment of the otoscope with the smart device camera.

The alignment image outline 204 may be larger (e.g., slightly larger) than the alignment tab 106 such that alignment tab 106 may fit within the alignment image 104, and the alignment image outline 204 may be seen. The alignment image outline 204 may be the same or of a similar color to alignment image 104, the alignment tab 106, and/or the alignment tab edge 214. The alignment image outline 204 may be a different color than the alignment image 104, the alignment tab 106, and/or the alignment tab edge 214.

The user may use the horizontal alignment image feature 206 to determine how to move the otoscope clip device 100 to achieve alignment. The horizontal alignment image feature 206 may be a line, an object, a shape, an icon, and indicator, and/or the like. For example, the horizontal alignment image feature 206 may be a line elongated in a vertical direction. The horizontal alignment image feature 206 may be within alignment image 104, may be outside alignment image 104, and/or may intersect the alignment image outline 204. The horizontal alignment image feature 206 may be used by a user to determine how to move the otoscope clip device 100 along a horizontal axis associated with the display 103 to horizontally align the otoscope associated with the otoscope assembly 120 with the smart device camera.

To provide guidance as to how to move the otoscope clip device 100 along the horizontal axis, the horizontal alignment image feature 206 may have one or more reference points. For example, the horizontal alignment image feature 206 may be a number of dots along a vertical axis, a line along the vertical axis, a shape elongated along the vertical axis, an indicator along the vertical axis, and/or the like.

To align the otoscope with the smart device camera along the horizontal axis, a user may attach otoscope clip device 100 on smart device 102 such that the horizontal alignment tab feature 212 may be aligned with horizontal alignment image feature 206. For example, the user may align the arrow or triangular protrusions of horizontal alignment tab feature 212 with the line of horizontal alignment image feature 206.

The user may use the vertical alignment image feature 208 to determine how to move the otoscope clip device 100 to achieve alignment. The vertical alignment image feature 208 may be a line, an object, a shape, an indicator, an icon, and/or the like. For example, the vertical alignment image feature 208 may be an oval elongated along the horizontal axis. The vertical alignment image feature 208 may be within alignment image 104, may be outside alignment image 104, and/or may intersect the alignment image outline 204. The vertical alignment image feature 208 may be used by a user to determine how to move the otoscope clip device 100 along the vertical axis associated with the display 103 to vertically align the otoscope associated with the otoscope assembly 120 with the smart device camera.

To provide guidance as to how to move the otoscope clip device 100 along the vertical axis, the vertical alignment image feature 208 may have one or more reference points. For example, the vertical alignment image feature 208 may be a number of dots along a horizontal axis, a line along the horizontal axis, a shape elongated along the horizontal axis, an indicator along the horizontal axis, and/or the like.

To align the otoscope with the smart device camera along the vertical axis, a user may attach otoscope clip device 100 on smart device 102 such that the vertical alignment tab feature 210 may be aligned with vertical alignment image feature 208. For example, the user may align the oval aperture of vertical alignment tab feature 210 with the vertical alignment image feature 208.

Otoscope clip device 100 may comprise the clip assembly 122 and the otoscope assembly 120. The otoscope assembly 120 may include an otoscope and may include a light for the otoscope. The otoscope assembly 120 may include light switch 126 that may control the light for the otoscope. Although a switch is shown with respect to the light switch 126, another suitable element, such as a button, may be used. For example, an On/Off button, a push button, a switch, and/or the like may be used.

The inside portion of the otoscope assembly 120 may be seen in FIG. 2. When otoscope clip device 100 may be attached to smart device 102, the inside portion of otoscope assembly 120 may face and/or contact a back portion of smart device 102 that may include a smart device camera.

The clip assembly 122 may comprise a clamp assembly that may include knob 114. The clip assembly 122 may comprise clip engagement member 118. The clip assembly 122 may comprise alignment tab 106.

The alignment tab 106 may include a number of features that may assist in aligning the alignment tab 106 with the alignment image 104 and/or the otoscope associated with the otoscope assembly 120. These features may include a shape of the alignment tab 106, the color of the alignment tab 106, the shape within the alignment tab 106, an object within the alignment tab 106, a color within the alignment tab 106, a combination thereof, and/or the like. The alignment tab 106 may include the alignment tab edge 214, the horizontal alignment tab feature 212, the vertical alignment tab feature 210, a combination thereof, and/or the like.

The alignment tab 106 may be used by a user as to determine how to move the otoscope clip device 100 to achieve alignment. Alignment tab 106 may be used by a user to determine how to move the otoscope clip device 100 in an axis associated with a plane created by the display 103. For example, display 103 may have a horizontal axis that may cross a first side of smart device 102 that includes volume button 116 to a second side of smart device 102 that includes button 105. Display 103 may have a vertical axis that may be orthogonal to the horizontal axis. The alignment tab 106 may provide a user with feedback as to how to move the otoscope clip device 100 in the vertical axis or the horizontal axis of the display 103, which may align the otoscope with a smart device camera.

The alignment tab edge 214 may allow user to align the alignment tab 106 of the otoscope clip device 100 such that the otoscope associated with the otoscope assembly 120 may be aligned with the smart device camera. The user may use the alignment tab edge 214 to align the alignment tab 106 in the vertical axis and the horizontal axis of the display 103. For example, the user may place the alignment tab edge 214, on, near, or within the alignment image outline 204 and to achieve alignment. If the otoscope is misaligned with the smart device camera, a portion of the alignment tab edge 214 may appear outside the alignment image outline 204. The user may adjust otoscope clip device 100 to address the portion of the alignment tab edge 214 that may be outside the alignment image outline 204 and may align the otoscope with the device camera. By correcting the misalignment of the alignment tab edge 214 with the alignment image outline 204, the user may correct the alignment of the otoscope with the smart device camera.

The alignment tab edge 214 may be an edge of the alignment tab that may be parallel and may be in contact with the phone screen. The alignment tab edge 214 may fit within the alignment image 104 such that the alignment image outline 204 may be seen. The alignment tab edge 214 may be shaped to help reveal the alignment image outline 204, when the alignment tab edge 214 may be placed on top of or over the alignment image outline 204. For example, the alignment tab edge 214 may be created by tapering, chamfering, rounding, or filleting an edge of alignment tab 106. The alignment tab edge 214 may be complementary and/or the same shape as the alignment image outline 204.

The alignment tab edge 214 may be the same color as or a similar color to alignment image 104, the alignment tab 106, and/or the alignment image outline 204. The alignment tab edge 214 may be a different color than the alignment image 104, the alignment tab 106, and/or the alignment image outline 204.

The user may use the horizontal alignment tab feature 212 to determine how to move the otoscope clip device 100 to achieve alignment. The horizontal alignment tab feature 212 may be a line, an object, a shape, an indicator, an icon, an etching, and/or the like. The horizontal alignment tab feature 212 may be a clear portion or a window of the alignment tab 106. The horizontal alignment tab feature 212 may be an oval elongated in the vertical axis. The horizontal alignment tab feature 212 may be a pill shape elongated along the vertical axis.

The horizontal alignment tab feature 212 may be a first arrow-shaped protrusion and a second arrow-shaped protrusion that are placed a distance from each other in a vertical direction. The first arrow-shaped protrusion and the second arrow-shaped protrusion may be designed to point at each other.

In an example, the horizontal alignment tab feature 212 may comprise a first aperture and a second aperture that are a distance from each other. The first aperture and the second aperture may be complementary to one or more objects within the alignment image 104. For example, the first aperture may be aligned with a first circle within the alignment image 104, and the second aperture may be aligned with a second circle within the alignment image 104.

The horizontal alignment tab feature 212 may be aligned with a feature that may be within alignment image 104, may be outside alignment image 104, and/or may intersect the alignment image outline 204. The horizontal alignment tab feature 212 may be used by a user to determine how to move the otoscope clip device 100 along a horizontal axis associated with the display 103 to horizontally align the otoscope associated with the otoscope assembly 120 with the smart device camera.

To provide guidance on how to move the otoscope clip device 100 along the horizontal axis, the horizontal alignment tab feature 212 may have one or more reference points. For example, the horizontal alignment tab feature 212 may be a number of dots along an axis, a line along the axis, a shape elongated along the axis, an indicator along the axis, and/or the like.

To align the otoscope with the smart device camera along the horizontal axis, a user may attach otoscope clip device 100 on smart device 102 such that the horizontal alignment tab feature 212 may be aligned with horizontal alignment image feature 206. For example, the user may align the arrow or triangular protrusions of horizontal alignment tab feature 212 with the line of horizontal alignment image feature 206.

The vertical alignment tab feature 210 may be used by a user to determine how to move the otoscope clip device 100 to achieve alignment. The vertical alignment tab feature 210 may be a line, an object, a shape, an indicator, an icon, an etching, and/or the like. The vertical alignment tab feature 210 may be a clear portion or a window of the alignment tab 106. The vertical alignment tab feature 210 may be an oval elongated along the horizontal axis. The vertical alignment tab feature 210 may be a pill shape elongated along the horizontal axis. The vertical alignment tab feature 210 may align with a feature that may be within the alignment image 104, may be outside the alignment image 104, and/or may intersect the alignment image outline 204. The vertical alignment tab feature 210 may be used a user to determine how to move the otoscope clip device 100 along the vertical axis associated with the display 103 to vertically align the otoscope associated with the otoscope assembly 120 with the smart device camera.

In an example, the vertical alignment tab feature 210 may comprise a first arrow-shaped protrusion and a second arrow-shaped protrusion that are placed a distance from each other in a horizontal direction. The first arrow-shaped protrusion and the second arrow-shaped protrusion may be designed to point at each other.

In another example, the vertical alignment tab feature 210 may comprise a first aperture and a second aperture that are a distance from each other. The first aperture and the second aperture may be complementary to one or more objects within the alignment image 104. For example, the first aperture may be aligned with a first circle within the alignment image 104, and the second aperture may be aligned with a second circle within the alignment image 104.

To provide guidance on moving the otoscope clip device 100 along the vertical axis, the vertical alignment tab feature 210 may be one or more reference points. For example, the vertical alignment tab feature 210 may be a number of dots along an axis, a line along the axis, a shape elongated along the axis, an indicator along the axis, and/or the like.

To align the otoscope with the smart device camera along the vertical axis, a user may attach otoscope clip device 100 on smart device 102 such that the vertical alignment tab feature 210 may be aligned with vertical alignment image feature 208. For example, the user may align the oval aperture of vertical alignment tab feature 210 with the vertical alignment image feature 208.

Figure 3A:
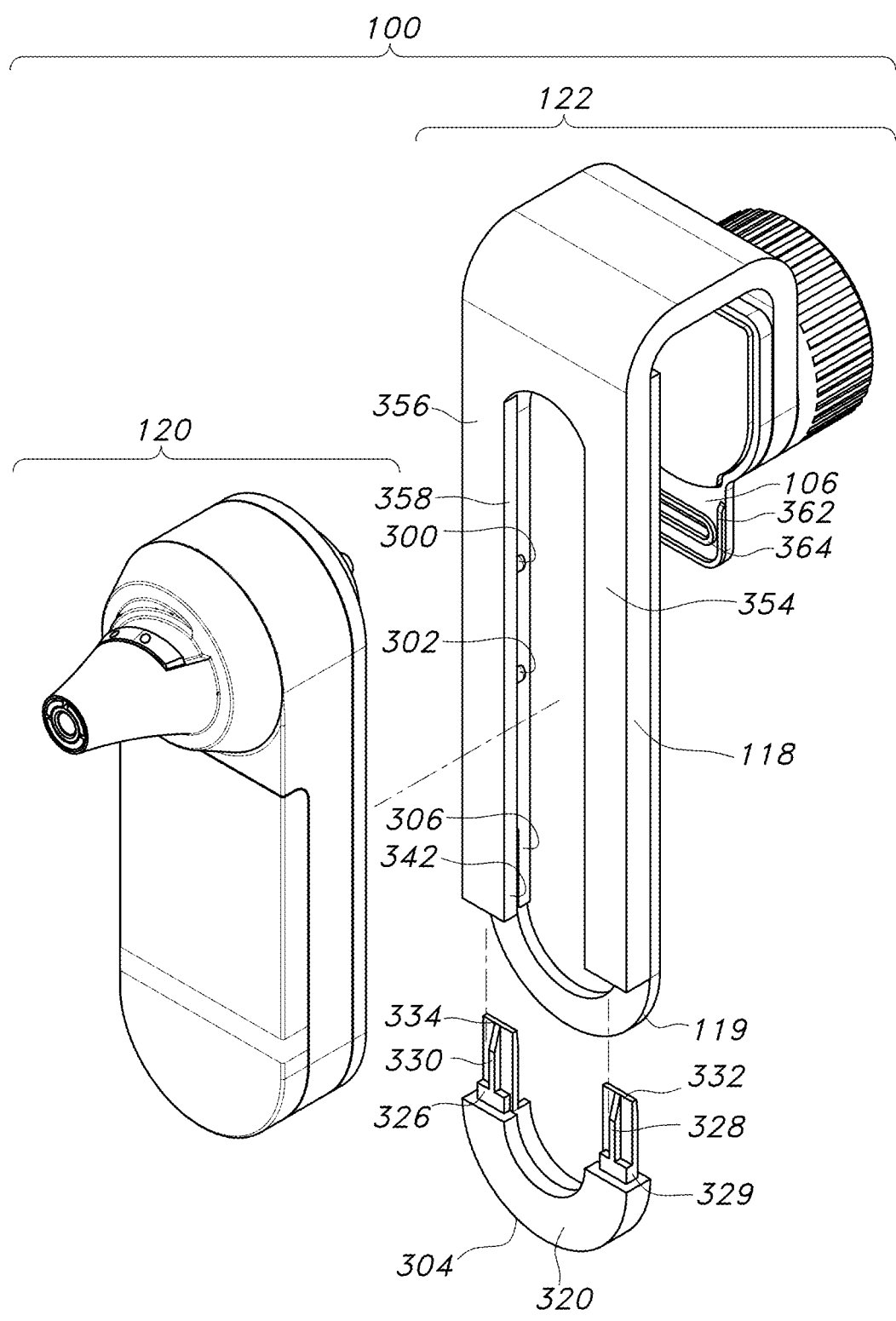
FIGS. 3A-3B depict perspective views of an otoscope clip device that may comprise an otoscope assembly and a clip assembly.
Figure 3B:
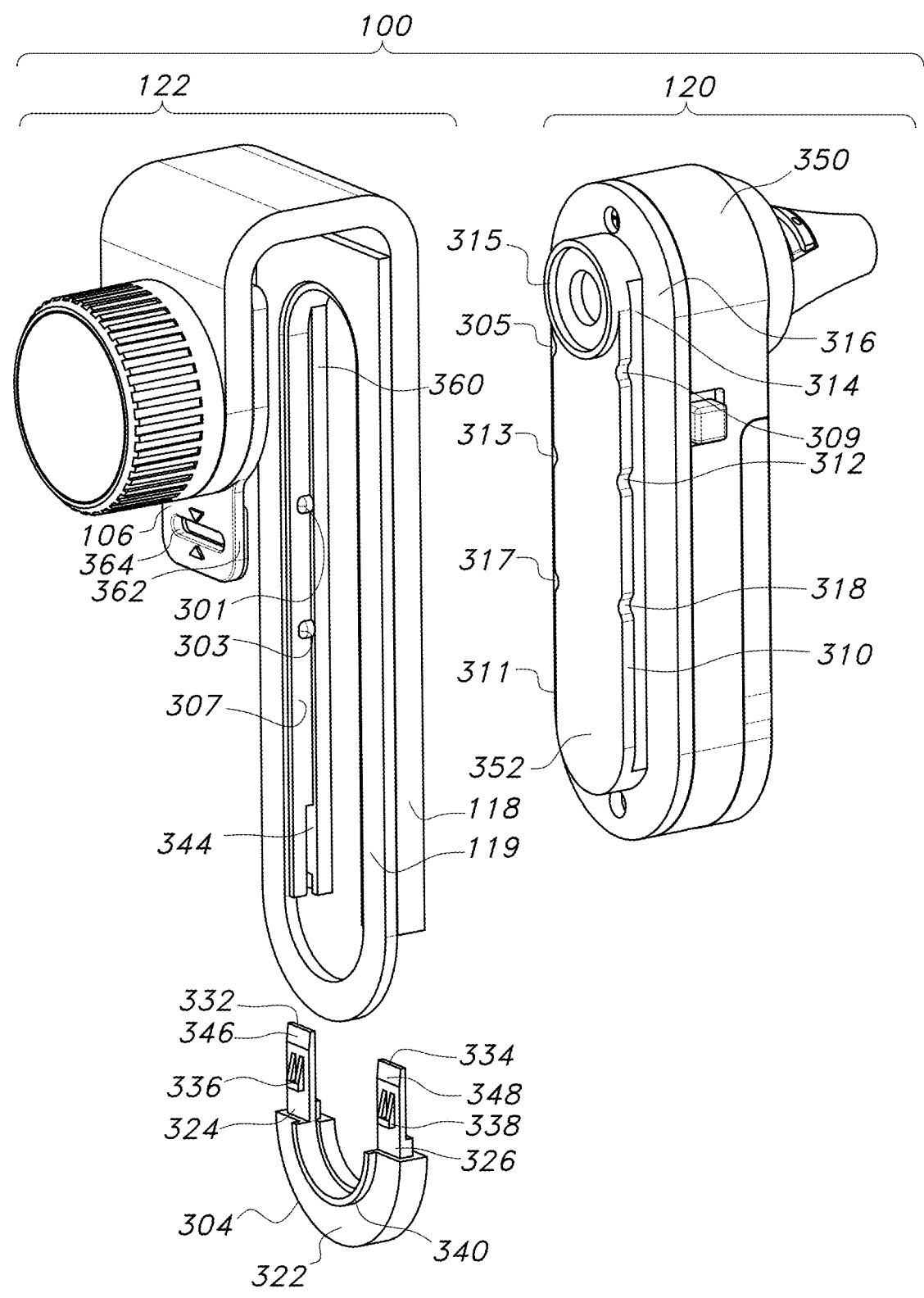

FIGS. 3A-B depict perspective views of an otoscope clip device that may comprise an otoscope assembly and a clip assembly. FIG. 3A shows a first perspective of the otoscope clip device 100. FIG. 3B shows a second perspective of the otoscope clip device 100. As shown in FIGS. 3A-B, the otoscope clip device 100 may comprise otoscope assembly 120, and clip assembly 122.

The otoscope assembly 120 may comprise the main body 350, the otoscope back-plate 316, and the otoscope engagement member 352. The otoscope back-plate 316 may be connected to the main body 350. The otoscope engagement member 352 may be connected to the clip assembly 122. For example, the otoscope engagement member 352 may allow the otoscope assembly 120 to attach to, connect to, or engage with the clip engagement member 118 of the otoscope clip device 100.

The otoscope engagement member 352 may comprise a guide track, such as guide track 314 and guide track 315. The guide track may be a channel formed in the surface of the otoscope engagement member 352 that may face an inner surface of the clip engagement member 118. The guide track may be a channel in the surface of the otoscope engagement member 352 that may be orthogonal to the surface of the otoscope back-plate 316. The guide track may be connected to the otoscope back-plate 316 and may be connected to a protruding connecting member, such as protruding connecting member 310 and/or protruding connecting member 311.

The otoscope engagement member 352 may have an undercut in one or more sides that may be orthogonal to the otoscope back-plate 316 such that an overhang may be created. The overhang may be parallel to the otoscope back-plate 316. The undercut may be the guide track 314 and/or the guide track 315. The overhang may be the protruding connecting member 310 and/or the protruding connecting member 311. The overhang may include one or more receiver elements that may be designed to engage with one or latching elements within the channel 306 and/or channel 307. A latching element of the one or more latching elements may be a resilient member, a protrusion, an outwardly extending lug, a key, and/or the like. A receiver element of the one or more receiver elements may be a recess, a cut out, a detent indentation, and/or the like.

The protruding connecting member 310 may include the receiver element 309, which may engage with the latching element 300. The protruding connecting member 310 may include the receiver element 312, which may engage the latching element 300 and/or the latching element 302. The protruding connecting member 310 may include the receiver element 318, which may engage with the latching element 302.

The protruding connecting member 311 may include the receiver element 305, which may engage with the latching element 301. The protruding connecting member 311 may include the receiver element 313, which may engage with the latching element 301 and/or the latching element 303. The protruding connecting member 311 may include the receiver element 317, which may engage with the latching element 303.

The otoscope assembly 120 may be slidably connected to clip assembly 122. The protruding connecting member 310 may slidably connect with channel 306. The protruding connecting member 311 may slidably connect with channel 307. The clip engagement member lip 360 may slidably connect with guide track 315. The clip engagement member lip 358 may slidably connect with guide track 314. The front surface of engagement member leg 356 and the front surface of engagement member leg 354 may slidably connect with the otoscope back-plate 316.

The clip assembly 122 may comprise the clip engagement member 118 and the end cap 304. The clip engagement member 118 may comprise a pair of legs extending from the ends of a connecting yolk portion that extends perpendicularly to the pair of legs. A leg (e.g., each leg) may comprise a recess at the distal end of the leg, such as the engagement member leg recess 342 and the engagement member leg recess 344, which may allow the end cap 304 to connect with and/or attach to the clip engagement member 118. A leg (e.g., each leg) may comprise a channel, such as the channel 306 and the channel 307, that cuts into a side of the leg that faces the opposing leg. The channel 307 may face the opposing leg. The channel 307 may face the channel 306. The channel 307 may form a track that may engage with the protruding connecting member 311 from the otoscope assembly 120. The channel 307 may engage with the protruding connecting member 311 from otoscope assembly 120 such that clip assembly 122 may be movably connected, attached to, or engaged with clip engagement member 118 and/or clip assembly 122. For example, the channel 307 may allow the protruding connecting member 311 to move slidably within the channel 307 while engaging with the protruding connecting member 311 such that the clip assembly 122 may remain in contact with the otoscope assembly 120.

The channel 307 may include one or more latching elements. For example, the channel 307 may include the latching element 301 and/or the latching element 303. The latching element 301 and/or the latching element 303 may be a resilient member, a protrusion, an outwardly extending lug, a key, and/or the like.

The latching element 301 and/or the latching element 303 may be protrusions or outwardly extending lugs that may be received by a recess, such as a detent indentation or a radial recess, which may be provided by the protruding connecting member 311, such as the receiver element 305, the receiver element 313, and/or the receiver element 317. A receiver element, such as the receiver element 305, the receiver element 313, and/or the receiver element 317, may be a recess, a cut out, a detent indentation, and/or the like.

In a first position, the latching element 301 may resiliently deform a surface of the protruding connecting member 311 and/or may engage with the receiver element 313, for example, in a snap-fit. The latching element 303 may resiliently deform a surface of the protruding connecting member 311 and/or may engage with the receiver element 317, for example, in a snap-fit.

In a second position, the latching element 301 may resiliently deform a surface of the protruding connecting member 311 and/or may engage with the receiver element 305, for example, in a snap-fit. The latching element 303 may resiliently deform a surface of the protruding connecting member 311 and/or may engage with the receiver element 313, for example, in a snap-fit.

The channel 306 may face the opposing leg. The channel 306 may face the channel 307. The channel 306 may form a track that may engage with the protruding connecting member 310 from the otoscope assembly 120. The channel 306 may engage with the protruding connecting member 310 from otoscope assembly 120 such that clip assembly 122 may be movably connected, attached to, or engaged with the clip engagement member 118 and/or the clip assembly 122. For example, the channel 306 may allow the protruding connecting member 310 to move slidably within the channel 306 while engaging with the protruding connecting member 310 such that the clip assembly 122 may remain in contact with the otoscope assembly 120.

The channel 306 may include one or more latching elements. For example, the channel 306 may include the latching element 300 and/or the latching element 302. The latching element 300 and/or the latching element 302 may be a resilient member, a protrusion, an outwardly extending lug, a key, and/or the like.

The latching element 300 and/or the latching element 302 may be protrusions or outwardly extending lugs that may be received by a recess, such as a detent indentation or a radial recess, provided by protruding connecting member 310, such as the receiver element 309, the receiver element 312, and/or receiver element 318. A receiver element, such as the receiver element 309, the receiver element 312, and/or the receiver element 318, may be a recess, a cut out, a detent indentation, and/or the like.

In a first position, the latching element 300 may resiliently deform a surface of the protruding connecting member 310 and/or may engage with the receiver element 312, for example, in a snap-fit. The latching element 302 may resiliently deform a surface of the protruding connecting member and/or may engage with the receiver element 318.

In a second position, the latching element 300 may resiliently deform a surface of the protruding connecting member 310 and/or may engage with the receiver element 309. The latching element 302 may resiliently deform a surface of the protruding connecting member 310 and/or may engage with receiver element 312, for example, in a snap-fit.

The clip assembly 122 may comprise a contact surface 119. The contact surface 119 may be attached to a face of the clip engagement member 118, such as the face of the clip engagement member 118 that may be directed to a surface of the smart device that includes the camera. The contact surface 119 may be of an oval shape that may complement the clip engagement member 118. The contact surface 119 may have an elongated aperture. The elongated aperture may match a complementary aperture in clip engagement member 118. The elongated aperture may allow a viewing portion of the otoscope assembly 120 to go through the contact surface 119. The contact surface 119 may be made of a resilient material that may absorb and/or apply pressure to a surface of the smartphone device. The contact surface 119 may be made of an anti-slip material that may prevent the otoscope clip device 100 from moving when clamped to a smartphone device. The contact surface 119 may be made of a material that avoids damage and/or scratches to the smartphone device. For example, the contact surface may be made of rubber, plastic, a polymer, and/or the like. The contact surface 119 may act as a light block to prevent light from leaking from the otoscope clip device, may prevent light from entering the otoscope clip device optics, and/or may act as a light block to prevent light from entering a camera of the smart device.

The clip assembly 122 may comprise the end cap 304. The end cap 304 may be a u-shaped member with a pair of legs, such as the end cap leg 332 and the end cap leg 334, extending from the ends of the curved center portion. The end cap 304 may be located at the proximal end of the clip engagement member 118. The end cap 304 may comprise a front surface 320 and back surface 322. When the otoscope clip device 100 is attached to a smart device, the front surface 320 many face the otoscope assembly 120, and the back surface 322 may face a surface of the smart device.

The end cap leg 332 may contact the u-shaped portion of end cap 304. The distal end of end cap leg 332 may be beveled at beveled portion 346. The end cap leg 332 may comprise the base end 324 that may be located at the proximal end of the end cap leg 332. The base end 324 may contact the u-shape portion of end cap 304. The base end 324 may be a smaller complementary shape to a cross-section of the u-shape portion of the end cap 304, such that a shoulder may be formed at one or more surfaces that may contact the proximal end of the base end 324. The shoulder may be orthogonal to the base end 324.

The end cap leg 332 may include the spine 328. The spine 328 may be raised from a surface of the end cap leg 332. The spine 328 may contact the base end 324 and may extend towards the distal end of end cap 304. Spine 328 may have a beveled distal end. The spine 328 may have a length that may terminate at the distal end of the end cap 304 and may have a width that may be less than the width of the end cap 304. The spine 328 may be resilient and may provide a bias toward the back surface 322 to allow the end cap foot 336 to engage the engagement member leg recess 344.

The end cap leg 332 may include the end cap foot 336. The end cap foot 336 may be a projecting foot positioned near the distal end of the end cap leg 332. The end cap foot 336 may be an outwardly projecting lug and may be resilient. The end cap foot 336 may connect with a hole, recess, or cut out near the distal end of a leg of the clip engagement member 118. For example, the end cap foot 336 may connect with the engagement member leg recess 344. The engagement member leg recess 344 may be a cut out in a wall or surface of the engagement member leg recess 344 that may be orthogonal to a surface of end cap leg 332 from which end cap foot 336 may protrude.

The end cap leg 334 may contact the u-shaped portion of end cap 304. The distal end of end cap leg 334 may be beveled at beveled portion 348. The end cap leg 334 may comprise the base end 326 that may be located at the proximal end of the end cap leg 334. The base end 326 may contact the u-shape portion of the end cap 304. The base end 326 may be a smaller complementary shape to a cross-section of the u-shape portion of the end cap 304, such that a shoulder may be formed at one or more surfaces that may connect to the proximal end of base end 326. The shoulder may be orthogonal to base end 326. The end cap leg 334 may include the spine 330.

The spine 330 may be raised from a surface of the end cap leg 334. The spine 330 may contact the base end 326 and may extend towards the distal end of the end cap 304. The spine 330 may have a beveled distal end. The spine 330 may have a length that may terminate at the distal end of the end cap 304 and may have a width that may be less than the width of end cap 304. The spine 330 may be resilient and may provide a bias toward the back surface 322 to allow end cap foot 338 to engage the engagement member leg recess 344.

The end cap leg 334 may include the end cap foot 338. The end cap foot 338 may be a projecting foot positioned near the distal end of the end cap leg 334. The end cap foot 338 may be an outwardly projecting lug and may be resilient. The end cap foot 338 may connect with a hole, recess, or cut out near the distal end of a leg of the clip engagement member 118. For example, the end cap foot 338 may connect with the engagement member leg recess 342. The engagement member leg recess 342 may be a cut out in a wall or surface of the clip engagement member 118 that may be orthogonal to a surface of the end cap leg 334 from which the end cap foot 338 may protrude.

When connected to clip engagement member 118, the end cap 304 may prevent the otoscope assembly 120 from moving beyond a position and/or disengaging with the clip assembly 122. For example, the end cap 304 may prevent a user from accidentally moving the otoscope assembly 120 beyond a point to cause damage to the otoscope assembly 120.

To assemble otoscope clip device 100, the otoscope assembly 120 may be slid into the clip assembly 122, and the end cap 304 may be connected to the clip engagement member 118 to retain otoscope assembly 120 within the clip assembly 122. The otoscope assembly 120 may slidably connect with clip assembly 122. For example, the protruding connecting member 310 may slide into the channel 306, the protruding connecting member may slide into the channel 307, the clip engagement member lip 360 may slide into the guide track 315, and the clip engagement member lip 358 may slide into the guide track 314.

Figure 4A:
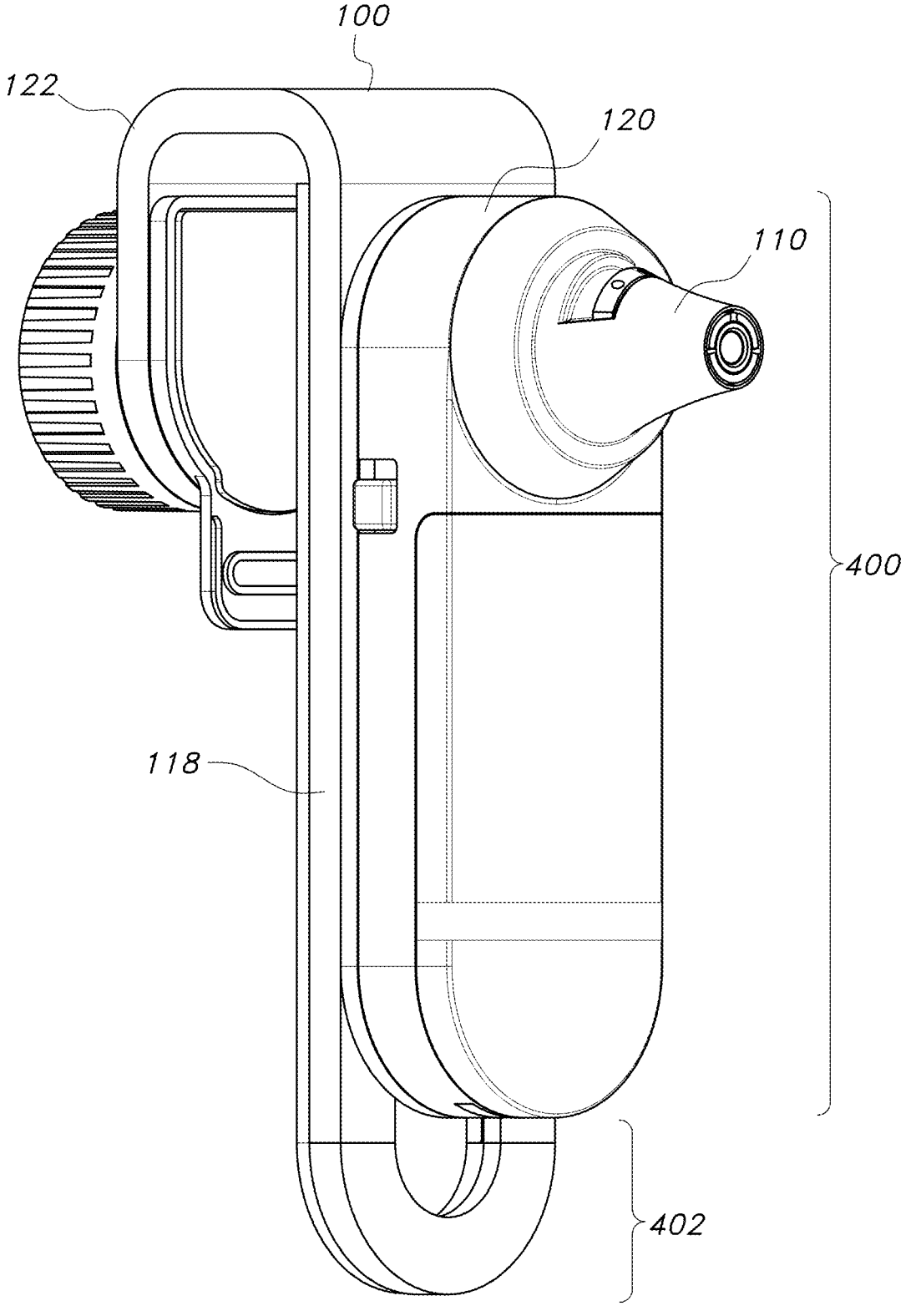
FIGS. 4A-4C depict perspective views of an example otoscope clip device where the otoscope assembly is in a first position, which may be an upper position, within a clip assembly.
Figure 4B:
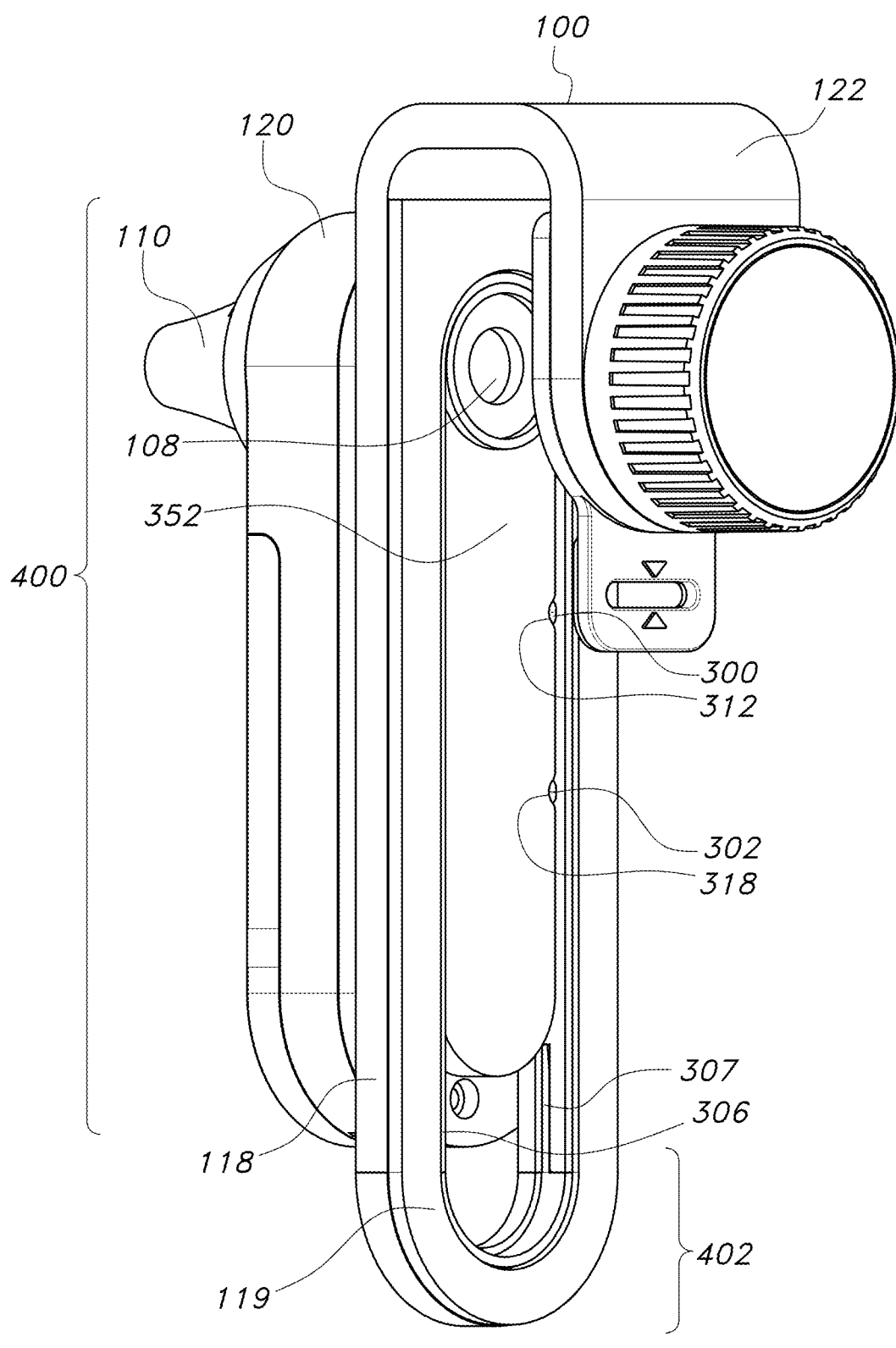
Figure 4C:
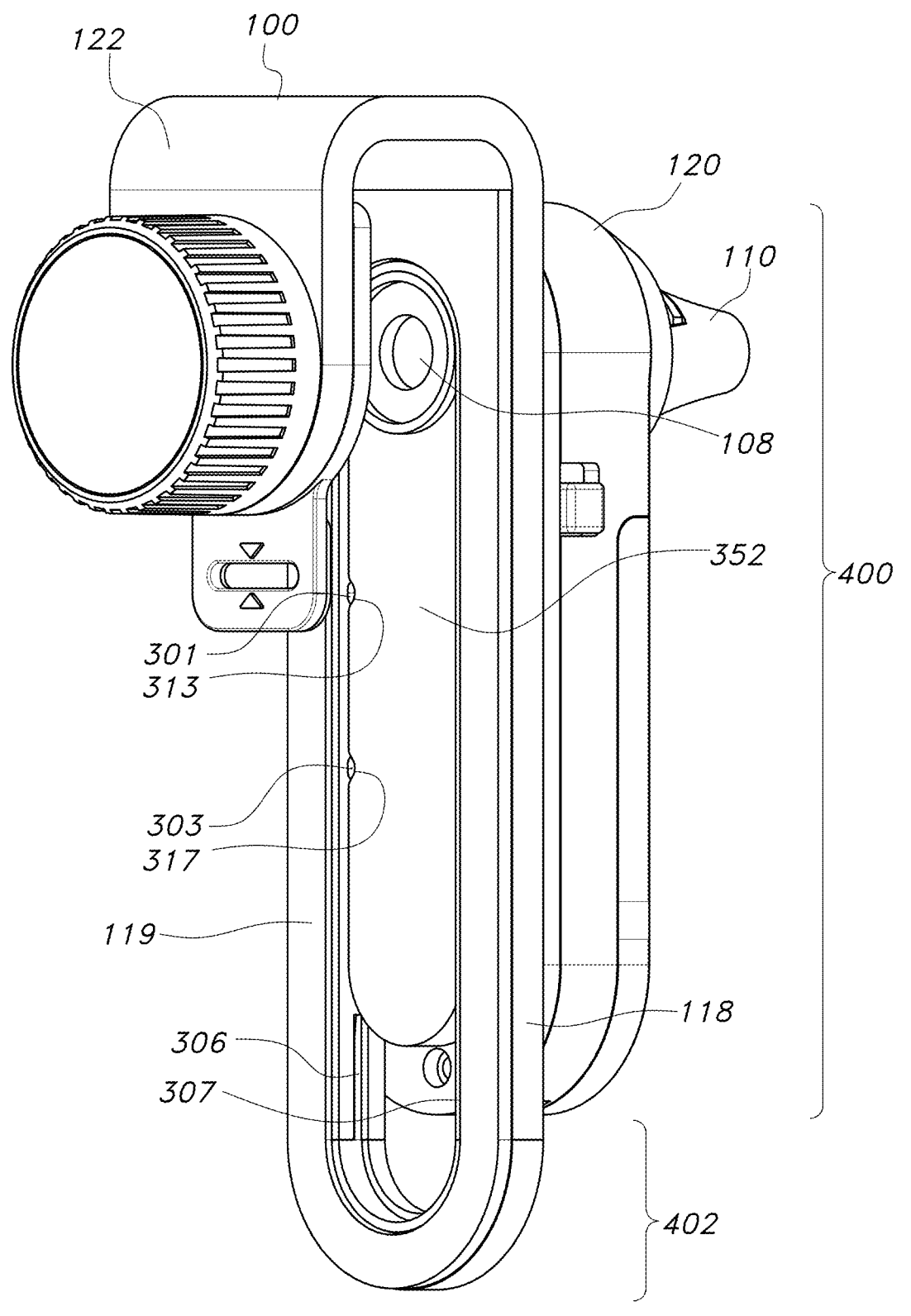

FIGS. 4A-C depict perspective views of an example otoscope clip device where the otoscope assembly is in a first position, which may be an upper position, within a clip assembly.

Different smart devices may include a camera in different positions and/or locations. For example, a first smart device may have a camera located a distance (e.g., a length) from a distal end of the first smart device. A second smart device may have a camera located a distance (e.g., a length) from a distal end of the second smart device that may be twice as long as the distance (e.g., the length) for the first smart device.

To account for the differences in length, the otoscope clip device 100 may be adjustable. For example, the otoscope clip device 100 may allow the otoscope assembly 120 to be placed in one or more locations and/or positions within the clip assembly 122. As shown in FIGS. 4A-C, the otoscope clip device 100 may comprise the clip assembly 122 and the otoscope assembly 120. The otoscope assembly 120 may be slidably movable within the clip assembly 122. The otoscope assembly 120 may be slidably movable within the clip assembly 122 to assist in aligning the viewing portion 108 of the otoscope assembly with a smart device.

The otoscope assembly 120 may be in a first position, which may be the upper position 400, within the clip assembly 122. The upper position 400 may be an upper position within the clip assembly 122. For example, the upper position 400 may be a position where the otoscope assembly 120 may be near the proximal end of the clip engagement member 118. A user may place the otoscope assembly 120 in the upper position 400 by sliding otoscope assembly 120 toward the proximal end of the clip engagement member 118. When the otoscope assembly 120 is at the upper position 400, the otoscope engagement member 352 may create a gap in the lower portion, such as the clip engagement member gap 402.

When the otoscope assembly 120 may be in the first position, the viewing portion 108, and/or the outer tip housing 110 may be aligned with the camera of the smart device. The otoscope assembly 120 may move or slide to the upper position 400 when the otoscope engagement member 352 slides toward the proximal end of the clip engagement member 118, for example, using the channel 306 and the channel 307. The otoscope assembly 120 may maintain the upper position 400 by being slidably connected to the clip engagement member 118. The otoscope assembly 120 may be slidably connected to the clip engagement member 118 at the upper position 400 via the latching element 300 being engaged to the receiver element 312, the latching element 302 being engaged to the receiver element 318, the latching element 301 being engaged to the receiver element 313, and/or the latching element 303 being engaged to the receiver element 317.

In the upper position 400, the otoscope assembly 120 may not use one or more latching elements. The otoscope engagement member 352 may not use one or more latching elements provided by the channel 306 and/or the channel 307. For example, the receiver element 305 and/or the receiver element 309 may not be engaged with a latching element.

Figure 5A:
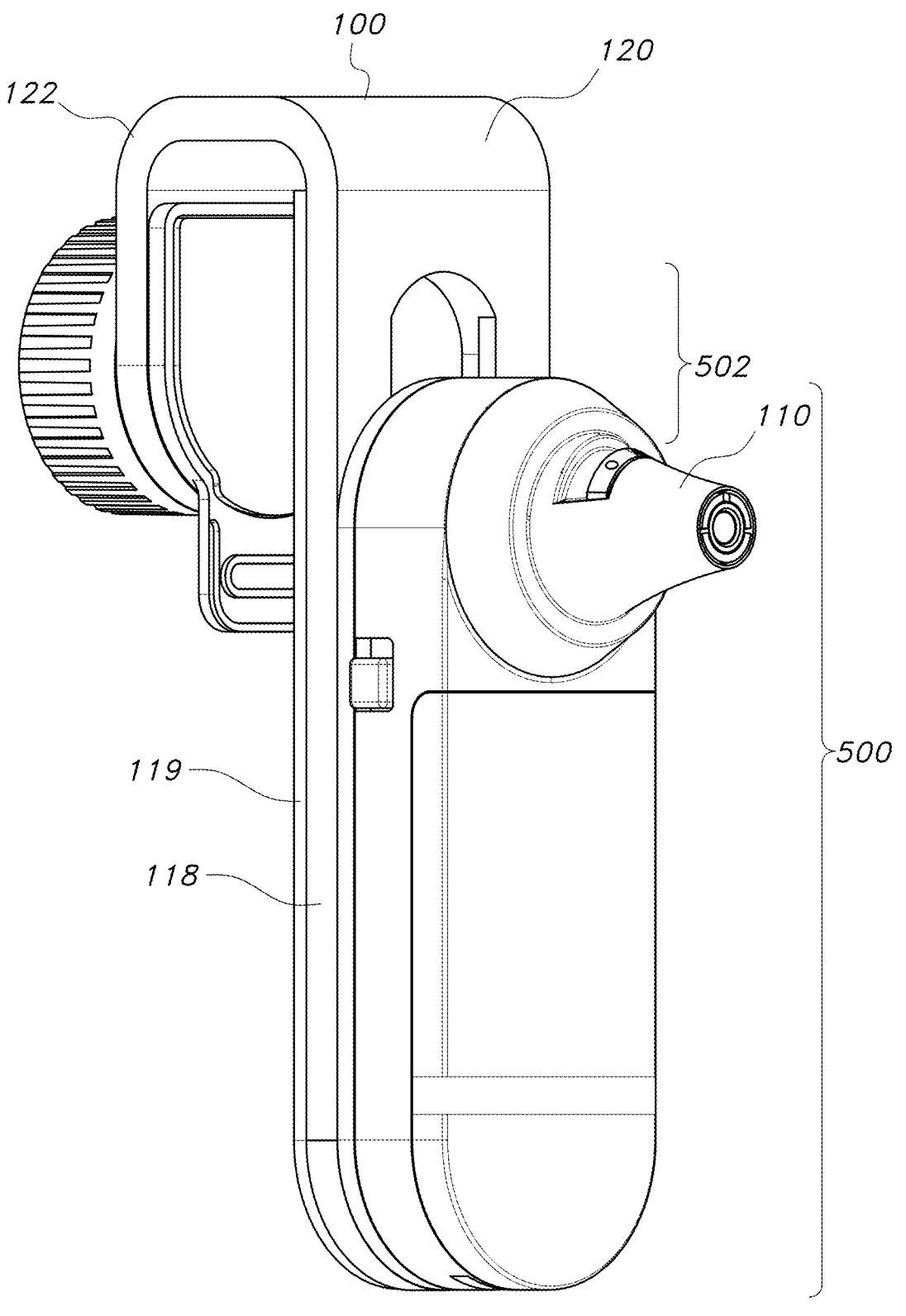
FIGS. 5A-5C depict perspective views of an example otoscope clip device where the otoscope assembly is in a second position, which may be a lower position, within a clip assembly.
Figure 5B:
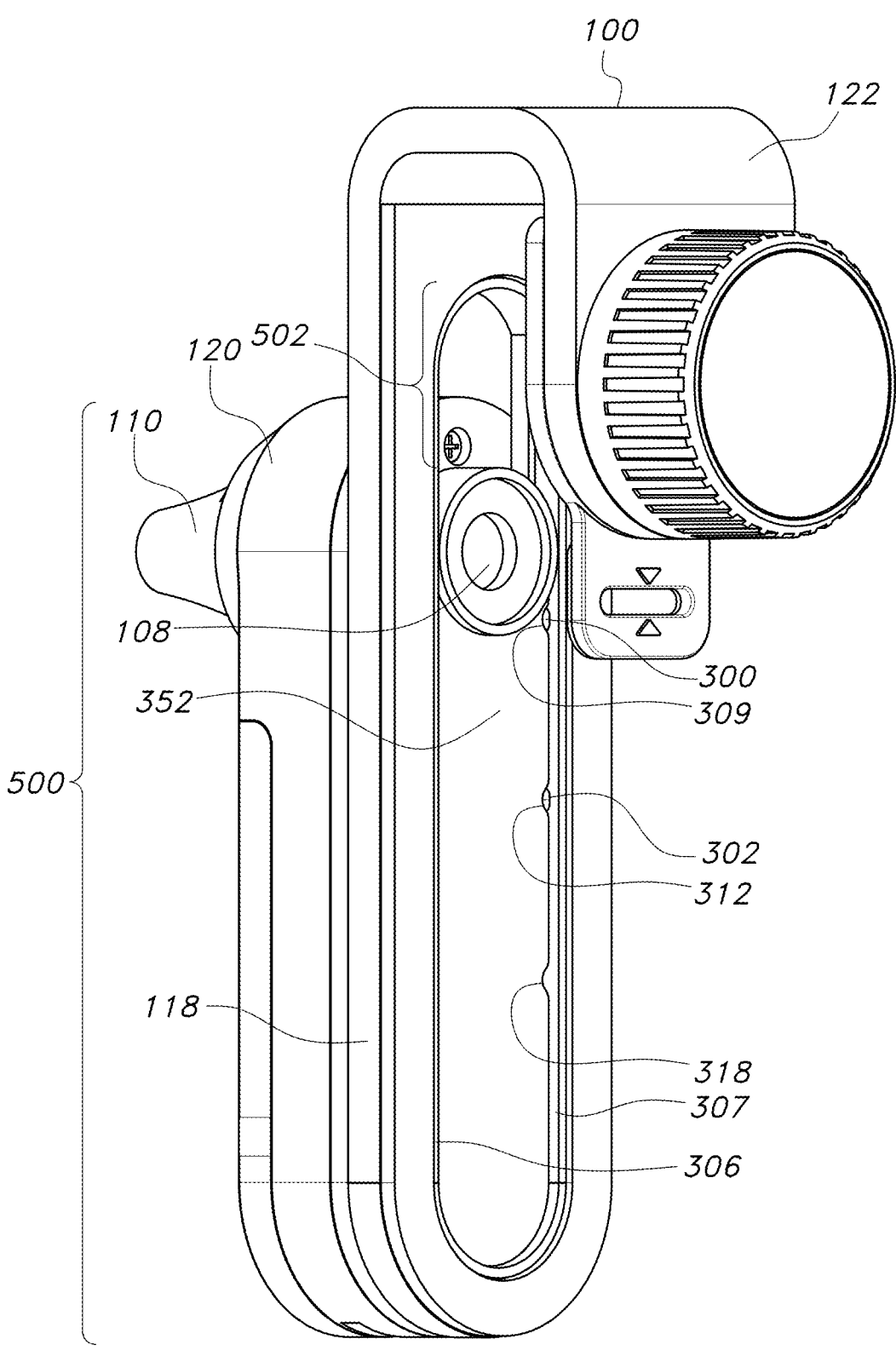
Figure 5C:
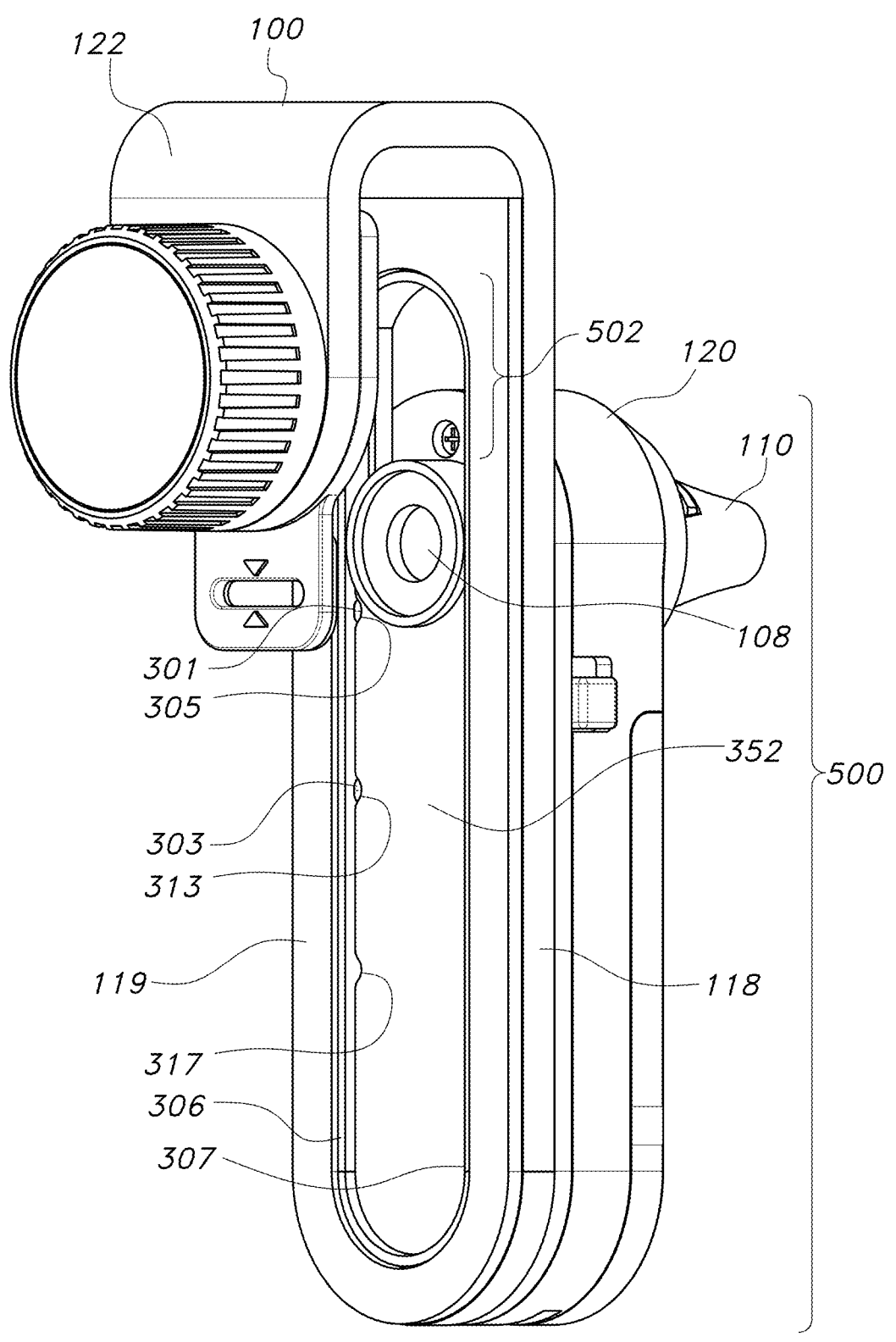

FIGS. 5A-C depict perspective views of an example otoscope clip device where the otoscope assembly is in a second position, which may be a lower position, within a clip assembly. To account for the differences in length, the otoscope clip device 100 may be adjustable. For example, the otoscope clip device 100 may allow the otoscope assembly 120 to be placed in one or more locations and/or positions within the clip assembly 122. As shown in FIGS. 5A-C, the otoscope clip device 100 may comprise the clip assembly 122 and the otoscope assembly 120. The otoscope assembly 120 may be slidably movable within clip assembly 122. The otoscope assembly 120 may be slidably movable within clip assembly 122 to assist in aligning the viewing portion 108 of the otoscope assembly with a smart device.

The otoscope assembly 120 may be in a second position, which may be the lower position 500, within the clip assembly 122. The lower position 500 may be a lower position within the clip assembly 122. For example, the lower position 500 may be a position where the otoscope assembly 120 may be near the proximal end of the clip engagement member 118. A user may place the otoscope assembly 120 in the lower position 500 by sliding otoscope assembly 120 toward the proximal end of the clip engagement member 118. When the otoscope assembly 120 is at the lower position 500, the otoscope engagement member 352 may create a gap in the upper portion such as the clip engagement member gap 502.

When the otoscope assembly 120 may be in the second position, the viewing portion 108 and/or the outer tip housing 110 may be aligned with the camera of the smart device.

The otoscope assembly 120 may move or slide to the lower position 500 when otoscope engagement member 352 slides toward the distal end of the clip engagement member 118, for example, using the channel 306 and the channel 307.

The otoscope assembly 120 may maintain the lower position 500 by being slidably connected to the clip engagement member 118. The otoscope assembly 120 may be slidably connected to the clip engagement member 118 at the position 500 via the latching element 302 being engaged to the receiver element 312, the latching element 300 being engaged to the receiver element 309, the latching element 303 being engaged to the receiver element 313, and the latching element 301 being engaged to the receiver element 305.

In the lower position 500, the otoscope assembly 120 may not use one or more available latching elements. The otoscope engagement member 352 may not use one or more latching elements provided by the channel 306 and/or the channel 307. For example, the receiver element 317 and/or the receiver element 318 may not be engaged with a latching element.

Figure 6:
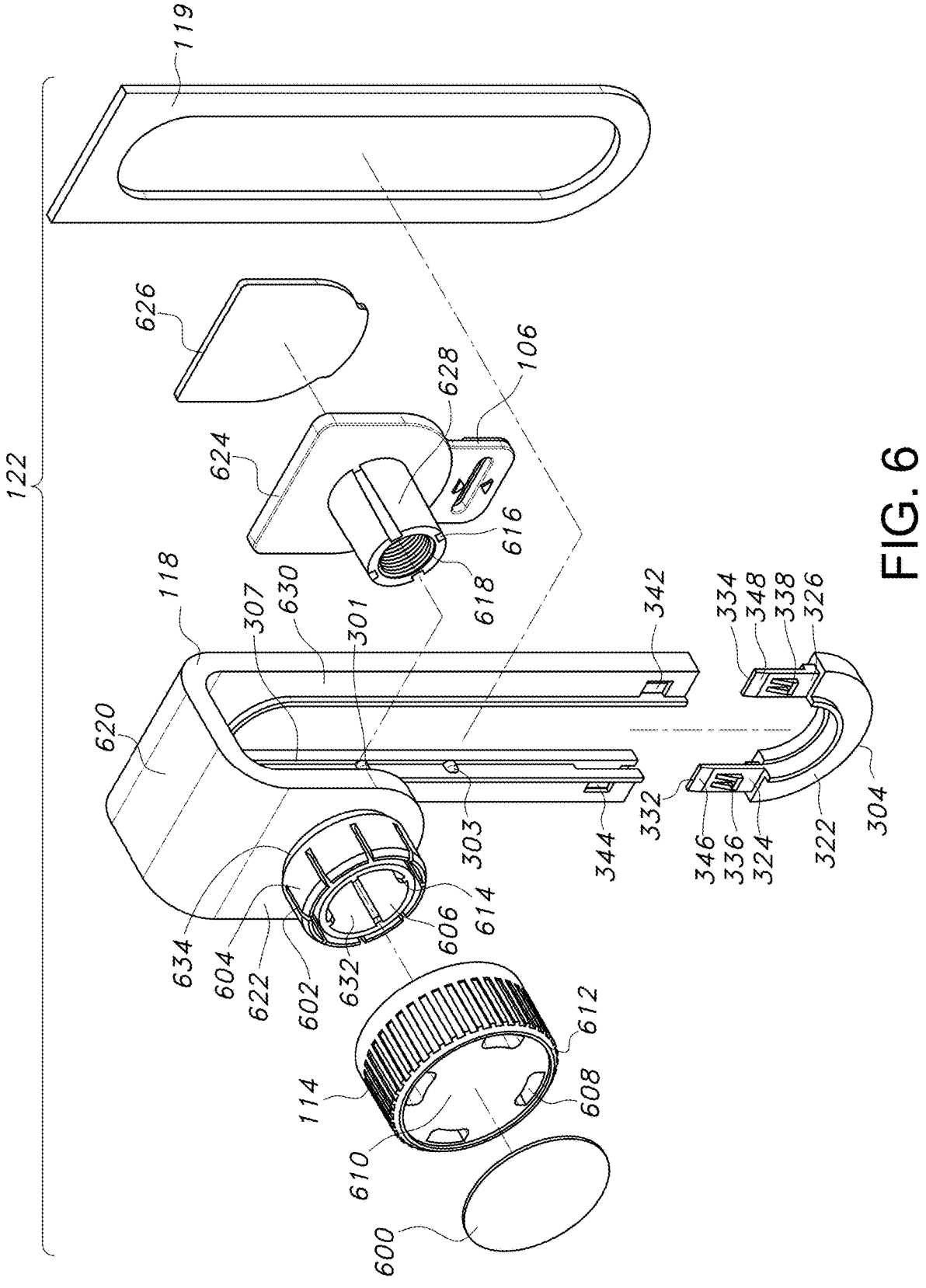
FIG. 6 depicts a schematic view a clip assembly that may comprise one or more components.

FIG. 6 depicts a schematic view of a clip assembly that may comprise one or more components. As shown in FIG. 6, the clip assembly 122 may comprise the clip engagement member 118, the connecting member 620, and the screw clamp assembly 622.

The clip engagement member 118 may comprise one or more channels that may allow for engagement and/or attachment with an otoscope engagement member. For example, the clip engagement member 118 may comprise the channel 307. The channel 307 may comprise the latching element 301 and the latching element 303. The latching element 301 and the latching element 303 may be a resilient lug or protrusion that may resiliently contact a recess that may belong to the otoscope engagement member. The clip engagement member 118 may include the engagement member leg recess 342 and the engagement member leg recess 344.

The clip engagement member 118 may comprise the end cap 304. The end cap 304 may comprise a front surface and a back surface, such as the back surface 322. The end cap 304 may comprise the end cap leg 332 and the end cap leg 334. The end cap leg 332 may comprise the beveled portion 346 that may be at the distal end of the end cap leg 332, the end cap foot 336, and the base end 324 that may be at the proximal end of the end cap leg 332. The end cap leg 334 may comprise the beveled portion 348 that may be at the distal end of the end cap leg 334, the end cap foot 338, and the base end 326 that may be at the proximal end of the end cap leg 334. The end cap 304 may be connected to the clip engagement member 118 via the end cap foot 336 engaging with engagement member leg recess 344 and end cap foot 338 engaging with the engagement member leg recess 342.

The clip engagement member 118 may comprise the inner surface 630. The inner surface 630 may be in contact with contact surface 119. The contact surface 119 may have an aperture that may be elongated to match the aperture formed within the clip engagement member 118. The contact surface 119 may be made of material that may prevent slipping, for example, when the clip assembly 122 may be attached to a smart device. The contact surface 119 may be made of a material that may prevent and/or avoid damage to a surface of a smart device. For example, the material of contact surface 119 may be in contact with the surface of a smartphone device and may prevent scratching, chipping, or other damage to surface of the smartphone device.

The connecting member 620 may be connected to the clip engagement member 118 and may be connected to the screw clamp assembly 622. The connecting member 620 may be connected to the clip engagement member 118 such that the connecting member 620 may be orthogonal to clip engagement member 118. The surfaces at which connecting member 620 may make contact the clip engagement member 118 may be rounded or may have a fillet.

The connecting member 620 may be connected to the screw clamp assembly 622 such that the connecting member 620 may be orthogonal to the screw clamp assembly 622. The surface at which connecting member 620 may contact the screw clamp assembly 622 may be rounded or may have a fillet.

The screw clamp assembly 622 may comprise the piston 624, the outer ring 604, the inner ring 606, the key 614, the aperture 632, and the knob 114. The knob 114 may be cylindrical and may have a textured outer ring which may be splines, knurling, and/or the like. The knob 114 may have a bottom side that faces the screw clamp assembly 622. The bottom side of knob 114 may have a hole that may have an outer ring, a locking ring, and a threaded protrusion in its center. The outer ring of the bottom side of the knob may have a circumference that may be larger than the outer ring 604. The locking ring may be formed at the end of the knob that faces toward the outer ring 604. The locking ring may have a smaller circumference than the outer ring 604. The locking ring may be of a larger circumference than locking groove 634. The locking ring may be resilient such that it may resiliently contact the locking groove 634 such that knob 114 may be movably attached to the screw clamp assembly 622.

The knob 114 may have a topside that may have one or more irregular apertures, such as the aperture 608. The top side of knob 114 may comprise circular surface 610, which may be countersunk such that a lip may be formed, such as the circular lip 612. The knob cap 600 may be in contact with circular surface 610. For example, the knob cap 600 may be press fit into the circular surface 610 such that the knob cap 600 be near or flush with the circular lip 612.

The screw clamp assembly 622 may comprise the aperture 632. The aperture 632 may allow a threaded protrusion from knob 114 to contact the piston 624. The aperture 632 may be surrounded by the inner ring 606. For example, the inner ring 606 may contact a circumference of the aperture 632.

The inner ring 606 may contact a surface of the screw clamp assembly 622 that may be parallel to the clip engagement member 118. The inner ring 606 may be a hollow cylinder with an inner surface, an outer surface, and an aperture complementary positioned to the aperture 632. The inner ring 606 may protrude a length orthogonally from a surface of the screw clamp assembly 622. The inner ring 606 may comprise one or more keys that may be located on the inner surface of the inner ring 606. For example, the inner ring 606 may comprise key 614, which may be a complementary shape to keyway 616 on shaft 628 of piston 624.

The outer ring 604 may have a larger circumference than the inner ring 606. The outer ring 604 may be in contact with a surface of the screw clamp assembly 622. The outer ring may protrude a length orthogonally from a surface of the screw clamp assembly 622. The distal end of the outer ring 604 may be chamfered. The outer ring 604 may have one or more notches or kerfs, such as the kerf 602. The kerf 602 may begin at the distal end of the outer ring 604 and may end a length before the proximal end of the outer ring 604. The proximal end of outer ring 604 may be in contact with the locking groove 634.

The locking groove 634 may have a circumference that may be smaller than the outer ring 604. The locking groove 634 may be larger than the circumference of inner ring 606. The locking groove 634 may be in contact with the outer ring 604 and a surface of screw clamp assembly 622 that may be parallel to the clip engagement member 118. The locking groove 634 may protrude a length orthogonally from a surface of the screw clamp assembly 622.

The screw clamp assembly 622 may comprise the piston 624. The piston 624 may comprise a rectangular upper portion with a rounded or filleted edge and may comprise a u-shaped bottom portion. The u-shape of the u-shaped bottom portion may be in contact with the alignment tab 106. The piston may comprise a front surface and a parallel back surface. The back surface may be in contact with the contact surface 626. When the piston is placed in the screw clamp assembly 622, the front surface and the back surface of the piston may be parallel to a surface of the screw clamp assembly 622 and the clip engagement member 118. The front surface may be connected to the shaft 628.

The shaft 628 may protrude orthogonally from the front surface of the piston 624. The distal end of the shaft 628 may have a threaded hole, such as threaded hole 618. The shaft 628 may have one or more keyways, such as keyway 616. The keyway 616 may have a complementary shape to the key 614. The keyway 616 may be a channel that runs from the distal end of the shaft 628 to the proximal end of the shaft 628 and may terminate at the front surface of the piston 624.

When assembled, the screw clamp assembly 622 may engage the piston 624 such that the contact surface 626 and the contact surface 119 may become pads of a clamp. The screw clamp assembly 622 may cause the piston 624 to move towards the clip engagement member 118, such that the contact surface 626 may contact one surface of a smart device, and the contact surface 119 may contact another surface of the smart device.

The contact surface 626 and/or the contact surface 119 may be made up a material that prevents damage, such as scratching, to a surface of the smart device. The contact surface 626 and/or the contact surface 119 may be made of rubber, fabric, plastic, and/or any other material that may prevent damage to the smartphone. The contact surface 626 and/or the contact surface 119 may be made of a material that prevents the clamp from slipping from the surface of the smartphone. For example, the contact surface 626 and/or the contact surface 119 may be made of rubber which may provide friction to prevent the clamp from slipping and/or moving from a position on a surface of the smart device.

The screw clamp assembly 622 may be assembled. The end cap 304 may be in contact with the clip engagement member 118. The contact surface 119 may be placed on the inner surface 630 of clip engagement member 118. The inner surface 630 may face a surface of the smart device that includes a camera. The inner surface 630 may be parallel to the inner surface of the screw clamp assembly.

The contact surface 626 may be in contact with the piston 624. The shaft 628 of the piston 624 may be placed within the aperture formed by inner ring 606 such that keyway 616 may contact the key 614. For example, the shaft 628 of the piston 624 may be placed within aperture 632. When the piston 624 may be placed within aperture 632. When the shaft 628 is placed through the aperture 632, the piston 624 may be positioned such that contact surface 626 may be parallel to the contact surface 119, and the alignment tab 106 may extend beyond an edge of the screw clamp assembly 622.

The knob cap 600 may be placed in contact with the circular surface 610, which may be associated with knob 114. For example, the knob cap 600 may be press fit into circular surface 610 such that the knob cap 600 may be in contact with (e.g., flush) with circular lip 612. The knob 114 may be in contact with the outer ring 604. For example, the knob 114 may be pressed onto the outer ring 604 and may contact the interior of the knob 114 such that knob 114 may be movably connected to the outer ring 604. For example, when movably connected to the outer ring 604, the knob 114 may be twisted by a user.

The knob 114 may include a threaded protrusion that may be connected to the shaft 628 of the piston 624. The threaded protrusion on the knob 114 may be inserted and/or threaded to the threaded hole 618 within the shaft 628. The threaded protrusion may allow knob 114 to secure the piston 624 in a position that may be parallel to the clip engagement member 118.

The knob 114 may be twisted and may cause the clamp formed by the screw clamp assembly 622 to clamp a smart device. For example, twisting the knob 114 may cause the threaded protrusion of the knob 114 to thread or unthread the threaded hole 618. The rotational force of the threading or unthreading of the threaded hole 618 may be redirected by one or more keys onto one or more keyways such that the piston 624 may be prevented from rotating and may be forced to move linearly in a direction toward or away from the clip engagement member 118. For example, the rotational force generated by the threading or unthreading of the threaded hole 618 may be transferred as a linear force to the piston 624 via the threaded hole 618, the key 614, and/or the keyway 616. Twisting the knob 114 may move the piston 624 toward clip engagement member 118, such that the contact surface 626 may move towards a parallel surface of the clip engagement member 118, such as the contact surface 119. Twisting the knob 114 may cause the contact surface 626 and/or the contact surface 119 to contact a surface of a smartphone device. For example, twisting the knob 114 may cause the contact surface 119 to contact a back side of a smart device that may include a camera, and twisting the knob 114 may cause the contact surface 626 to contact a front side of a smart device that may include a display. The knob 114 may comprise a thread, such as a reverse thread.

When turned, the knob 114 may engage the screw clamp assembly 622 such that the piston 624 that may include alignment tab 106 may be moved towards a surface that may be parallel to alignment tab 106, such as the contact surface 119 that may be in contact with a surface of the clip engagement member 118. For example, a user may turn the knob 114 in a clockwise direction so that the alignment tab 106 may move towards a parallel surface of the clip assembly 122. The knob 114 may cause the alignment tab 106 to move towards the clip engagement member 118 such that alignment tab 106 and the clip engagement member 118 may clamp onto the smart device. A user may turn the knob 114 in a counterclockwise direction so that the alignment tab 106 may move away from a parallel surface of the clip assembly 112.

Figure 7:
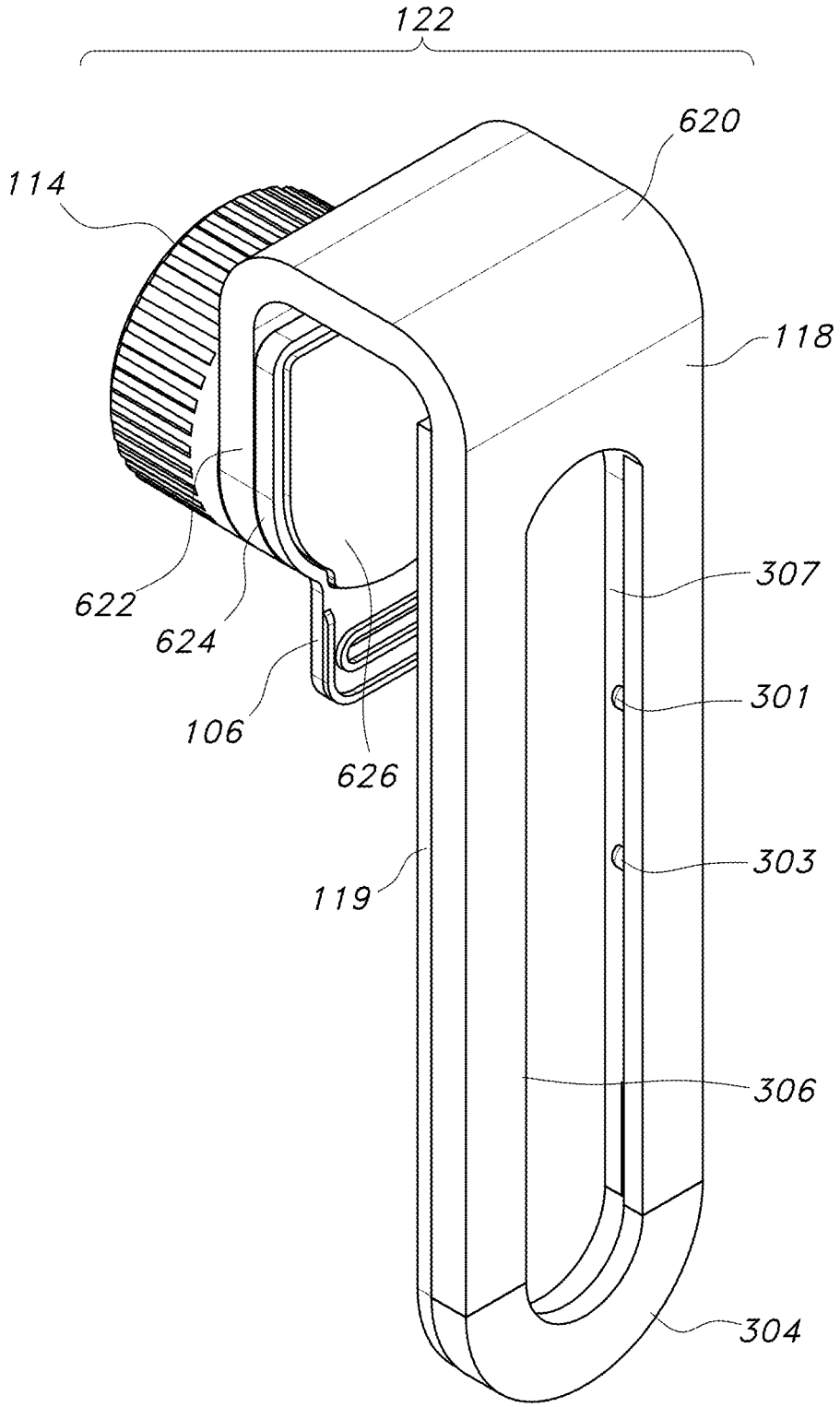
FIG. 7 depicts a perspective view of a clip assembly that may comprise a screw clamp assembly.

FIG. 7 depicts a perspective view of a clip assembly that may comprise a screw clamp assembly. As shown in FIG. 7, the clip assembly 122 may be assembled and may comprise a number of components. The clip assembly 122 may comprise the knob 114. The knob 114 may be connected to the piston 624 via an aperture through the screw clamp assembly 622, such as aperture 632 (shown in FIG. 6). The piston 624 may be in contact with the contact surface 626. The piston 624 may comprise the alignment tab 106. The screw clamp assembly 622 may be in contact with the connecting member 620. The connecting member 620 may be in contact with the clip engagement member 118. The clip engagement member 118 may comprise an elongated aperture and may have one or more internal sidewalls along the elongated aperture. The one or more internal sidewalls of the clip engagement member 118 may comprise a channel. For example, the clip engagement member 118 may comprise the channel 306 and the channel 307. The channel 307 may comprise the latching element 301 and the latching element 303. The channel 306 may comprise the latching element 300 and the latching element 302. The clip engagement member 118 may comprise the end cap 304.

Figure 8:
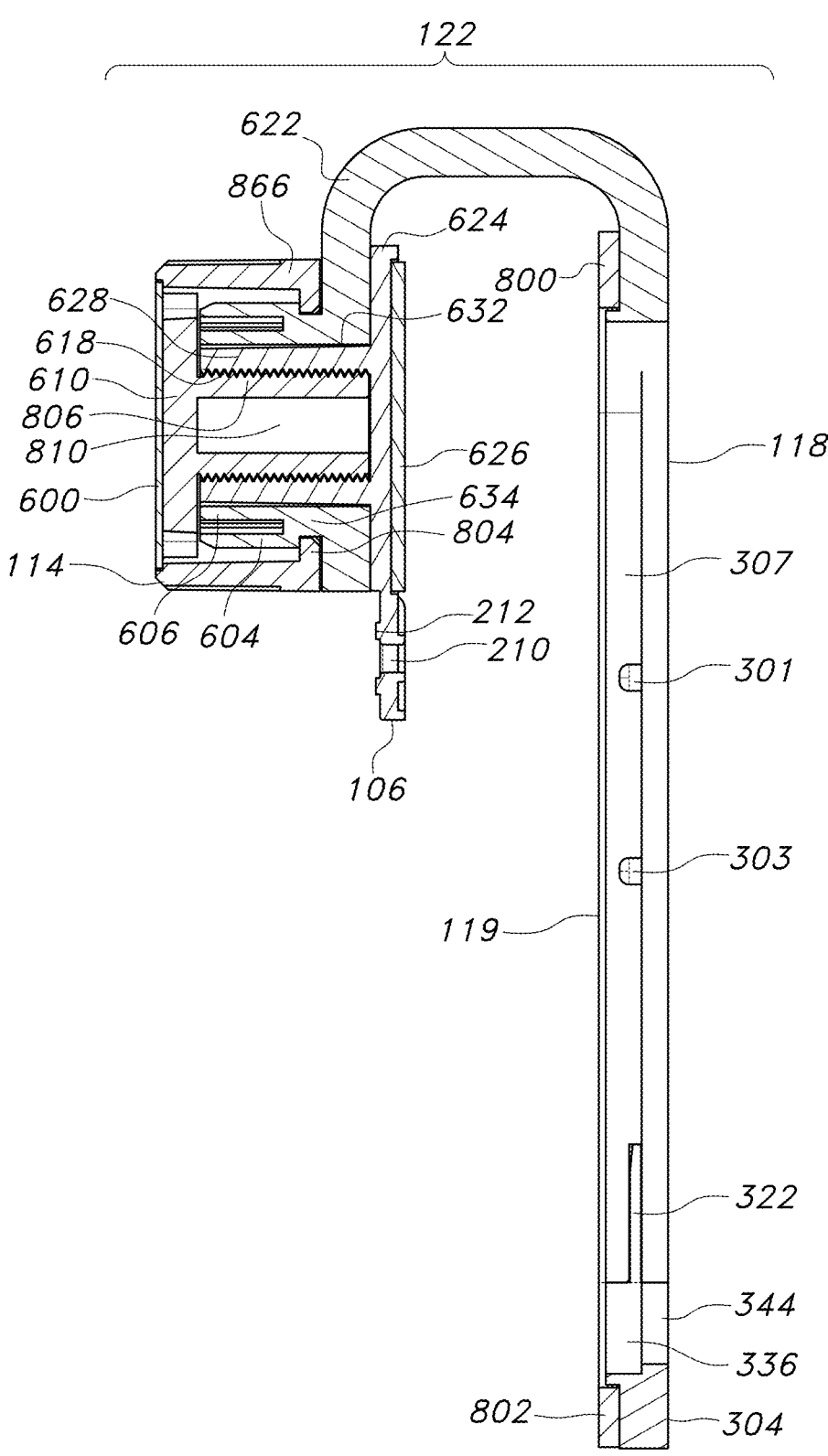
FIG. 8 depicts a cross-section view of a clip assembly that may comprise a screw clamp assembly.

FIG. 8 depicts a cross-section view of a clip assembly that may comprise a screw clamp assembly. The clip assembly 122 may comprise the clip engagement member 118. The clip engagement member 118 may comprise the channel 307 that may run a length of the clip engagement member 118. The channel 307 may comprise the latching element 301 and the latching element 303. The latching element 301 and/or the latching element 303 may engage a receiver element that may belong to an otoscope engagement member.

The clip engagement member 118 may comprise the engagement member leg recess 344. The engagement member leg recess 344 may be engaged with the end cap foot 366. The end cap foot 366 may be resilient and may be resiliently connected to the engagement member leg recess 344, such that end cap 304 may be removably attached to clip engagement member 118.

The clip engagement member 118 may be connected to the contact surface 119. The contact surface 119 may be of varying thickness. For example, the contact surface 119 may be of one thickness at its center and may be of a different thickness at its ends. For example, the contact surface 119 may have a different thickness at the end of contact surface 800 and/or the end of contact surface 802 than at a different location within the contact surface 119.

The screw clamp assembly 622 may comprise the aperture 632. The aperture 632 may be located at a surface of the screw clamp assembly 622 that may be parallel to the clip engagement member 118. The shaft 628 of the piston 624 may pass through the aperture 632. The shaft 628 may be connected to the piston 624. The shaft of 628 may protrude orthogonally from a surface of the piston 624. The shaft of 628 may move freely through the aperture 632. The shaft of 628 may have an exterior and an interior. The interior of the shaft of 628 may comprise the threaded hole 618. For example, the distal end of the shaft 628 may have a threaded hole.

The threaded hole 618 may be engaged by the knob 114 via the threaded protrusion 806. For example, the threaded protrusion 806 may contact the threaded hole 618 by threading the threaded hole 618. The threaded protrusion 806 may have a hollow interior. For example, the threaded protrusion 806 may have an outer wall with a thread and may have an inner wall that may form a cylindrical hole that extends towards the piston 624, such as the hole 810. The threaded protrusion 806 may have a reverse thread. The threaded protrusion 806 may protrude from the circular surface 610. For example, the threaded protrusion 806 may protrude orthogonally from the circular surface 610. The threaded protrusion 806 may be connected to the circular surface 610.

The circular surface 610 may be countersunk such that a circular lip may be formed. The knob cap 600 may be in contact with circular surface 610. For example, the knob cap 600 may be press fit into circular surface 610 such that knob cap 600 be near or flush with the circular lip.

The aperture 632 may be surrounded by the inner ring 606. For example, the inner ring 606 may contact a circumference of the aperture 632.

The inner ring 606 may contact a surface of the screw clamp assembly 622 that may be parallel to the clip engagement member 118. The inner ring 606 may be a hollow cylinder with an inner surface, and an outer surface, and an aperture complementary positioned to the aperture 632. The inner ring 606 may protrude a length orthogonally from a surface of the screw clamp assembly 622. The inner ring 606 may comprise one or more keys that may be located on the inner surface of the inner ring 606.

The outer ring 604 may be of a larger circumference than the inner ring 606. The outer ring 604 may be in contact with a surface of the screw clamp assembly 622. The outer ring may protrude a length orthogonally from a surface of the screw clamp assembly 622. The distal end of outer ring 604 may be chamfered. The outer ring 604 may have one or more notches or kerfs. The proximal end of outer ring 604 may be in contact with the locking groove 634.

The locking groove 634 may have a circumference that may be smaller than the outer ring 604. The locking groove 643 may be larger than the circumference of the inner ring 606. The locking groove 634 may be in contact with the outer ring 604 and a surface of the screw clamp assembly 622 that may be parallel to the clip engagement member 118. The locking groove 634 may protrude a length orthogonally from a surface of the screw clamp assembly 622.

The knob 114 may comprise the circular surface 610, the threaded protrusion 806, the hole 810, the knob cap 600, and the locking ring 804. The knob 114 may be cylindrical and may have a textured outer surface, such as the knob outer surface 807, which may be splines, knurling, and/or the like. The knob 114 may comprise the knob outer surface 807, the locking ring 804, and the threaded protrusion 806. The locking ring 804 may have a circumference that may be larger than the outer ring 604. The locking ring 804 may be formed at the end of the knob that is nearest to outer ring 604. The locking ring may have a smaller circumference than the outer ring 604. The locking ring may be of a larger circumference than locking groove 634. The locking ring may be resilient such that it may resiliently contact the locking groove 634 such that knob 114 may be removably attached to the screw clamp assembly 622.

The piston 624 may comprise the alignment tab 106. The alignment tab 106 may comprise the vertical alignment tab feature 210 and the horizontal alignment tab feature 212. The vertical alignment tab feature 210 may be aperture, such as an oval aperture. The horizontal alignment tab feature 212 may be a protrusion, such as a triangle or arrow-shaped protrusion. The horizontal alignment tab feature 212 may protrude orthogonally from a surface of the piston 624.

The knob 114 may be twisted and may cause the clamp formed by the screw clamp assembly 622 to clamp a smart device. For example, twisting the knob 114 may cause the threaded protrusion 806 to thread or unthread the threaded hole 618. The rotational force of the threading or unthreading the threaded hole 618 may be redirected by one or more keys onto one or more keyways such that piston 624 may be prevented from rotating and may be forced to move linearly in a direction toward or away from the clip engagement member 118. For example, the rotational force generated by the threading or unthreading the threaded hole 618 may be transferred as a linear force to piston 624 via threaded hole 618, a key, and/or a keyway. Twisting the knob 114 may move piston 624 toward the clip engagement member 118 such that the contact surface 626 may move towards the contact surface 119. Twisting the knob 114 may cause the contact surface 626 and/or the contact surface 119 to contact a surface of a smartphone device. For example, twisting the knob 114 may cause the contact surface 119 to contact a back side of a smart device that may include a camera, and twisting the knob 114 may cause the contact surface 626 to contact a front side of a smart device that may include a display.

Figure 9A:
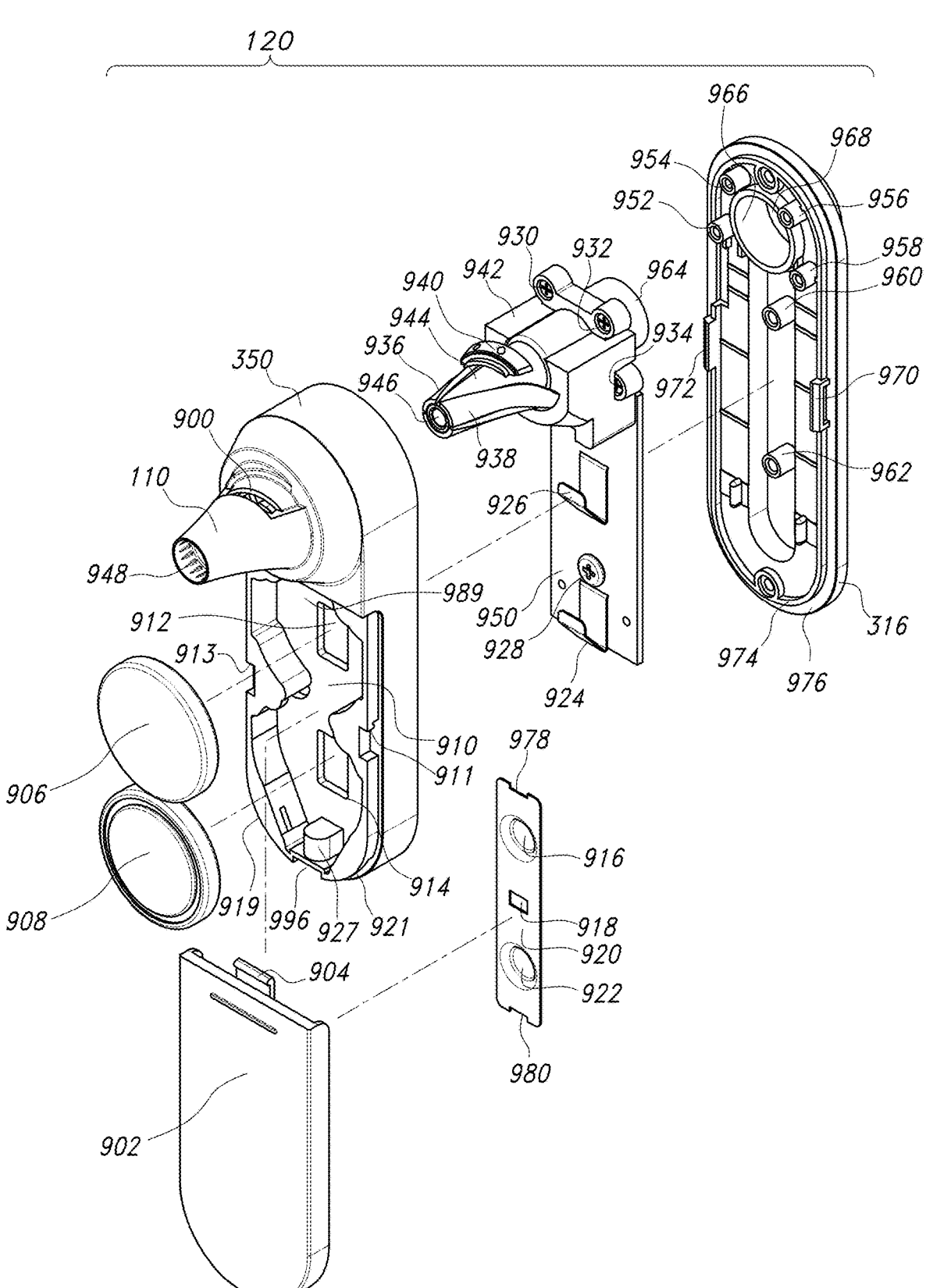
FIGS. 9A-9B depict schematic views of an otoscope assembly that comprises one or more components.
Figure 9B:
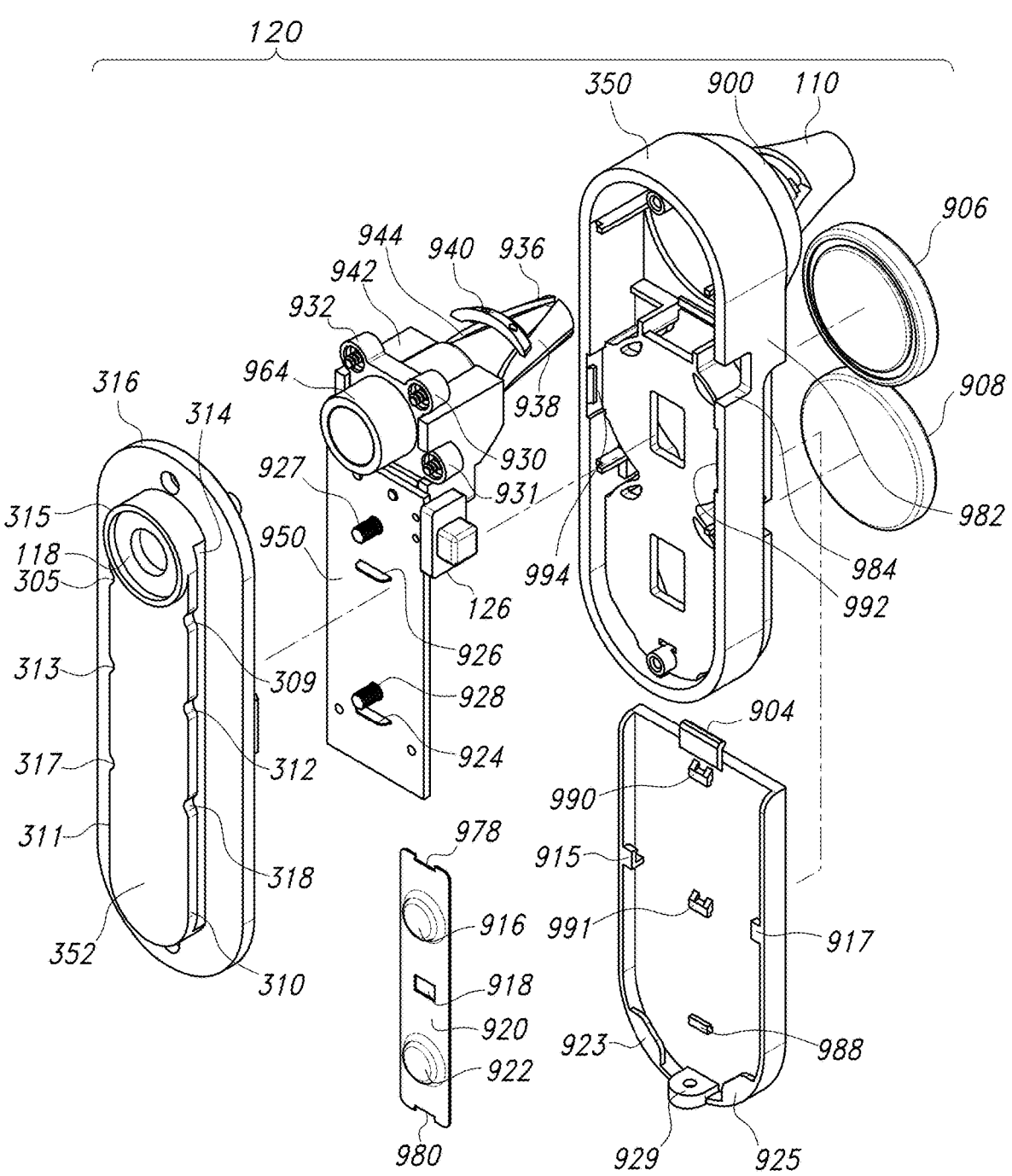

FIGS. 9A-B depict schematic views of an otoscope assembly 120 that comprises one or more components. The otoscope assembly 120 may comprise the battery cover 902, the main body 350, the inner otoscope housing 942, and the otoscope back-plate 316.

The battery cover 902 may comprise the retention protrusion 915, the retention protrusion 917, the retention protrusion 923, and the retention protrusion 925. The retention protrusion 915 and/or the retention protrusion 917 may connect to the battery cover and may connect to an inner sidewall that is orthogonal to the underside of the battery cover. The retention protrusion 915 and/or the retention protrusion 917 may protrude from the inner sidewall of the battery cover 902. The retention protrusion 915 and/or the retention protrusion 917 may be an L-shape, with at least a leg parallel with the inner side wall of the battery cover 902. The retention protrusion 923 and/or the retention protrusion 925 may protrude from the inner side wall of the battery cover 902 in an axis parallel to the underside of the battery cover 902.

The retention protrusion 915, the retention protrusion 917, the retention protrusion 923, and the retention protrusion 925 may allow the battery cover 902 to be in contact with the main body 350. For example, the retention protrusion 917 may engage with the recess 913, the retention protrusion 915 may engage with the recess 911, the retention protrusion 925 may engage with the recess 919, and/or the retention protrusion 923 may engage with the recess 921.

The battery cover 902 may comprise the battery case tab 904, the battery case tab 990, the battery case tab 991, the battery case tab 988, the retention protrusion 915, the retention protrusion 917, the retention protrusion 923, and the retention protrusion 925, and the screw guide 929. The battery cover 902 may cover a lower portion of the main body 350. The battery cover 902 may cover the battery cavity 910 in the main body 350 that may contain the battery 906 and/or the battery 908. The battery 906 and/or the battery 908 may be a battery such as a lithium-ion battery, an alkaline battery, and/or the like. The battery cover 902 may have a top side that may not include any tabs, an underside that includes a number of tabs. The underside of the battery cover 902 may face the battery cavity 910. Although the embodiments disclosed herein may be shown using a coin battery, other battery shapes and/or sizes may be used. For example, the main body 350 may be reconfigured to be used with an A battery, a AA battery, a AAA battery, and/or the like.

The battery case tab 990 may protrude from the underside of the battery cover 902 and may end in a foot that may protrude towards the battery case tab 988. The battery case tab 991 may protrude from the underside of the battery cover 902 and may end in a foot that may protrude towards the battery case tab 988. The battery case tab 988 may protrude from the underside of the battery cover 902 and may end in a foot that may protrude toward the battery case tab 990. The battery case tab 990, the battery case tab 991, and the battery case tab 988 may be a set distance apart such that the battery connector 920 may be snap-fit into battery case tab 990, the battery case tab 991, and the battery case tab 988.

The battery connector 920 may be made of an electrically conductive material such as a metal. The battery connector 920 may have the rectangular aperture 918 in its center. The battery case tab 991 may go through the rectangular aperture 918 to allow the battery connector 920 to snap-fit into battery case tab 991. The battery connector 920 may have the battery contact protrusion 916 at one end and the battery contact protrusion 922 at another end. The battery contact protrusion 916 and/or the battery contact protrusion 922 may be a conical frustum. The conical frustum may protrude on the side of the battery connector 920 that may face the batteries.

The battery connector 920 may have the notch 978 at one end and the notch 980 at the other end. The battery connector 920 may be snap-fit into the battery cover 902. For example, the battery case tab 990 may engage the notch 978 and the battery case tab 988 may engage the notch 980 such that the battery connector may be snap-fit into the battery cover case 902.

The battery cover 902 may comprise the battery case tab 904 and the screw guide 929. The battery case tab 904 may protrude in a parallel direction from the underside of the battery cover 902 towards an end of the battery case cover 902. The battery case tab 904 may connect the battery cover 902 to the main body 350 by engaging with the notch 989. The screw guide 929 may be connected the battery cover 902. The screw guide 929 may include a clip that may retain a screw. For example, the screw guide 929 may retain a screw when the screw is not engaged with the screw boss 927.

The screw guide 929 may protrude orthogonally from the battery cover 902. The distal end of the screw guide 929 may be rounded or may be a half-circle. The proximal end of the screw guide 929 may be a rectangular shape and may have a surface in contact with the battery cover 902. The screw guide 929 may have an aperture. The aperture of the screw guide 929 may be along an axis that may be parallel to the underside surface of the battery cover 902. The aperture of the screw guide 929 may allow a screw to go through the screw guide 929 and contact the screw boss 927. The battery cover 902 may be connected to the main body 350 and may be screwed into place via a screw that goes through an aperture of the screw guide 929 and connects with the screw boss 927.

The main body 350 may comprise an upper portion and a lower portion. The upper portion of the main body 350 may comprise the outer tip housing 110. The outer tip housing 110 may be a conical shape and may comprise an opening at the distal end, such as the outer tip hole 948. The sidewall of the outer tip housing 110 may comprise a radial slot out, such as the radial slot 900. The radial slot 900 may be a radial aperture such that radial protrusion 940 may go through the radial slot 900. The radial slot 900 and/or the radial protrusion 940 may allow for a speculum to be removably connected to the outer tip housing 110.

The outer tip housing 110 may be conically hollow inside. For example, the outer tip housing 110 may be conically hollow such that the inner tip housing 944 may fit inside the outer tip housing 110. The outer tip housing 110 may have a complementary shape to the inner tip housing 944.

The main body 350 may comprise a lower portion. The lower portion of the main body 350 may comprise the battery cavity 910. The battery cavity 910 may comprise the rectangular aperture 912 and the rectangular aperture 914.

The rectangular aperture 912 may allow a portion of the biased member 926 to pass through such that the biased member 926 may contact the battery 906 when the battery 906 is within the battery cavity 910. The rectangular aperture 914 may allow a portion of the biased member 924 to pass through such that the biased member 924 may contact the battery 908 when the battery 908 is within the battery cavity 910.

The main body 350 may comprise an outer sidewall, such as the main body outer sidewall 982. The main body outer sidewall 982 may comprise a notch, such as the switch notch 984. The switch notch 984 may be placed at the portion of the sidewall that contacts the otoscope back-plate 316. The switch notch 984 may be a rectangular shape and may complement the light switch 126.

The main body 350 may comprise the recess 911, the recess 913, the recess 923, and the recess 921. The recess 911, the recess 913, the recess 919, and/or the recess 921 may be a recess in a surface of the main body 350 that may contact the battery cover 902. The recess 911, the recess 913, the recess 919, and/or the recess 921 may engage with a retention protrusion such that the battery cover 902 may be connected and/or in contact with the main body 350. For example, the recess 911 may engage with the retention protrusion 915, the recess 913 may engage with the retention protrusion 917, the recess 919 may engage with the retention protrusion 925, and/or the recess 921 may engage with the retention protrusion 923.

The main body 350 may comprise the screw boss 927. The screw boss 927 may be located at a lower end of the main body 350, away from the notch 989. The screw boss 927 may receive a screw that may be placed through the screw guide 929. The battery cover 902 may be connected to the main body 350 using a screw that may be placed through the screw guide 929 such that the screw connects with the screw boss 927.

The main body 350 may comprise the battery case cut out 996. The battery case cut out 996 may be a cut out in a side wall of the main body 350. For example, the battery case cut out 996 may be a cut out in the main body outer sidewall 982. The battery case cut out 996 may be located at an end of the main body 350, which may be away from the notch 989. The battery case cut out 996 may be a shape that may be complementary to the screw guide 929. The screw guide 929 may fit within the battery case cut out 996.

The inner otoscope housing 942 may fit inside the main body 350. The inner otoscope housing 942 may comprise the inner tip housing 944, the otoscope tube 964, and the backer board 950. The inner otoscope housing 942 may be connected to the otoscope back-plate 316 using a number of screws. For example, screw 930 may engage screw boss 954, screw 931 may engage screw boss 952, screw 932 may engage screw boss 956, screw 934 may engage screw boss 958, screw 927 may engage screw boss 960, and screw 928 may engage screw boss 962.

The inner otoscope housing 942 may comprise a hollow portion that may contain a number of electronics. For example, the inner otoscope housing 942 may include a printed circuit board (PCB); a light source, such as an LED; a speaker; a lens; a combination thereof; and/or the like. The otoscope tube 964 may contact and/or be attached to the inner otoscope housing 942. The proximal end of the otoscope tube 964 may contact the inner otoscope housing 942.

The otoscope tube 964 may protrude from the inner otoscope housing 942 towards the otoscope back-plate 316. The otoscope tube 964 may comprise a cylindrical protrusion with an outer wall, a hole at a distal end, and an inner wall formed by the hole. The outer wall of the otoscope tube 964 may have a smaller diameter than the aperture 968 in the otoscope back-plate 316. The otoscope tube 964 may pass through or protrude into the aperture 968 such that the otoscope tube 964 may deliver an image from the inner tip hole 946 to the viewing portion 108 via the aperture 968.

The inner otoscope housing 942 may comprise the inner tip housing 944. The inner tip housing 944 may be connected to the light pipe 938 and the light pipe 936. The light pipe 938 and/or the light pipe 936 may provide light, for example, by transporting light from an LED within the inner otoscope housing 942 towards the inner tip hole 946. The light pipe 938 and/or the light pipe 936 may be made the plastic, fiber optic, and/or another light-carrying material.

The inner otoscope housing 942 may comprise the radial protrusion 940. The radial protrusion 940 may allow a removable speculum to be removably connected to the outer tip housing 110. The radial protrusion 940 may protrude orthogonally from an outer surface of the inner tip housing 944. The radial protrusion 940 may follow a radius along the outer surface of the inner tip housing 944.

The backer board 950 may connect to a bottom portion of the inner otoscope housing 942. The backer board 950 may comprise the biased member 924 and the biased member 926. The biased member 924 and/or the biased member 926 may be made of a resilient material and may be made of an electrically conducting material. For example, the biased member 924 and/or the biased member 926 may be made of copper. The bias members, such as the biased member 926 and the biased member 926, may comprise three members. The first member that may be parallel to the backer board 950. The first member of the biased member 924 may be attached to a second member that protrudes along an axis away from the backer board 950 and towards the main body 350. The second member may be attached to a third member that may be parallel to the backer board 950.

A portion of the biased member 926 may pass through the rectangular aperture 912 such that the biased member 926 may contact the battery 906 when the battery 906 is within the battery cavity 910. A portion of the biased member 924 may to pass through the rectangular aperture 914 such that the biased member 924 may contact the battery 908 when the battery 908 is within the battery cavity 910.

The otoscope back-plate 316 may be connected to the main body 350. The otoscope back-plate 316 may comprise the backing tab 970 and the backing tab 972. The backing tab 970 and backing tab 972 may protrude orthogonally from back-plate shoulder 976. The backing tab 970 may end in a foot that may extend inward towards backing tab 972. The backing tab 972 may end in a foot that may extend inwardly toward backing tab 970. The backing tab 970 and the backing tab 972 may be resilient and may be made of a resilient material. The otoscope back-plate 316 may be removably connected to the main body 350. For example, the backing tab 970 may be resiliently connected to the main body tab 994 and the backing tab 972 may be resiliently connected to the main body tab 992 such that the otoscope back-plate 316 may be removably connected to the main body 350.

The otoscope back-plate 316 may comprise to back-plate shoulder 976. The back-plate shoulder 976 may be parallel to the otoscope engagement member 352. The back-plate shoulder 976 may connect with the back-plate lip 974. The back-plate lip 974 may protrude orthogonally from the back-plate shoulder 976. The back-plate lip 974 may fit within the main body 350 when the otoscope back-plate 316 is connected to the main body 350. The back-plate shoulder

976 may contact the main body 350 when the otoscope back-plate 316 is connected to the main body 350.

The otoscope engagement member 352 may be connected to the otoscope back-plate 316. The otoscope engagement member 352 may allow the otoscope assembly 120 to attach to, connect to, or engage with a clip engagement member of an otoscope clip.

The otoscope engagement member 352 may comprise a guide track, such as the guide track 314 and the guide track 315. The guide track may be a channel formed in a surface of the otoscope engagement member 352 that may face an inner surface of a clip engagement member. The guide track may be a channel in a surface of the otoscope engagement member 352 that may be orthogonal to a surface of the otoscope back-plate 316. The guide track may be connected to the otoscope back-plate 316 and may be connected to a protruding connecting member, such as the protruding connecting member 310 and/or the protruding connecting member 311.

The otoscope engagement member 352 may have an undercut in one or more sides that may be orthogonal to the otoscope back-plate 316 such that an overhang may be created. The overhang may be parallel to the otoscope back-plate 316. The undercut may be the guide track 314 and/or the guide track 315. The overhang may be the protruding connecting member 310 and/or the protruding connecting member 311. The overhang may include one or more receiver elements that may be designed to engage with one or more resilient members, such as latching elements, within the channel 306 and/or the channel 307. The one or more receiver elements may be recesses, cut outs, detent indentation, and/or the like. For example, the protruding connecting member 310 may include receiver elements, such as the receiver element 309, the receiver element 312, and the receiver element 318. The receiver elements may engage with the latching element 300 and/or the latching element 302. As another example, the protruding connecting member 311 may include receiver elements, such as the receiver element 305, the receiver element 313, and the receiver element 317. The receiver elements may engage with the latching element 301 and/or the latching element 303.

Embodiments disclosed herein may provide design options for obtaining enhanced image contrast. As noted above, an otoscope may be used for diagnosing and identifying problems of the outer ear and/or middle ear, also referred to as the ear canal, such as issues with a tympanic membrane, or an ear infection (e.g., acute otitis media). When joined with a camera, the otoscope may be used for remote diagnosis when images or videos are recorded by the user. For example, the otoscope may be used for tele-otoscopy and may enable a user to record an image of an ear canal of a patient (e.g., an image of the tympanic membrane). And the image may be sent to a remote physician for diagnosis. The embodiments described herein may assist a user in taking a clear picture or a clear video.

Challenges may arise when the camera paired with an otoscope is the camera of a smartphone. Smartphone cameras are typically small, often having lenses less than 1 centimeter in diameter and a small, fixed aperture, and designed to image objects located at distances greater than approximately 30 centimeters. Smartphone cameras may also have features like autofocus and optical image stabilization, which may complicate pairing with an external device. Additionally, enhancing image contrast and reducing issues like veiling glare may ensure that the ear images taken are usable for remote diagnosis. A general background on otoscope design and a discussion of issues specific to pairing an otoscope with a smartphone camera, are further addressed below.

In general, an otoscope device may include two primary sub-systems: an illumination optics system (also called a light optics system) and an imaging optics system (also called a camera optics system). There may also be an influencing component, for example, a speculum, that may influence both the illumination optics system and the imaging optics system through light reflections off of the speculum's internal surface. The illumination optics system, imaging optics system, and speculum may interact with each other by design to improve imaging performance. Embodiments provided herein may use an illumination optics system. An illumination optics system may be used to transfer light from a source (e.g., a LED) to an intended target (e.g., the intended field of view on the eardrum) as efficiently and uniformly as possible. The illumination optics system may fit within the physical confines of an otoscope instrument and may be required to meet cost constraints for its intended market(s).

As shown in FIG. 10A, an otoscope may co-locate the camera optics and the illumination optics (also called light optics) along the same axis, resulting in a system with "in-line illumination" or "on-axis illumination." While an on-axis system, co-axial with the imaging optics, may be efficient, it may use one or more features (e.g., add complexities) to minimize backscatter to the camera. These features may include adding a beam splitter, a lens coating, a polarizer, and/or a mechanical baffling. This approach may increase the cost of the otoscope beyond the economic constraints of many intended markets, including, for example, markets for direct consumer use or tele-otoscopy.

As shown in FIG. 10B, an otoscope may use "offset illumination" where an angle or displacement exists between the camera optics axis and the light optics axis. It is noted that the confined cavity of the ear canal or other bodily cavities may not permit a large offset between the optical components and the illumination, however even a moderate offset may add some enhanced degree of texture visualization. Offset illumination may also minimize light scatter resulting in a sharper image. According to one embodiment, such an offset illumination system may use a custom or reusable speculum that would allow the camera optics and illumination optics to be close to the tip of the speculum (e.g., as close to the tip of the speculum as possible). For example, the camera optics and illumination optics may be located to maximize the relative angles between the collection/emission surfaces of the camera and illumination optics and the subject.

As shown in FIG. 10C, an otoscope may use an indirect light source, also called "annular illumination," where the light is reflected off a surface (e.g., the ear canal) before reaching the subject (see FIG. 10C). Such an indirect illumination source may not be directed at the subject but at the canal wall, where one or more reflections may occur before the light reaches the subject. The resulting visual effect of the reflected light setup may include better illumination of the subject from multiple angles. For example, unlike some other illumination approaches, annular illumination may not be prone to complete obscuration by a peripheral object due to the wider range of angles utilized.

One example of indirect illumination is the use of fiber optics to direct light from a light source (e.g., which may be located near the battery) to form a ring light, or a coaxial ring, around the viewing area of the otoscope to illuminate the ear canal, as shown in FIG. 10C. The use of indirect illumination with fiber optics may allow for an unobscured viewing area, as well as greater freedom in the placement of the illumination components and an additional factor of safety as one or more electrical contacts may be isolated away from the patient's ear canal. Such a coaxial system may provide uniform illumination of the ear canal around the optics axis and provide better visualization of the ear canal.

While images of the ear canal are formed by reflected light, indirect illumination may have some disadvantages, irrespective of the light source configuration. For example, specular reflections from wetted surfaces may be considered a problem with some images, resulting in bright saturated regions that may hide image attributes. This may be more problematic with an annular illumination approach because the light is incident on a specular feature from a wider range of angles. Additionally, a reflected light setup may cause some light to be absorbed and not reflected in the reflection process. The amount of light lost to absorption may depend on the material properties of the canal wall, including moisture, the presence of cerumen or other materials, etc. The reflected light may also take on some of the coloration of the canal wall and/or the reflected light may be partially occluded by objects which may not occlude the light if it were collinear with the camera optics.

In an example, these disadvantages may be overcome via one or more of the following exemplary techniques: ensure that the incident light amplitude is sufficiently high that enough light reaches the subject after reflection; correct the color of the subject in post-processing using white balance techniques; and/or allow rotation of the otoscope around the axis of the ear canal by the operator to avoid any occluding objects.

The use of fiber optics may have several limitations. The fibers may need to be polished to transmit light. The polishing process may be time-consuming and expensive. The polishing process may introduce variability in the light output as the sanding pads on the polishing equipment wear with use. The fibers may also be limited by the circular profile of the fiber optics themselves. The path of the fibers may also be limited by the material properties of the fiber optics, which may reduce their efficiency if they are bent too tightly.

As disclosed herein, an embodiment may use light pipes, which may be injection molded light pipes. The light pipes (also known as lightpipes, light guides, wave guides or other similar terms) may guide the light from a source away from the viewing area (e.g., in one case a phone, in another case an LED on a circuit board) to form a ring light, or coaxial light, around the viewing area of an otoscope. A light pipe may be an injection molded part that may be simpler, cheaper and more consistent than a polished fiber optic bundle. Additionally, the greater freedom allowed in shaping the light pipe may allow for it to be made to fit into more compact otoscopes while retaining good light output performance necessary for viewing the ear canal.

A light pipe may also help overcome some challenges with the handset compatibility of an imaging attachment. For example, the collection side of the light pipe may be designed to funnel in the light from several possible source positions, which can make it possible for a light pipe design (e.g., a single light pipe design) to work with multiple handsets. This utility is apparent, for example, when operating with different phone types, such as the iPhone 5 and 5S or similar later versions of the iPhone, which have a consistent overall form factor, but vary in the design and position of the camera's LED flash. A light pipe may have a collection feature that combines two or more LED sources, and re-directs the light according to the application (e.g., a ring light in an otoscope, structured or diffuse illumination in a dermascope, etc.).

Alignment (e.g., precise alignment) with the light source may further help optimize the performance of the light pipe. For example, precise alignment may help enable a light pipe design (e.g., a single light pipe design) to be positioned to work with multiple LED positions. For example, a light pipe may be designed to accommodate a light source at a specific radial distance from the imaging optical axis. As such, it may accommodate other rotational positions at the same radial distance. In an example, a light pipe may be designed to accommodate light sources at two or more specific radial distances from the imaging optical axis.

A light pipe may also incorporate an intermediate light collection feature, which takes in light from the handset, circuit board, or other illumination source, and transfers it on to another application-specific illumination module.

The light pipe may create a small diameter annular exit surface surrounding the distal end of the optics or lens tube, in proximity to the imaging optics' objective lens. The light pipe may function to deliver light to this point from a displaced light source; for example, a light emitting diode (LED). A light pipe may be a simple or a complex shape. For example, the shape of the light pipe may be selected or designed to meet system requirements and may utilize curved, tapered, lenticular or prismatic surfaces along with single or multiple entry and exit apertures.

The light pipes described herein may have a constant cross-section throughout each element (or each "pipe") or a varying cross-section throughout each element (or each "pipe"). In some embodiments of the light pipe, it may be helpful to maintain a constant (or nearly constant) cross-sectional area along the segments of the light pipe to maximize transmission efficiency.

A light pipe may comprise a polished reflective material such as aluminum, silver, gold, platinum, and/or the like. A light pipe may comprise a clear optical material, such as plastic, glass, and/or crystal.

As disclosed herein, an optical material may be a plastic, glass, or crystal. For example, the plastic may be polycarbonate, acrylic, polymethyl methacrylate (PMMA), polystyrene polyethylene terephthalate (PET), and/or the like. For example, the glass may be a crown glass, a flint glass, a borosilicate glass, a fused quartz, a soda-lime glass, and/or the like. For example, the crystal may be quartz, calcite, sapphire, diamond, and/or the like.

In an embodiment, a light pipe may comprise an optical material that may not be reflectively coated. For example, the light pipe may comprise an optical material that may not be reflectively coated and may depend on total internal reflection (TIR) to be efficient. Efficiency (e.g., transmission efficiency or illumination efficiency) may be measured by the power out versus the power in. For example, a ray of light will typically reflect off intermediate side walls multiple times between input and output. As a ray exits from the higher refractive index light pipe material to a lower index medium, for example, air, the ray angle bends toward the plane of the exiting surface. When the exiting ray is parallel with the surface, this is referred to as the critical angle of the incident ray within the light pipe, as defined by Snell's Law:

$$\theta = \sin^{-1}\left(\frac{n1}{n2}\right) = 41^{\circ}, \qquad \text{Formula A}$$

where n1 is the refractive index of the medium (e.g., about 1 for air) and n2 is the refractive index for the light pipe material (e.g., about 1.53 for copolymer plastic). Above this angle, TIR occurs, and below this angle, rays transmit through the surface and are lost. Since curvatures and tapers influence incident angles through the light pipe, design control of these factors may determine the efficiency of the light pipe and the extent of angular dispersion of the output.

According to one embodiment, a light pipe may be configured to start from an off-axis LED location (e.g., a single off-axis LED location) and to route into one or more curved and tapered branches (e.g., three curved and tapered branches) to achieve a segmented annular output with well-balanced illumination. The input to the light pipe may capture an amount of the LED's output power, such as 60% of the LED's output power. The light pipe may be approximately 40% efficient, input to output. Due to the taper, the angular dispersion of the output may be large, and 1.5% of the output power may make it directly through the speculum's output aperture, with the remainder hitting the inner speculum wall. Of that, 70% may be delivered to the intended diameter field-of-view (FOV) zone, which may be 6 mm, at the eardrum, which may be distanced 12 mm from the speculum output.

The overall result may be that only 0.35% of the LED's output reaches the eardrum's 6 mm target FOV zone with a direct path through the speculum's aperture. As disclosed herein, the speculum may have an influence on this. For example, over 98% of the light exiting the light pipe may be incident on the polished black wall of the speculum's interior surface. Fresnel equations describe the reflection of light from polished surfaces and may be relevant at grazing angles of incidence, where even black surface reflectivity may approach 100% at small grazing angles (e.g., very small grazing angles). The grazing incidence reflections on the speculum interior, especially toward the tip, may contribute to more than doubling the illumination in the eardrum target zone. In an example, with the speculum in place, the overall illumination efficiency (LED to eardrum) may approach 1%.

According to one embodiment, light pipes may have a high polish on the light pipe surface. One or more levels of polish may be used on one or more surfaces of a light pipe. For examples, a mid-range finish (e.g., standard precision industrial A2 (SPI-A2)) may be provided on a first light pipe surface and a higher-level finish (e.g., SPI-A1) may be provided on a second surface. For example, SPI-A2 polishing (e.g., a level under lens quality polishing) may be used on one or more surfaces (e.g., all surfaces), and SPI-A1 polishing (e.g., a lens quality polishing) may be used on one or more surfaces (e.g., wherever practical to reach with polishing bit). A light pipe may also have a smooth path on a pipe (e.g., each pipe) and minimized curvature to maximize internal reflection. A light pipe may be an injection-molded light pipe. A light pipe may use LED/light pipe grade plastic with high transmission factor and clarity (e.g., a polycarbonate resin such as Makrolon LED 2045), and/or may include an angled outlet surface (e.g., 1, 2, 5, 7.5, 10, 15 and/or 20 degrees) to redirect output rays forward. This may help control the targeting of the illumination. In a light pipe tapering toward a smaller output, a sequential reflection (e.g., each sequential reflection) of a light ray may move slightly toward normal incidence to the wall until, eventually, the angle may fall below the critical angle and transmit through the wall.

Embodiments described herein may use an imaging optics system. The imaging optics system may include one lens or a series of lenses that deliver an image to a cell phone camera at a near-infinite conjugate. The camera's autofocus system may or may not make final adjustments.

The imaging optic system's f-number is determined by the stop aperture and determines the depth of field (DOF) as well as the amount of light collected. DOF, the focal distance over which an acceptable degree of image resolution is achieved, is proportional to the f-number, while the amount of light collected is inversely proportional to the square of the f-number. A large f-number may also have an impact on degradation of the image resolution due to diffraction of light through the small stop aperture.

There are tradeoffs involved in the selection of the f-number. For example, a small f-number (large stop aperture) may collect more light, allowing for a better image signal-to-noise ratio and sharper image at focus due to minimal diffraction. It may also allow for a simplified illumination system or extended battery life. In contrast, a large f-number (small stop aperture) may require more illumination and may reduce resolution due to diffraction. However, it may extend DOF for a larger volumetric image space, and this may provide for the stabilization of a cell phone's autofocus algorithm, which tends to hunt with motion instabilities, such as user movements. For example, embodiments disclosed herein may address an autofocus algorithm used by a smart device that uses the Apple i5 processor (e.g., an iPhone), and may address autofocus algorithms used by smartphones.

The autofocus function of a smartphone or cell phone, sometimes also called "contrast detection," moves the lens back and forth until it finds the point of maximum contrast for an object, to put the image in focus. The autofocus function may be based largely on trial-and-error. This may create problems when pairing the smart device camera with an external device, since the smartphone camera may not know when it has reached the point of maximum contrast and may continue to "hunt," i.e., move the lens back and forth.

According to one embodiment, an f/45 lens design was determined to satisfy or assist the cell phone's autofocus system, for example, by eliminating or minimizing hunting. In an example, the ear drum may be a Lambertian reflector of incident light from the illumination system, and accounting for optical surface losses, less than 0.012% of that incident light reaches the cell phone camera, which may be further modulated by the eardrum contrast. The total loss from LED to camera may be a product of the percentage of the incident light that reaches the cell phone camera (0.012%) through the f/45 lens and the percentage of the LED's output that reaches the eardrum's 6 mm target FOV zone (0.35%, as described above), further modulated by the eardrum contrast.

A consideration in imaging optics system design is the control of veiling glare; the impact of out-of-focus stray light leakage to the camera's sensor that reduces image contrast by raising the black level, which may be analogous to watching TV in direct sunlight. Veiling glare, or scatter, may be described as an imperfection in optical instruments (like otoscopes) arising from incoming light that strays from the normal image-forming path. Veiling glare may degrade the contrast of an image by raising the black level in the imagery. The result of veiling glare may be the reduction of the peak-to-peak signal (i.e., contrast) sensed by the detector, resulting in a final image degraded by loss of contrast and reduced definition.

Scatter may come from several sources, including one or more of the following: ambient light leakage between the otoscope package and the cell phone camera's lens aperture, leakage of LED output through mechanical paths in the assembly, leakage of the light pipe losses from TIR failures through the thin-wall lens tube, and/or backscatter from the amount of illumination incident on the speculum's inner surface. The reduction of glare from ambient lighting of LED leakage may be reduced by enhancing the absorbance of the thin-wall lens tube with a carbon filler in the injection molding process. Speculum backscatter may be a contributor (e.g., a significant contributor) to veiling glare is speculum backscatter.

In a situation where a light source is, for example, the camera flash of a smartphone or other fixed or uncontrollable light source, veiling glare may cause poor image quality. This problem may be further extenuated when an otoscope is being used by a consumer or patient, rather than a doctor or medical professional, who is generally unfamiliar with the use of otoscopes and the structure of the outer ear, the middle ear, and/or the ear canal. Good image quality and contrast may help a consumer or patient effectively take an image of the outer ear, the middle ear, and/or the ear canal. The image taken by the consumer or patient may be transmitted to and usable by a medical professional, for example, to diagnose ear problems.

Disclosed herein are optical designs that address veiling glare. The optical designs disclosed herein that provide solutions to veiling glare may be explored in the two examples below: Examples A and B. Example A may be an otoscope design where veiling glare may not be reduced (e.g., there may be suboptimal levels of veiling glare). Example B shows various embodiments of the otoscope design where veiling glare has been reduced and image quality improved.

Figure 11:
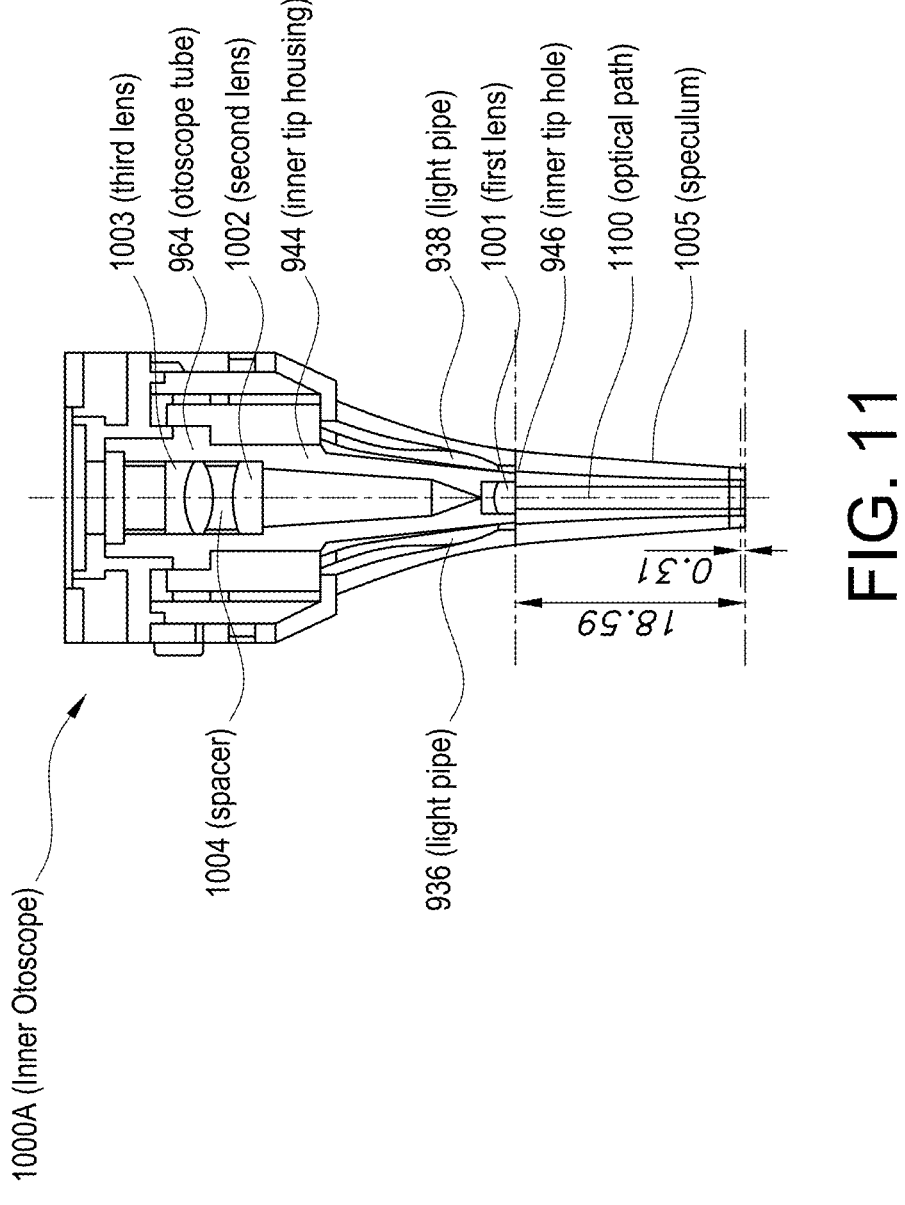
FIG. 11 depicts a cross-section view of an example otoscope that may comprise one or more components.

Example A may be seen in FIG. 11. FIG. 11 shows an embodiment of an inner otoscope 1000A. In an embodiment, one or more light pipes 936/938 may be used to communicate light from a light source to a distal ring portion of the light pipe 936/938 to illuminate a portion of the body or subject (e.g., the ear canal of a patient) to be visualized.

The light source may be an LED on the surface of the smartphone (e.g., a camera flash), or the light source may be housed in the inner otoscope housing 942, as shown in FIG. 9B, for example, on a printed circuit board (PCB). The distal surface of the light pipe 936/938 may be designed to influence the direction of rays from the light pipe toward the surface of the subject being imaged. However, the dispersion of light rays may be more strongly influenced by the angular dispersion of rays exiting the pipe. For example, in a non-tapered pipe, the angular dispersion nearly matches the dispersion at the pipe input. However, the dispersion may be magnified in a tapered pipe (large to small). The light pipe design itself, therefore, may impact the amount of the light pipe's output that is incident on the speculum's wall rather than reaching the eardrum. In one embodiment, the distal surface of the light pipe 936/938 may be a distal ring portion. The distal ring portion may direct light into a coaxial ring light around the camera optics axis denoted in FIG. 11 as dashed line "A."

In one embodiment, an otoscope tube 964, also called a "lens tube" or a "thin-wall lens tube," is a molded, dense black plastic structure that houses and precisely spaces various optical components of the otoscope assembly. According to one embodiment, as shown in FIG. 11, the optical components housed in the otoscope tube 964 may include lenses, for example three lenses 1001/1002/1003, a mid-aperture located behind lens 1001, a spacer 1004, and/or a lens retainer, for example, a compression fit ring. A lens of the three lenses 1001/1002/1003 may comprise an optical material as described herein. The inner tip housing 944 of the otoscope tube 964 may further form a hollow channel in line with the camera optics axis for the image or video capture of the outer ear, the middle ear, and/or the ear canal. The camera optics axis is denoted by the dashed line labeled at 1100 in FIG. 11.

According to one embodiment, lens 1001 may be referred to as an objective lens, lens 1002 may be referred to as a field lens, and lens 1003 may be referred to as an eyepiece lens. The field lens 1002 may be in the vicinity of an intermediate image plane. The eyepiece lens 1003 may deliver the image to the cell phone camera at a near-infinity conjugate. The camera's autofocus system may or may not make final adjustments. The objective lens 1001 and the eyepiece lens 1002 are doublets to minimize chromatic aberrations.

The inner otoscope 1000A may further include a speculum 1005 or multiple specula that may be attached and/or removed by a user to the end of the otoscope tube 964. The specula may come in various shapes and sizes to fit the outer ear, the middle ear, and/or the ear canal of a patient. The camera optics axis at 1100 may run continuously in a straight line through the otoscope tube 964 and the speculum 1005. It should also be noted in this embodiment that the light pipe 936/938 terminates at the same distal end location as the otoscope tube 964, for example, at the inner tip hole 946, both facing towards the outer ear, the middle ear, and/or the ear canal of the subject.

There may only be one aperture in the inner otoscope 1000A. According to one embodiment, the aperture that defines the system stop and f/number may be located behind the proximal end of objective lens 1001. According to another embodiment, the aperture, or aperture stop, may be located at the distal end of the objective lens 1001. According to a further embodiment, two apertures may be placed at both the distal and proximal ends of the objective lens 1001, with one of the apertures defining the system stop and the other allowing only rays directed from the defined field-of-view, thereby nominally blocking stray light from the speculum wall.

According to one embodiment, the light pipe 936/938 may deliver the light source output (e.g., LED output) to the top of the otoscope assembly through total internal reflection (hereinafter "TIR"). As described herein, TIR is defined as the optical phenomenon in which waves (e.g., light) arriving at the boundary from one medium to another are not refracted to the second external medium, but reflected back to the first internal medium. Some of the light source output makes its way through the speculum 1005 of the otoscope and onto the eardrum within the outer ear, the middle ear, and/or the ear canal.

A problem identified with the use of a light pipe configuration is that a small percentage of the LED's output is delivered to the target site in the outer ear, the middle ear, and/or the ear canal. According to one embodiment, the target site may be defined as about 27 mm, about 28 mm, about 29 mm, about 30 mm, about 31 mm, about 32 mm, about 33 mm, about 34 mm or about 35 mm from the distal end of lens 1001 toward the subject in the outer ear, the middle ear, and/or the ear canal. According to one embodiment, the target site may be defined as 31.5 mm±2.3 mm from the distal end of lens 1001 towards the subject in the outer ear, the middle ear, and/or the ear canal. The remaining percentage of the LED's output is incident on the inner wall of the speculum 1005. While nearly all of the speculum 1005 is outside the direct field of view of the imaging optics, reflections off of the speculum 1005 may enter the optics off-axis as scattered light, and some of that scattered light can reach the camera. This may create veiling glare and may reduce image contrast.

According to one embodiment, the lens tube 964 and the speculum 1005 may be partially or entirely colored black to prevent the reflection of light. However, light transmission may still occur, for example, at the thin wall of the lens tube 964, where leakage from the light pipe may be incident on its wall. A carbon black additive to the injection molding process may further reduce transmission. Also, because the speculum 1005 may be tapered, multiple reflections that reach the tip (closest to the field of view) may turn around and reflect back toward the lenses.

To evaluate this issue, the inner otoscope 1000A of FIG. 11 may be tested, for example, using optical CAD software, such as OpticsStudio and/or Zemax Optical CAD. Zemax is a widely accepted optical CAD program, which has two modes of operation: sequential and non-sequential. In the sequential mode, an extensive list of optical surface types can be assembled line-by-line into a representative system model. The dimensional and optical parameters of each surface can be defined or left as a variable. Variables may be optimized through optimization algorithms customized to the goals of the application. Sources and detectors are placed in the models as needed. There is a large library of performance analytics. However, each light ray is traced through the system sequentially and cannot be split or scattered off of any surface more than once. The sequential mode may be useful for detailed lens design, however it may not be suited to custom CAD components and opto-mechanical interactions.

The non-sequential mode, in contrast, may not be well suited to detailed lens design. But a system designed in the sequential mode may be imported into the non-sequential mode and embellished with mechanical detail for interactive analysis. Mechanical CAD entities, such as light pipes or lens mounts, may be created within Zemax or imported from mechanical CAD programs such as SolidWorks. Optical properties may be assigned to selected surfaces or volumes on those CAD structures. Then rays may be traced non-sequentially, back and forth through the system; reflected, absorbed, split and/or scattered in defined fashion. Thus, the non-sequential mode may be used for designing light pipes and evaluating opto-mechanical integrity of a design.

The complexity of designs may be demanding on the computer, especially when the subsystems are somewhat inefficient. Hundreds of thousands of rays may be traced to achieve meaningful results. Model run times may extend into hours, and memory requirements may exceed the capacity of the computer, which may be impactful as this may be an iterative process. A number of procedures may be used to simplify the processes. For example, Mechanical CAD components may be simplified to those surfaces or volumes that interact with light paths. Intermediate results from one process (e.g., an inefficient process) may be simulated to reduce the number or rays to be traced.

An example of this approach may be the simulation of veiling glare. The number of ray traces and the memory and time required to trace from LED simulation, through the light pipe and speculum, to the eardrum and reflecting back through the imaging optics to the camera may be impractical. A reasonable shortcut was to simulate the light pipe optic with a matching annular emitting surface and replace the speculum CAD with a simple conic surface. A simulation run may take 40 minutes, but may yield good comparative results for the placement and sizing of the aperture.

Zemax may allow detector planes to be placed at chosen locations in the optical structure to monitor impacts of design modifications and overall performance. Optical power (lumens) and illuminance (power density: lumens/sq meter, i.e. lux) may be calculated and displayed by the system. A false color format may be chosen to illustrate performance.

As noted herein, the evaluation of system glare using Zemax may be difficult to model in terms of absorption, reflectance, and surface finish. For example, while Zemax may model complex surface parameters, the parameters of the inner wall of the speculum may not be well specified and may or may not be consistently controlled in the molding process. Thus, simulations represent a reasonable approximation.

Figure 12A:
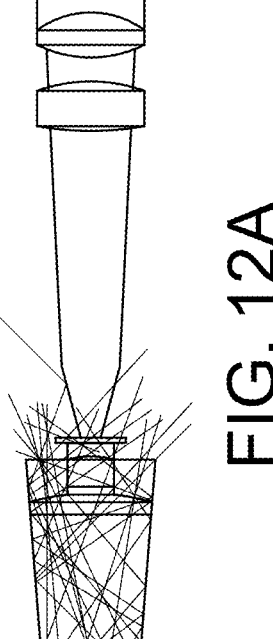
FIGS. 12A-12B depict exemplary simulation model results to evaluate otoscope system glare of an example otoscope.
Figure 12B:
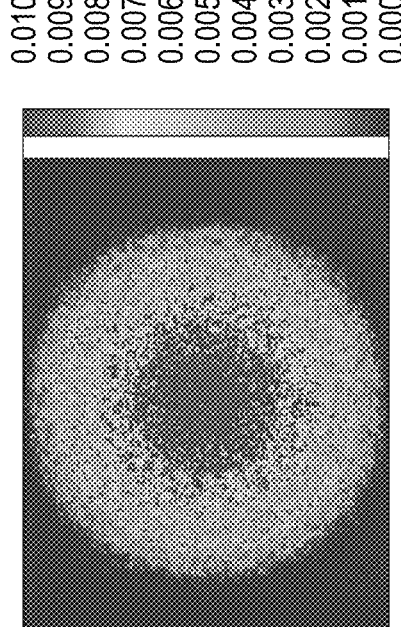

Furthermore, it may not be possible to trace enough rays directly from the LED, through the light pipe and speculum, to the target site because of the problem herein above regarding the small percentage of LED output that makes the target site. To accommodate these limitations, as noted above, a blended model may be used with one or more of the following: a diffuse annular emitter representing the light pipe output, a conic section representative of the interior surface of the speculum, and the imaging optics. The results may be superimposed on a camera chip. The results of this simulation for evaluating scattered light and glare in exemplary inner otoscope 1000A are depicted in FIGS. 12A and 12B. These results show illumination rays filling the speculum with a few exiting toward the eardrum and some being back-reflected towards the lenses.

The model simulated the embodiment (e.g., Example A) as shown in FIG. 11, where a 0.7 mm aperture may be located at the conic tip of the lens tube 964 directly behind lens 1001. The Zemax results of this simulation are shown in FIGS. 12A and 12B. In this simulation, the size of the subject test area was 4.580 mm wide by 3.440 mm high, corresponding to a cell phone camera chip and modeled 1000 pixels wide by 1000 pixels high. The total power was 0.544 mW (milliwatts). Visually, the amount of scatter reflected in the subject image can be seen in FIG. 12B. This amount of scatter, or veiling glare, will reduce image contrast and quality when used to capture images of the outer ear, the middle ear, and/or the ear canal. Thus, this amount of scatter may be reduced to provide an otoscope device that may effectively capture images or video of the outer ear, the middle ear, and/or the ear canal.

Structural features, such as bumps, on the housing may help position the light pipe while also decoupling the light pipe from the inner housing to prevent absorption of light by the housing. Additionally, black coatings on internal surfaces of the inner housing or carbon black added into the injection molding process of the otoscope may be used to minimize stray light. However, as discussed herein, true black may not be achievable and light transmission still occurs. These options were tested on the inner otoscope 1000A as shown in FIG. 11, however, Example A may be inadequate to reduce the veiling glare to acceptable levels.

Example B shows various embodiments of the otoscope design where veiling glare has been reduced and image quality improved.

Figure 13:
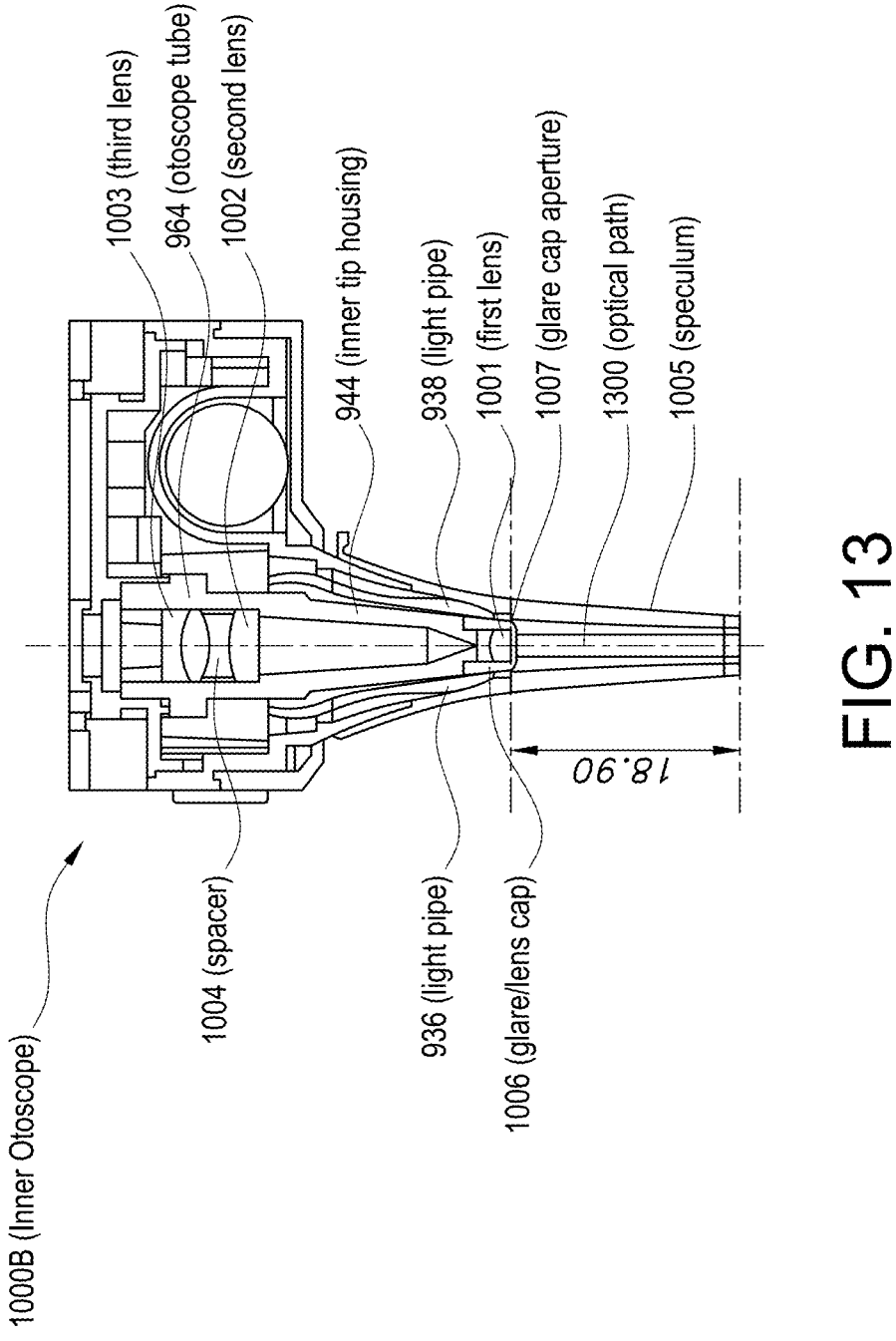
FIG. 13 depicts a cross-section view of another example otoscope that may comprise one or more components.
Figures 14A, 14B, 14C:
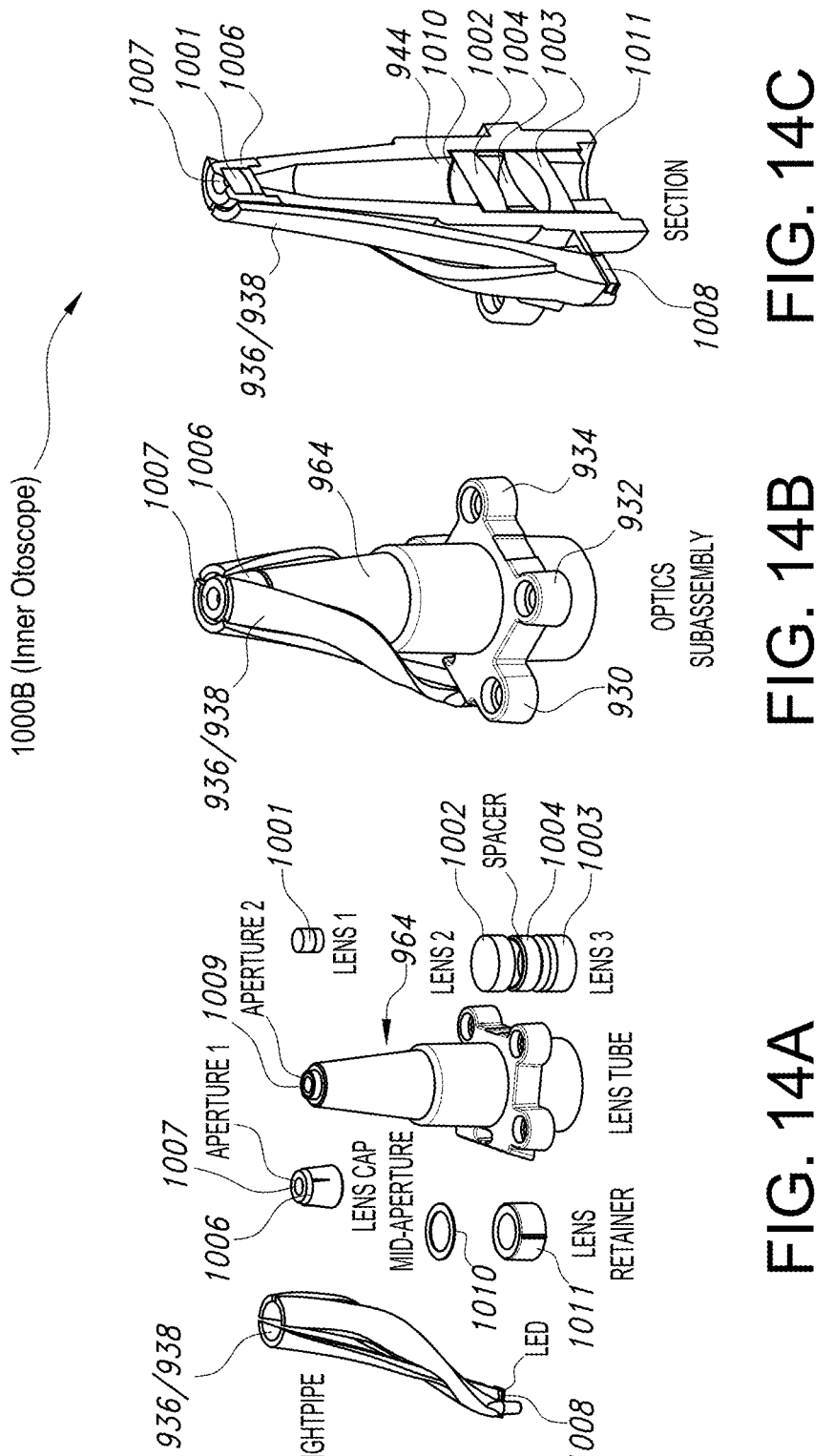
FIGS. 14A-14D depict perspective exploded, sub-assembly, cross-section and schematic views of an example otoscope that may comprise one or more components.
Figure 14D:
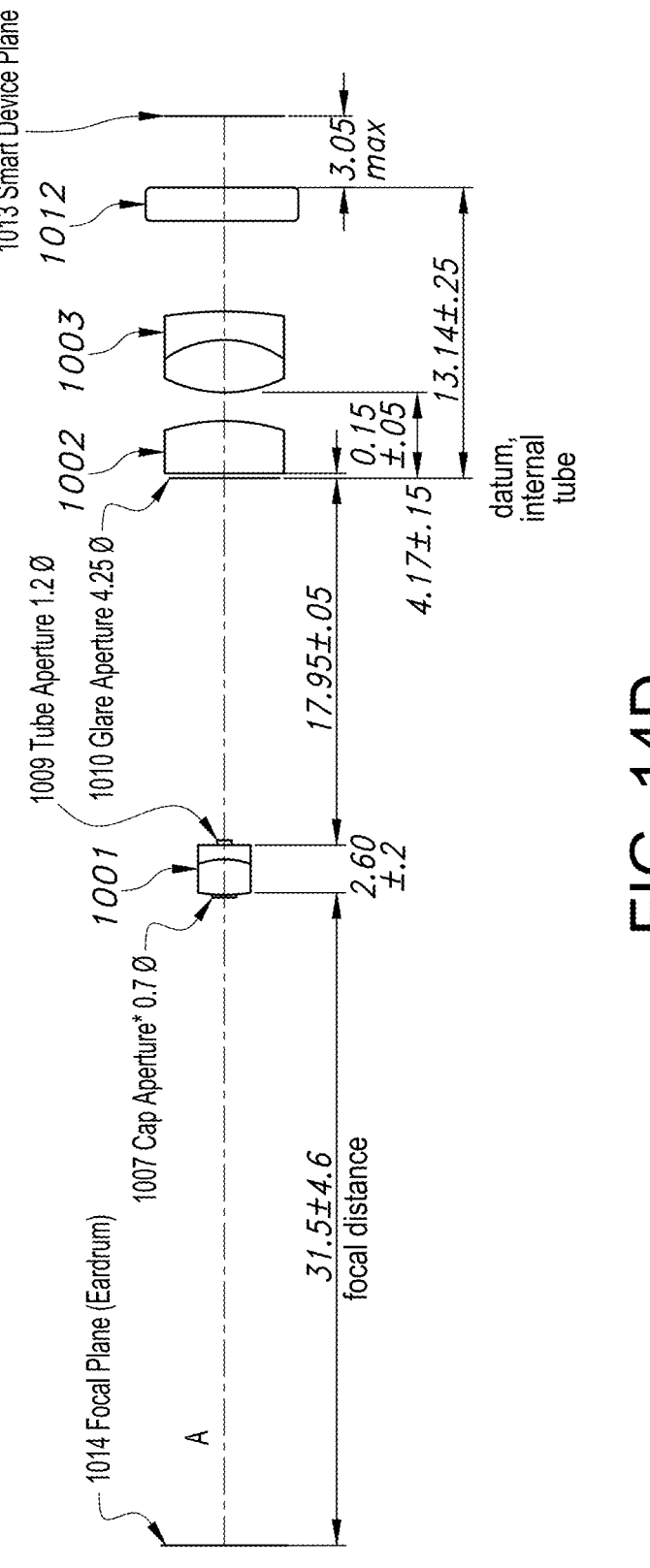

To resolve the veiling glare issues shown and described in Example A above, exemplary embodiments, as shown here in Example B, were developed. In particular, FIG. 13 shows an inner otoscope 1000B design with reduced veiling glare and improved image quality. Further, FIG. 14A is an exploded view of the inner otoscope 1000B of FIG. 13. FIG. 14B depicts an optics subassembly of the inner otoscope 1000B of FIG. 13. FIG. 14C is a section view of the inner otoscope 1000B of FIG. 13. FIG. 14D is a schematic diagram of the optical layout of FIG. 13.

In the embodiment shown in FIG. 13, a light pipe(s) 936/938 may be used to communicate light from a light source to a distal ring portion of the light pipe(s) 936/938 to illuminate a portion of the body or subject (e.g., the ear canal of a patient) to be visualized. The light source may be an LED on the surface of the smartphone (e.g., a camera flash), or the light source may be housed in the inner otoscope housing 942, for example an LED 1008 on a printed circuit board (PCB). The distal surface of the light pipe(s) 936/938 may be designed to direct rays from the light pipe toward the surface or subject being imaged. In one embodiment, the distal surface of the light pipe(s) 936/938 may be a distal ring portion. The distal ring portion may direct light into a ring light or coaxial ring around the camera axis optical axis as denoted in FIG. 13 by dashed line at 1300.

According to an embodiment, as shown in FIGS. 13 and 14A-D, the optical components housed in the otoscope tube 964 may include two lenses 1002/1003, mid-aperture 1010, spacer 1004, and/or lens retainer 1011. The first lens 1001 may be positioned in a separate glare cap 1006, also called a "lens cap," having a separate glare cap aperture 1007. The glare cap 1006 may be adapted to fit and/or snap into the end of the otoscope tube 964 and may retain lens 1001 in place, for example, without the use of glue. As the first lens 1001 may be referred to as the objective lens, the second lens 1002 may be referred to as the field lens, and the third lens 1003 may be referred to as the eyepiece lens.

The first lens 1001 may comprise an optical material, such as the optical materials described herein. The optical material may be glass. The first lens 1001 may be an objective lens that may be used to collect light from an object and focus it onto an image plane. The first lens 1001 may be responsible for forming an image of the object being viewed. The first lens 1001 may be the lens closest to the viewed object and may be located at one end of the optical system.

The first lens 1001 may be a converging lens and may be referred to as a positive lens. The first lens 1001 may comprise one or more lenses, which may have different indices and/or different shapes. For example, the first lens 1001 may be a doublet lens that comprises a biconvex lens of a first index and a plano-concave lens of a second index. A doublet lens may be used to provide (e.g., achieve) chromatic correction.

The second lens 1002 may comprise an optical material, such as the optical materials described herein. The optical material may be glass. The second lens 1002 may be a field lens, which may be used to correct for aberrations or distortions in an image over a field of view (e.g., a wide field of view). The second lens 1002 may be used to direct light (e.g., more light) into the eyepiece lens that would otherwise be directed to the wall of the lens tube. The second lens 1002, may be placed in the intermediate image plane of the optical system, between the objective lens (e.g., the first lens 1001) and the eyepiece (e.g., 1003).

The second lens 1002 may be a converging lens and may be referred to as a positive lens. The second lens 1002 may comprise one or more lenses, which may have different indices and/or different shapes. For example, the second lens 1002 may be a plano-convex lens of an index.

The third lens 1003 may comprise an optical material, such as the optical materials described herein. The optical material may be glass. The third lens 1003 may be an eyepiece lens. The third lens 1003 may collimate the light toward the eye or camera to form a near-infinite conjugate.

The third lens 1003 may be used to magnify an image. Magnification may be accomplished by the ratio of the eyepiece lens focal length and the objective lens focal length. For example, third lens 1003 (e.g., the eyepiece lens) may be used in conjunction with the first lens 1001 (e.g., the objective lens) to magnify the image formed by the objective lens and/or make the image easier to see.

The third lens 1003 may be a converging lens and may be referred to as a positive lens. The third lens 1003 may comprise one or more lenses, which may have different indices and/or different shapes. For example, the third lens 1003 may be a doublet lens that comprises a biconvex lens of a first index and a convex-concave lens of a second index. A doublet lens may be used to provide (e.g., achieve) chromatic correction.

According to another embodiment, the otoscope tube 964 and glare cap 1006 may have different lens configurations. For example, the otoscope tube 964 may have one, two, three, four, five and up to ten lenses. The glare cap 1006 may house zero, one, two, three, four, five and up to ten lenses. The ratio of lenses in the otoscope tube 964 as compared to lenses housed in the glare cap 1006 may be 1:1, 2:1, 3:1, or, alternatively, may be 1:2 or 1:3.

Unlike the inner otoscope 1000A exemplified in FIG. 11, the light pipe 936/938 in inner otoscope 1000B may not terminate at the distal end of the otoscope tube 964. Rather, the light pipe 936/938 of inner otoscope 1000B terminates either at or slightly before the distal end of glare cap 1006. Both the otoscope tube 964 and the glare cap 1006 may be the color black, or another dark color, to prevent the transmission of light from the light pipe 936/938 into the inner tip housing 944 of the otoscope tube 964. This configuration can be seen in FIG. 14B.

As shown in FIGS. 14A-C, the proximal end of light pipe 936/938 extends from LED 1008, wraps around the exterior of both the otoscope tube 964 and the glare cap 1006, and terminates at a distal end to project the light into the outer ear, the middle ear, and/or the ear canal of the patient. As shown in FIG. 14B, the light pipe 936/938 may terminate before, or prior to, the distal end of the glare cap 1006 to minimize any glare back in towards the aperture. This early termination may prevent the inadvertent transmission of light from the light pipe 936/938 into the otoscope tube 964 and/or the glare cap 1006. This reduces veiling glare issues, as discussed herein with regard to Example A.

The glare cap 1006 may be used to protect one or more lenses of the otoscope. The glare cap 1006 may be used to reduce and or prevent veiling glare issues, as described herein. The glare cap 1006 may be made of a durable material, such as plastic or metal, and may be designed to fit over the first lens 1001. For example, the glare cap 1006 may be designed to fit within light pipe 936/938 and over the first lens 1001. The glare cap 1006 may be used to protect the lens when the otoscope is used, for example, by protecting a lens, such as the first lens 1001, when exposed to dust, biomaterial, water, and/or the like. The glare cap 1006 may be designed to provide (e.g., achieve) a precise alignment of the objective lens within the optical system.

In an embodiment, there may be at least one, at least two, or at least three apertures in the inner otoscope assembly. The at least one aperture may have a diameter from about 0.5 mm to about 4.5 mm, or in particular from about 0.7 mm to about 4.25 mm. According to one embodiment, the at least one aperture may have a diameter of about 0.7 mm, and/or about 1.2 mm, and/or about 4.25 mm.

According to the embodiment shown in FIGS. 14A-14C, there may be three apertures in the inner otoscope 1001B subassembly. A first glare cap aperture 1007, which may be referred to as a lens cap aperture (e.g., lens cap aperture 1007), may be present at the distal end of the glare cap 1006 facing the inner ear of the subject. The glare cap 1006 may be referred to as a lens cap (e.g., lens cap 1006). According to one embodiment, the glare cap aperture 1007 may be approximately 0.7 mm in diameter. A second tube aperture 1009 may be present at the distal end of the otoscope tube 964 and directed towards the proximal end of glare cap 1006. According to one embodiment, the tube aperture 1009 may be approximately 1.2 mm in diameter. A third aperture, called a mid-aperture 1010 or a glare aperture, may be defined by a compression fit ring or the like positioned on the distal side of lens 1002. The mid-aperture 1010 may be a thin material held in place between the lens 1002 and a step in the inner tip housing 944. This may be the approximate location of the intermediate image plane. According to one embodiment, the mid-aperture 1010 may be approximately 4.25 mm in diameter. The ratio of the glare cap aperture 1007 to the tube aperture 1009 may be about 1:2, or about 0.7:1.2. For example, the ratio of the diameter of the glare cap aperture 1007 to the diameter of the tube aperture 1009 may be about 0.7:1.2. The ratio of the tube aperture 1009 to the mid-aperture 1010 may be about 1:4, or about 1.2:4.25. For example, the ratio of the diameter of the tube aperture 1007 to the diameter of the tube aperture 1009 may be about 1.2:4.25. The ratio of the glare cap aperture 1007, tube aperture 1009 and mid-aperture 1010 may be about 0.7:1.2:4.25. For example, the ratio of the diameter of the glare cap aperture 1007, the diameter of the tube aperture 1009, and the diameter of the mid-aperture 1010 may be about 0.7:1.2:4.25. Other aperture configurations are possible, including the use of one, two, three, four, five and up to ten apertures. The apertures may provide specific photographic functions and advantages, for example, when paired with the use of a smartphone camera.

For example, although not shown in FIGS. 14A-14C, according to one embodiment, the glare cap aperture 1007 may be approximately 1.2 mm in diameter. A second tube aperture 1009 may be present at the distal end of the otoscope tube 964 and directed towards the proximal end of glare cap 1006. The tube aperture 1009 may be approximately 0.7 mm in diameter. The mid-aperture 1010 may be approximately 4.25 mm in diameter. The ratio of the glare cap aperture 1007 to the tube aperture 1009 may be about 2:1, or about 1.2:0.7. For example, the ratio of the diameter of the glare cap aperture 1007 to the diameter of the tube aperture 1009 may be about 1.2:0.7. The ratio of the tube aperture 1009 to the mid-aperture 1010 may be about 1:6, or about 0.7:4.25. For example, the ratio of the diameter of the tube aperture 1007 to the diameter of the tube aperture 1009 may be about 0.7:4.25. The ratio of the glare cap aperture 1007, tube aperture 1009 and mid-aperture 1010 may be about 1.2:0.7:4.25. For example, the ratio of the diameter of the glare cap aperture 1007, the diameter of the tube aperture 1009, and the diameter of the mid-aperture 1010 may be about 1.2:0.7:4.25.

Referring again to FIGS. 14A-14C, according to an embodiment, two apertures 1007/1009 may be placed at both the distal and proximal ends of objective lens 1001, with one of the apertures defining the system stop and the other allowing only rays directed from the defined field-of-view, thereby nominally blocking stray light from the speculum wall. According to a further embodiment, a third aperture, referred to as a mid-aperture 1010 may be placed in proximity to the intermediate image at the distal end of the field lens 1002. The third aperture may act as a baffle to block reflected light from the wall of inner tip housing 944. The third aperture may cause the field-of-view to be more crisply defined.

In simplified detail, a smartphone camera uses a convex lens to focus incoming light into a sensor. The sensor then digitizes the light and turns it into a digital photograph (e.g., a JPEG photo) that is saved on the smartphone. Early camera phones used a fixed-focus lens, which often led to blurry images that were not able to capture large amounts of detail. Many of today's smartphones include an autofocus feature that automatically adjusts the lens to move back and forth so as to vary the distance between the lens and the sensor. This has enabled the capture of sharper images. The autofocus feature of a smartphone camera may be beneficial and/or detrimental when coupling the smartphone camera to an external device, for example an otoscope as described herein. As an advantage, the autofocus feature may enhance the effective working distance from the speculum to the eardrum. However, as a disadvantage, the autofocus feature may continue to "hunt" or readjust the lens making image capture of the outer ear, the middle ear, and/or the ear canal difficult for the user of the otoscope described herein. This autofocus issue is especially likely because it will be hard for the user to hold the smartphone, and attached otoscope assembly, stable or still during use. A movement by the user may prompt the autofocus mechanism to start hunting. And embodiments described herein may include design features to prevent autofocus from interrupting the otoscope use. One such design feature of the optical design is f-number, which is discussed in greater detail below.

For example, according to one embodiment, the glare cap aperture 1007 may be positioned in the glare cap 1006 to define a system f-number, which determines the resolution and depth of field, as in photography. The f-number of an optical system is a dimensionless number that provides a qualitative measure of lens speed, calculated by the ratio of the system's focal length to the diameter of the entrance pupil (or "clear aperture"). The f-number may also be referred to as the focal ratio, f-ratio or f-stop. Depth of field is defined as the distance between the closest and farthest objects in a photo that appears acceptably sharp. Thus, a properly defined depth of field will allow a user to see and capture a sharp image.

An autofocus system may be aided and/or assisted by preventing it from hunting while trying to focus. For example, an aperture of the optical system may be adjusted to minimize, circumvent, disable, and/or avoid hunting altogether. For example, this may be done by increasing a depth of field of the optical system to enable the autofocus system to focus on a subject rapidly and accurately. The aperture for the autofocus system may vary depending on the particular model, but in general, selecting a smaller aperture (e.g., a smaller diameter and a high f-number) may help minimize and/or eliminate hunting.

According to an embodiment, the first aperture 1007 may have a small diameter (and high f-number) to assist the autofocus system of a smartphone. For example, the first aperture 1007 may be of a diameter (a smaller diameter and high f-number) that may minimize the hunting of a smartphone's autofocus system. According to one embodiment, the diameter of the first aperture 1007 may be, for example, about 0.7 mm, and the nominal distance from the aperture to the eardrum, may be, for example, about 31.5 mm. The system f-number of the first aperture 1007, therefore, may be the ratio of the working distance to the aperture diameter (e.g., 31.5 mm/0.7 mm) which, in this example, is about 45 (denoted as "f/45"). The high f-number provided by the first aperture 1007 may assist the smartphone autofocus system by creating a larger in-focus volume and allow the user to easily capture a sharp image of the outer/middle ear without continuous and frustrating readjustment, i.e., hunting, of the smartphone camera lens.

According to an embodiment, the first aperture 1007 may be of a diameter to provide a depth of field that may be past the tip of a speculum. For example, the first aperture 1007 may assist the autofocus system of the smartphone by assisting or allowing the autofocus system to focus on a point past the speculum tip (e.g., focus at or near infinity).

According to an embodiment, the first aperture, second aperture, and third aperture may have a diameter between 0.5 mm and 4.5 mm. In an example, the first aperture may have a diameter of about 0.7 mm, the second aperture may have a diameter of about 1.2 mm, and the third aperture may have a diameter of about 4.25 mm. In an example, a ratio of a diameter of the first aperture to a diameter of the second aperture may be about 1:2, and/or a ratio of a diameter of the second aperture to a diameter of the third aperture may be about 1:4.

According to an embodiment, the second aperture 1009 may have a small diameter (and high f-number) to assist the autofocus system of a smartphone. For example, the second aperture 1009 may be of a diameter (a smaller diameter and high f-number) that may minimize the hunting of a smartphone's autofocus system. According to one embodiment, the diameter of the second aperture 1009 may be, for example, about 0.7 mm, and the nominal distance from the aperture to the eardrum, may be, for example, about 34.1 mm (e.g., 31.5 mm+2.6 mm). The system f-number of the second aperture 1009, may be the ratio of the working distance to the aperture diameter (e.g., 34.1 mm/0.7 mm) which, in this example, is about 49 (denoted as "f/49"). The high f-number provided by the second aperture 1009 may assist the smartphone autofocus system by creating a larger in-focus volume and allow the user to easily capture a sharp image of the outer/middle ear without continuous and frustrating readjustment, i.e., hunting, of the smartphone camera lens.

According to an embodiment, the second aperture 1009 may be of a diameter to provide a depth of field that may be past the tip of a speculum. For example, the second aperture 1009 may assist the autofocus system of the smartphone by assisting or allowing the autofocus system to focus on a point past the speculum tip (e.g., focus at or near infinity).

According to an embodiment, the second aperture 1009 may be of a diameter to provide a depth of field that may be past the tip of a speculum. The first aperture 1007 may be slightly larger than the second aperture 1009. The first aperture 1007 may be slightly larger than the second aperture 1009 to prevent obscuring peripheral rays. For example, the second aperture 1009 may be about 0.7 mm, and the first aperture may be about 0.75 mm.

According to an embodiment, the first aperture, second aperture, and third aperture may have a diameter between 0.5 mm and 4.5 mm. In an example, the first aperture may have a diameter of about 1.2 mm, the second aperture may have a diameter of about 0.7 mm, and the third aperture may have a diameter of about 4.25 mm. In an example, a ratio of a diameter of the first aperture to a diameter of the second aperture may be about 2:1, and/or a ratio of a diameter of the second aperture to a diameter of the third aperture may be about 1:6.

According to an embodiment, a second tube aperture 1009 at the proximal end of the otoscope tube 964 may provide a narrow tunnel into the remaining optics to minimize glare that degrades contrast from light scattered off of the interior of the speculum 1005. The tube aperture 1009 may be, for example, about 1.2 mm in diameter. A third aperture, referred to as a mid-aperture 1010, may block grazing incidence scatter from the interior of the lens tube and may serve to better define the perimeter of the field of view. The third aperture 1010 may be, for example, about 4.25 mm in diameter. The field of view is defined as the maximum area visible when looking through the otoscope. In the present case, the field of view may be, for example, approximately 6 mm in diameter at a nominal working distance of about 31.5 mm; e.g., an angular field of view of 10.9 degrees.

According to one embodiment, the otoscope subassembly shown in FIGS. 14A-14C are designed to fit together without the use of adhesives in proximity to the lenses.

FIG. 14D depicts a schematic diagram of the optical design of FIG. 13. The schematic diagram shows the order of the optical elements, as well as the distances between them according to one embodiment of the invention. According to FIG. 14D, viewing the diagram from right to left, the rear window 1012 of the otoscope assembly may be distanced a maximum of 3.05 mm from the smart device plane 1013. The smart device plane is another descriptor for the front surface of a smart device, such as a smartphone, against which the otoscope is attached.

Working again from right to left, the third lens 1003, the second lens 1002 and first lens 1001, respectively known as the eyepiece lens, the field lens, and the objective lens, are positioned, respectively, in parallel to the rear window 1012 along the optical axis A. According to one embodiment, the distance between the proximal end of the rear window 1012 to the distal end of the second lens 1002 is about 13 mm, in particular, about 13.14±0.25 mm. This distance may correlate to the length of the internal lens tube. According to one embodiment, the distance between the distal end of the third lens 1003 to the distal end of the second lens 1002 is about 4 mm, in particular, about 4.17±0.15 mm. According to one embodiment, the distance between the distal end of second lens 1002 and the proximal end of first lens 1001 is about 18 mm, in particular, about 17.95±0.05 mm. According to one embodiment, the length of the first lens is about 2.5 mm, in particular, about 2.6±0.2 mm.

FIG. 14D further depicts an embodiment of the three apertures of the inner otoscope 1000B of FIG. 13. Viewing from right to left, the mid-aperture (or glare aperture) 1010 may have a diameter of about 4.25 mm and may be positioned about 0.15±0.05 mm from the distal end of second lens 1002. The tube aperture 1009 may have a diameter of about 1.2 mm and may be positioned on the proximal end of the first lens 1001. The glare cap aperture 1007 has a diameter of about 0.7 mm and is positioned on the distal end of first lens 1001. The space between the glare cap aperture 1007 to the tube aperture 1009 is about 2.60±0.2 mm, which may or may not correlate with the length of the first lens 1001 along the optical axis.

The focal distance, or nominal working distance, between the glare cap aperture 1007 and/or the distal end of lens 1001 to the focal plane (e.g., the eardrum) may be about 26, about 26.5, about 27, about 27.5, about 28, about 28.5, about 29, about 29.5, about 30, about 30.5, about 31, about 31.5, about 32, about 32.5, about 33, about 33.5, about 34, about 34.5, about 35, about 35.5, about 36 or about 36.5 mm. According to one embodiment, the focal distance may be about 31.5±4.6 mm.

According to one embodiment, the light source is a white light LED chosen for efficacy and color temperature suitable to illuminate the outer/middle ear (e.g., an ear canal). Other light sources may be applicable to the illumination of other portions of the body.

According to one embodiment, the light pipe 936/938 delivers the light source output (e.g., LED output) to the top of the otoscope assembly through total internal reflection (hereinafter "TIR"). TIR is defined as the optical phenomenon in which waves (e.g., light) arriving at the boundary from one medium to another are not refracted to the second external medium, but completely reflected back to the first internal medium. Some of the light source output makes its way through the speculum 1005 of the otoscope and onto the eardrum within the outer/middle ear canal.

As discussed before, a problem identified with the use of a light pipe configuration is that only a small percentage of the LED's output may be delivered to the target site in the outer ear, the middle ear, and/or the ear canal. According to one embodiment, the target site may be defined as approximately 31.5 mm from the distal end of first lens 1001 towards the outer ear, the middle ear, and/or the ear canal. A portion of the LED's light output may not be captured by the input aperture of the light pipe. For example, not all of the LED's light output may be captured by the input aperture of the light pipe. Some of the LED's output may be lost through the light pipe due to TIR failures of some light rays. Some percentage of the LED's output may be incident on the inner wall of the speculum. While a portion (e.g., nearly all) of the speculum may be outside the direct field of view of the imaging optics, reflections off of the speculum may enter the optics off-axis as scattered light and some of that scattered light may reach the camera. This may create veiling glare and consequently a reduction of image contrast. Although, the specula may be colored black or manufactured with black carbon filler to prevent the reflection of light, true black may not be possible and light transmission may still occur in bright ambient lighting. Also, because the specula may be tapered, multiple reflections that reach the tip (closest to the field of view) may turn around and reflect back toward the lenses.

Figure 15A:
FIGS. 15A-15B depict additional exemplary simulation model results to evaluate otoscope system glare of an example otoscope.
Figure 15B:
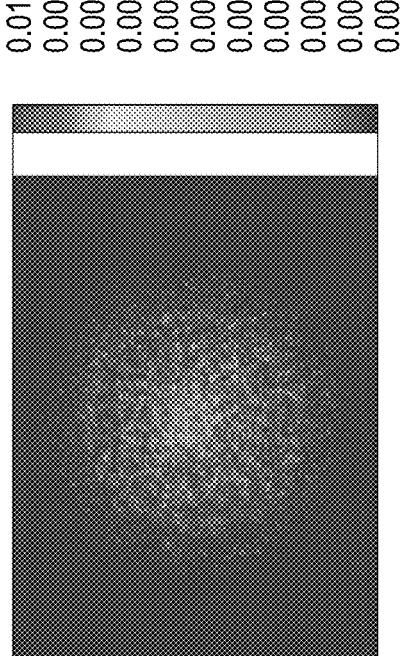

The use of a glare cap 1006 and the provided aperture 1007/1009/1010 configuration may reduce scatter and/or veiling glare in the inner otoscope 1000B. This embodiment, as, for example, shown in FIGS. 13 and 14A-D, was also tested using CAD software, such the Zemax Optical CAD discussed herein. The results of a simulation are depicted in FIGS. 15A to 15B. These results show illumination rays filling the speculum with a few exiting toward the eardrum and some being back-reflected towards the lenses. Some of the rays may make it through the optical system to the camera.

This simulation is of Example B, which is described herein, for example as shown in FIGS. 13 and 14A-D including lens cap 1006 and/or apertures 1007/1009/1010. This embodiment may include a 0.7 mm diameter glare cap aperture 1007 in front of lens 1001 (facing towards the subject to be imaged), a 1.2 mm diameter tube aperture 1009 behind lens 1001, and a 4.25 mm diameter mid-aperture 1010 in front of lens 1002. The results of this simulation may be seen in FIGS. 15A and 15B. As seen in the results, the lens cap 1006 and/or the associated apertures 1007/1009/1010 may create a tunnel that minimizes off-axis scatter from getting through to the camera.

The results of this simulation are shown in FIGS. 15A and 15B. In this simulation, the size of the subject test area was 4.580 mm wide by 3.440 mm high, which may correspond to a cell phone camera chip (e.g., and modeled to 1000 pixels wide by 1000 pixels high). The total power was 0.043 mW.

Visually, the amount of scatter reflected in the subject image may be seen in FIG. 15B, which is less than (e.g., significantly less than) that shown in FIG. 12B from Example A.

Based on the total power calculated by each simulation, i.e., 0.544 mW from Example A and 0.043 mW from Example B, the Example B design has reduced glare by approximately 92%. This reduction in veiling glare may be explained by noting that the intensity of the light being scattered in the speculum exceeds (e.g., far exceeds) the intensity of the image being returned by the eardrum, and it may backscatter into the imaging optics over a large angle (e.g., very large angle—nearly hemispherical). The Example A design had its aperture placed behind the objective lens 1001 and backscatter (e.g., significant backscatter) was reflected off of the lens' ground glass sidewalls, fractionally entering through the aperture into the lens tube. Direct ray paths and internal lens tube reflections result in veiling glare (e.g., significant veiling glare). Moving the first aperture 1007 into the lens cap 1006 and to the distal end of objective lens 1001 may reduce glare. A second aperture 1009 may be added in the original position, at the proximal end of the objective lens 1001, which may be slightly larger than the first aperture 1007 to avoid contributing to diffractive effects, to create a tunnel effect blocking wide-angle backscatter. A third large aperture 1010 may be placed in the vicinity of the intermediate image plan in front of (i.e., distal to) the field lens 1002 to reduce any grazing incidence reflections from the lens tube and to more clearly define the border of the field of view.

Figures 16A, 16B:
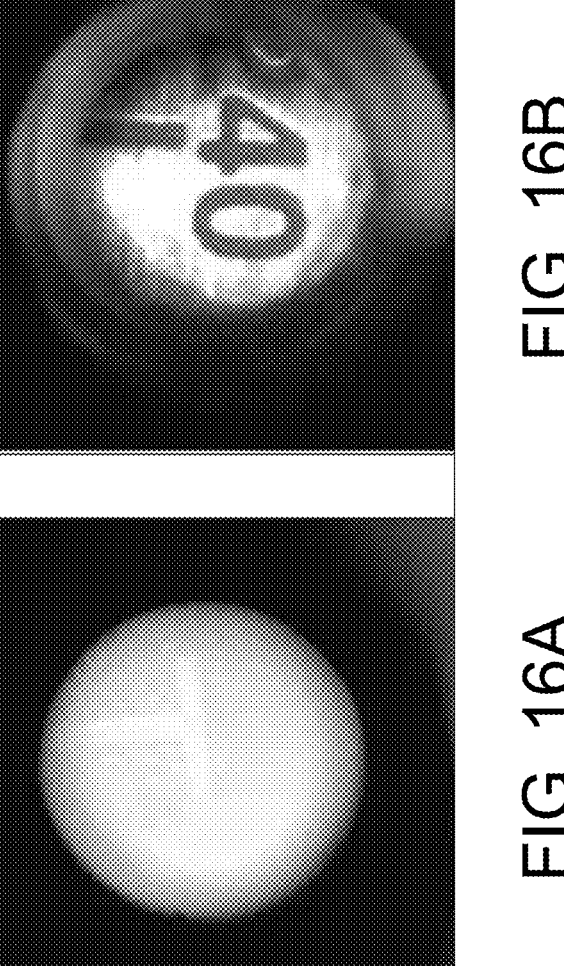
FIGS. 16A-16B depict example images taken using the exemplary otoscope devices disclosed herein.

The embodiment shown in Example B reduces scatter and/or veiling glare, as compared to the embodiment shown in Example A. FIGS. 16A and 16B further exemplify the advantages of Example B. The image contrast quality is improved (e.g., greatly improved) in FIG. 16B through the reduction of veiling glare in the speculum of the inner otoscope device 1000B of FIGS. 13 and 14A-D, as compared to the image contrast quality shown in FIG. 16A as related to the inner otoscope configuration 1000A of FIG. 11. This enhancement of image contrast quality may allow a user to easily capture an image or video of the outer ear, the middle ear, and/or the ear canal. Such an image may be sent to a healthcare professional for evaluation and/or diagnosis. Without high image quality, such an application of tele-otoscopy may not be feasible.

Figure 17:
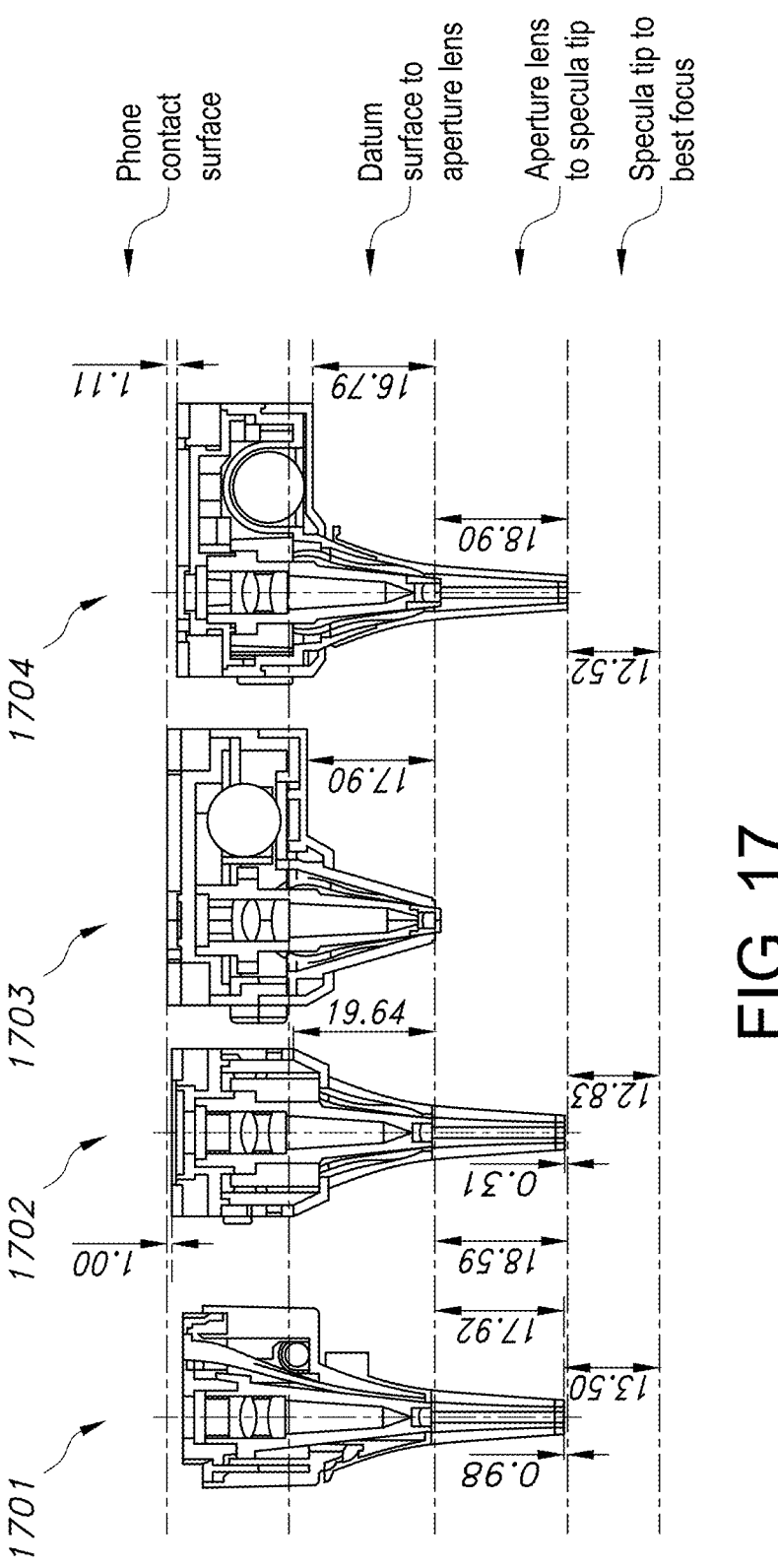
FIG. 17 depicts cross-sectional views of various exemplary otoscope configurations, including the arrangement and distance between optical elements.

Embodiments disclosed herein may be designed to consider one or more system dimensions. Other factors may also contribute to the image or video taken by an otoscope device releasably attached to a smartphone camera. For example, the distance and alignment of the various optical components of the otoscope device to the subject (e.g., outer ear, the middle ear, and/or the ear canal of a patient) may be optimized to produce higher image quality. For example, the distances between the datum surface to the aperture lens, the aperture lens to the speculum tip, and the speculum tip to a point of focus (e.g., a point of best focus). Even the distance between the otoscope and the contact surface of the smartphone may contribute to image quality. Such embodiments are shown in FIG. 17.

According to one embodiment, the otoscope device may be spaced about 0.5, 1 or 1.5 mm away from the surface of the smartphone. According to another embodiment, the otoscope device may be positioned flush or directly against the surface of the smartphone surface with no measurable gap between them.

According to another embodiment, the distance between the datum surface to the aperture lens may be about 16, 16.5, 17, 17.5, 18, 18.5, 19, 19.5 or 20 mm. The distance between the aperture lens to the speculum tip may be about 17, 17.5, 18, 18.5, 19 or 19.5 mm. According to another embodiment, the speculum tip may be positioned about 12, 12.5, 13, 13.5 or 14 mm from the subject for a point of focus (e.g., a point of best focus).

According to one embodiment, an otoscope device 1701 may have a distance of about 18 mm, for example about 17.92 mm, between the aperture lens and the speculum tip. The speculum tip may be about 13.5 mm away from a point of focus (e.g., a point of best focus).

According to another embodiment, an otoscope device 1702 may be distanced about 1.0 mm from the smartphone contact surface. According to an embodiment, the distance between the datum surface to the aperture lens may be about 19.5 or about 20 mm, for example about 19.64 mm, from the aperture lens. According to another embodiment, the aperture lens may be at a distance of about 18, about 18.5 or about 19 mm, for example about 18.59 mm, from the speculum tip. The speculum tip may be about 12.5 or 13 mm, for example about 12.83 mm, from a point of focus (e.g., a point of best focus).

According to an embodiment, the datum surface of the otoscope device 1703 may be about 17.5 or about 18 mm, for example, about 17.90 mm, from the aperture lens. The otoscope device 1703 may be pressed directly against the smartphone contact surface. Otoscope device 1703 may include the glare cap 1006 and/or the apertures 1007/1009/1010 of Example B.

According to another embodiment, the otoscope device 1704 may be positioned about 1 mm, for example about 1.11 mm, from the smartphone contact surface. The datum surface to the aperture lens of otoscope device 1704 may be about 16.5 or about 17 mm, for example about 16.79 mm. The distance between the aperture lens to the speculum tip may be about 18.5 or about 19 mm, for example about 18.90 mm. The distance between the speculum tip to the subject may be about 12.5 or about 13 mm, for example about 12.52 mm. Otoscope device 1704 may include the glare cap 1006 and/or the apertures 1007/1009/1010 of Example B.

The orientation of otoscope devices 1701, 1702, 1703 and 1704 are further summarized in the Table below:

TABLE 1

| Otoscope Device Embodiment # | 1701 | 1702 | 1703 | 1704 |
|---|---|---|---|---|
| Distance to phone contact surface (mm) | | 1.0 | 0 | 1.11 |
| Distance from datum surface to aperture lens (mm) | | 19.64 | 17.90 | 16.79 |
| Distance from aperture lens to speculum tip (mm) | 17.92 | 18.59 | | 18.9 |
| Distance from speculum tip to point of best focus (mm) | 13.5 | 12.83 | | 12.52 |

Other embodiments may include features from one or all of otoscope devices 1701, 1702, 1703 and 1704.

Figure 18:
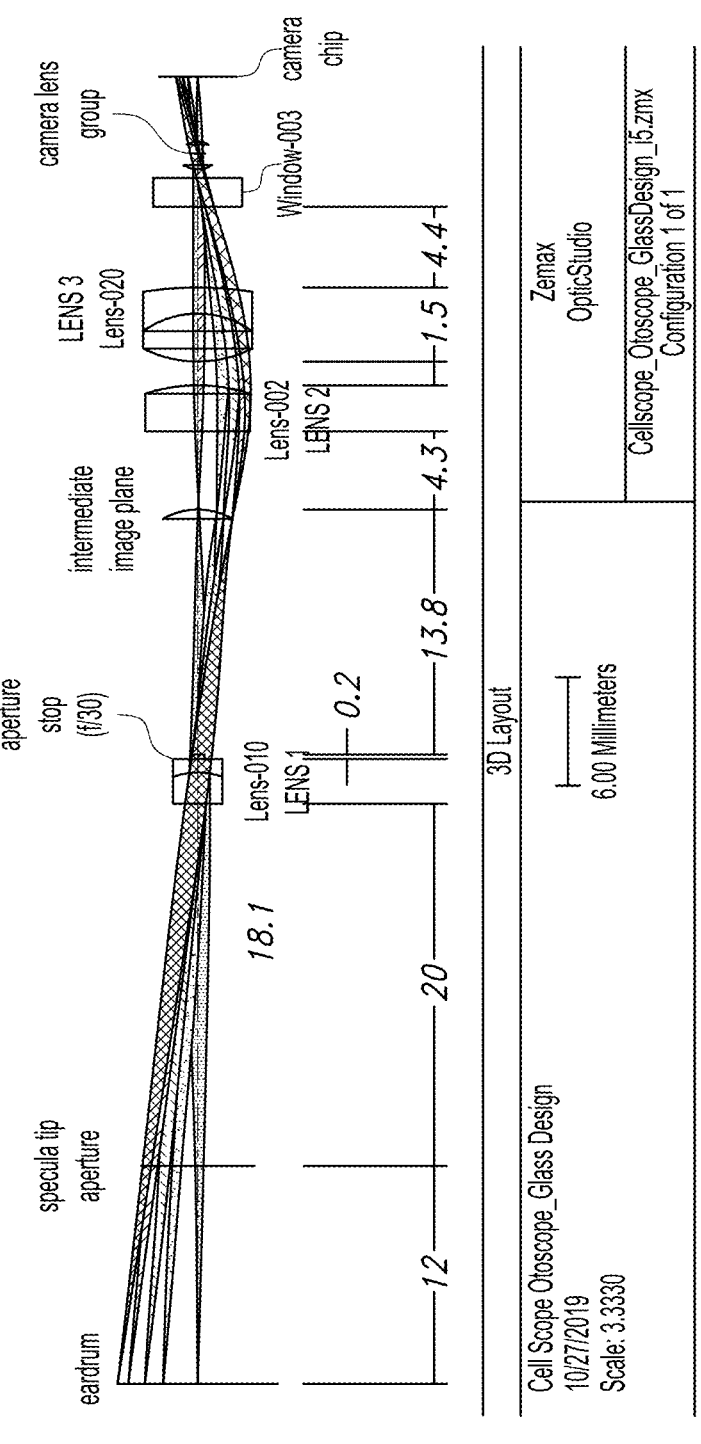
FIG. 18 depicts exemplary simulation model results to evaluate overall mechanical structure design of an exemplary otoscope device.

A tolerance analysis, as shown in FIG. 18, was performed to identify lens and lens tube specifications and dimensions of the overall mechanical structure. According to one embodiment, the first lens may influence (significantly influence) the design the mechanical structure design (e.g., of the optical system). For example, the first lens may be considered a critical component of the mechanical structure design. The cumulative effect of tube tolerances (e.g., all other lens and tube tolerances) may be acceptable as is. Accordingly, the first lens surface figure tolerance (the measure of departure for its nominal surface spherical radii) may be reduced from ±5 fringes to ±3 fringes (where one fringe is equivalent to a surface deviation of 0.32 micron).

Figure 19:
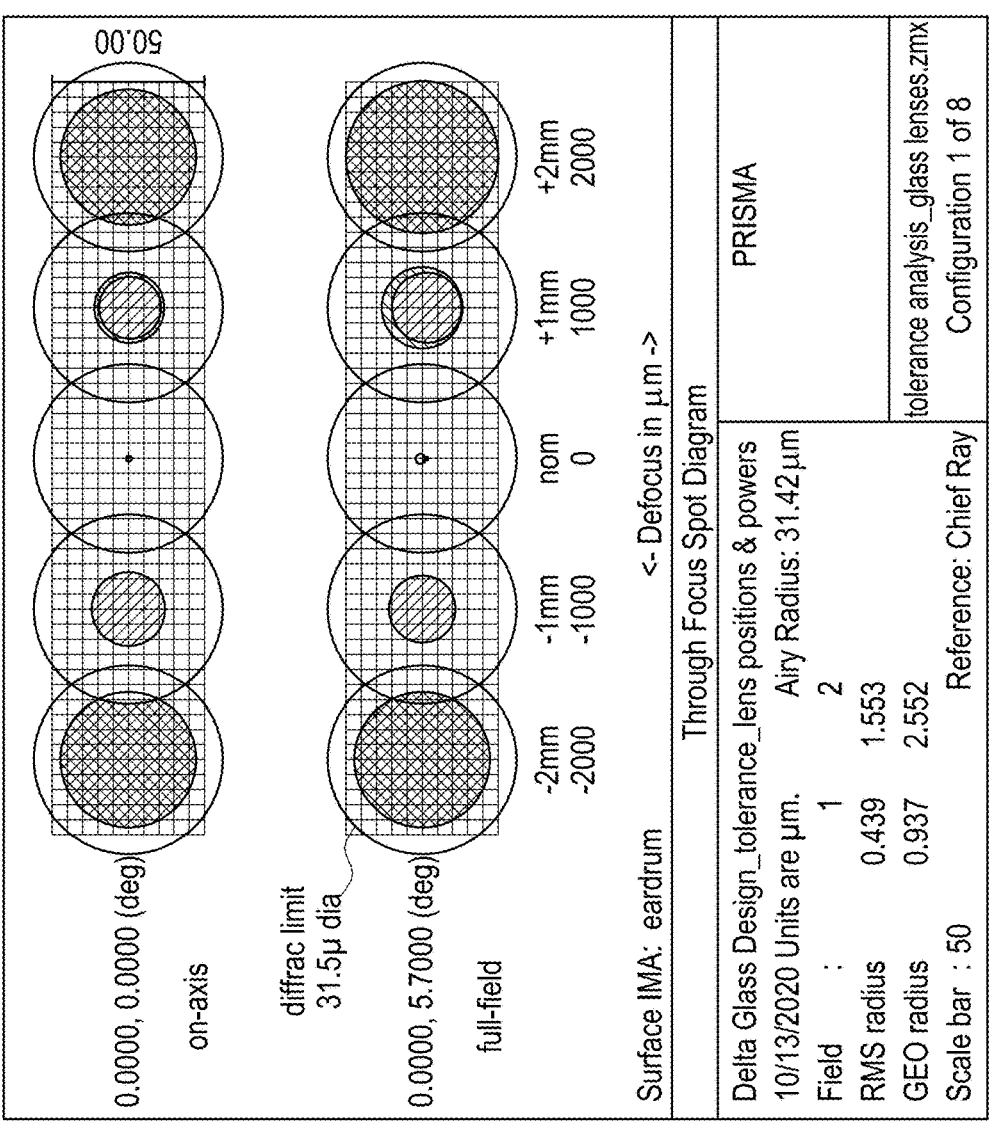
FIG. 19 depicts exemplary simulation model results using to evaluate the focal distance of an exemplary otoscope device.

The nominal focal distance from the first lens apex (i.e., the first aperture location) to the ear drum plane is 31.5 mm±0.32 mm, a range within which the geometric resolution (spot sizes) remain within the diffraction limit (i.e., the minimum theoretical resolution determined by the system f-number), as illustrated in FIG. 19. FIG. 19 traces a point source of light at the eardrum through the optics to the smartphone camera chip (e.g., an iPhone i5 without autofocus) at the center and periphery of the field of view. This simulation may define the optics' capability to retain geometric aberrations within the diffraction limit over a depth (e.g., an acceptable depth) of focus for the application.

Disclosed herein are systems, methods, and apparatus, for using a removable optical element, such as an otoscope, in combination with a smart device, such as a smartphone in such a way that a picture or video (e.g., a clear picture or a clear video) may be taken.

According to one embodiment, an otoscope apparatus, may include an objective lens configured to focus light from an object, a field lens positioned parallel to the objective lens along an optical axis, a first aperture and a second aperture positioned, respectively, at a distal end and a proximal end of the objective lens, and a third aperture positioned at a distal end of the field lens. The otoscope apparatus may be adapted to be releasably attached to a camera of a smart device.

According to an embodiment, the first aperture, second aperture and third aperture may be adapted to reduce veiling glare.

According to an embodiment, the first aperture, second aperture and third aperture may have a diameter between 0.5 mm and 4.5 mm. According to further embodiment, the first aperture may have a diameter of about 0.7 mm, the second aperture may have a diameter of about 1.2 mm, and the third aperture may have a diameter of about 4.25 mm.

According to an embodiment, the first aperture, second aperture, and third aperture may have a diameter between 0.5 mm and 4.5 mm. According to further embodiment, the first aperture may have a diameter of about 1.2 mm, the second aperture may have a diameter of about 0.7 mm, and the third aperture may have a diameter of about 4.25 mm.

According to various embodiments, a ratio of a diameter of the first aperture to a diameter of the second aperture may be about 2:1, and/or a ratio of a diameter of the second aperture to a diameter of the third aperture may be about 1:6.

According to various embodiments, the first aperture may be located about 2.6 mm from the second aperture along the optical axis, and/or the second aperture may be located about 18 mm from the third aperture along the optical axis.

According to an embodiment, a f-number of the first aperture or the second aperture may be adapted to disable an autofocus feature of the camera of the smart device. According to one example, the f-number may be f/45 or f/49.

According to one embodiment, a working distance between the first aperture and the object may be about 31.5 mm.

According to an embodiment, the otoscope apparatus may further include an eyepiece lens positioned parallel to the field lens along the optical axis.

According to an embodiment, the otoscope apparatus may further include a lens tube and a glare cap adjacent to one another along the optical axis. According to an embodiment, the objective lens and the first aperture may be positioned within the glare cap and the field lens, the second aperture and third aperture may be positioned within the lens tube.

According to an embodiment, the otoscope apparatus may further include a light source and a light pipe attachable to the light source at a proximal end, where the light pipe may terminate at a distal ring portion to illuminate the object. According to one embodiment, the light source may be a light emitting diode (LED). According to another embodiment, the light source may be a flash of the camera of the smart device. According to an embodiment, the light pipe may terminate at or prior to a distal end of the glare cap.

According to an embodiment, the first aperture may have a diameter adapted to prevent a reflection of the light back into the glare cap and/or lens tube.

According to an embodiment, the object may be the outer ear, the middle ear, and/or the ear canal of a patient. According to one example, the object may be the eardrum of a patient.

According to an embodiment, there may be a method for using the otoscope apparatus, where a picture or a video of an outer ear, the middle ear, and/or the ear canal of a patient may be captured by the camera of the smart device. According to a further embodiment, the picture or video of the outer ear, the middle ear, and/or the ear canal may be transmissible to a remote healthcare professional for diagnosis of an ear infection.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as is clear to one of ordinary skill in this and related arts, for as many items as are listed.

The term "about" or "approximately" shall be ±1%, 2%, 5% or up to 10% of the stated value.

We describe numerous examples in the present description. Features of these examples can be provided alone or in any combination, across various claim categories and types. Further, embodiments can include one or more of the following features, devices, or aspects, alone or in any combination, across various claim categories and types.

The invention claimed is:

1. An otoscope apparatus, comprising:
an objective lens configured to focus light from an object;
a field lens positioned parallel to the objective lens along an optical axis;
a first aperture and a second aperture positioned, respectively, at a distal end and a proximal end of the objective lens, wherein a ratio of a diameter of the first aperture to a diameter of the second aperture is about 1:2;
a third aperture positioned at a distal end of the field lens; and
a speculum for placing in an ear of a patient;
wherein the otoscope apparatus is adapted to be releasably attached to a camera of a smart device.

2. The otoscope apparatus of claim 1, wherein the first aperture, second aperture and third aperture are adapted to reduce veiling glare.

3. The otoscope apparatus of claim 1, wherein the first aperture, second aperture and third aperture have a diameter between 0.5 mm and 4.5 mm.

4. The otoscope apparatus of claim 1, wherein the first aperture has a diameter of about 0.7 mm, the second aperture has a diameter of about 1.2 mm, and the third aperture has a diameter of about 4.25 mm.

5. The otoscope apparatus of claim 1, wherein a ratio of a diameter of the second aperture to a diameter of the third aperture is about 1:4.

6. The otoscope apparatus of claim 1, wherein the first aperture is located about 2.6 mm from the second aperture along the optical axis.

7. The otoscope apparatus of claim 1, wherein the second aperture is located about 18 mm from the third aperture along the optical axis.

8. The otoscope apparatus of claim 1, wherein a f-number of the first aperture is adapted to assist an autofocus feature of the camera of the smart device.

9. The otoscope apparatus of claim 8, wherein the f-number is f/45.

10. The otoscope apparatus of claim 1, wherein a working distance between the first aperture and the object is about 31.5 mm.

11. The otoscope apparatus of claim 1, further comprising an eyepiece lens positioned parallel to the field lens along the optical axis.

12. The otoscope apparatus of claim 1, further comprising a lens tube and a glare cap adjacent to one another along the optical axis.

13. The otoscope apparatus of the claim 12, wherein the objective lens and the first aperture are positioned within the glare cap and the field lens, the second aperture and third aperture are positioned within the lens tube.

14. The otoscope apparatus of claim 13, further comprising:
a light source; and
a light pipe attachable to the light source at a proximal end,
wherein the light pipe terminates at a distal ring portion to illuminate the object.

15. The otoscope apparatus of claim 14, wherein the light source comprises a light emitting diode (LED).

16. The otoscope apparatus of claim 14, wherein the light source comprises a flash of the camera of the smart device.

17. The otoscope apparatus of claim 14, wherein the light pipe terminates at or prior to a distal end of the glare cap.

18. The otoscope apparatus of claim 12, wherein the first aperture has a diameter adapted to prevent a reflection of the light back into the glare cap and/or lens tube.

19. The otoscope apparatus of claim 1, wherein the object comprises at least the outer ear, the middle ear, or the ear canal of a patient.

20. The otoscope apparatus of claim 19, wherein the object comprises the eardrum of a patient.

21. A method for using the otoscope apparatus of claim 1, wherein a picture or a video of an outer ear, the middle ear, or the ear canal of a patient is captured by the camera of the smart device.

22. The method of claim 21, wherein the picture or video of the outer ear, the middle ear, or the ear canal is transmissible to a remote healthcare professional for diagnosis of an ear infection.

23. The otoscope apparatus of claim 1, wherein the speculum is removable.

* * * * *